United States Patent
Wilson et al.

(10) Patent No.: US 7,388,084 B2
(45) Date of Patent: Jun. 17, 2008

(54) **PROMOTER MOTIFS IN *CANDIDA TROPICALIS***

(75) Inventors: C. Ron Wilson, Loveland, OH (US); David L. Craft, Ft. Thomas, KY (US); Yeyan Zhang, Mason, OH (US); Jeffrey B. Stavenhagen, Brookeville, MD (US)

(73) Assignee: Cognis Corporation, Ambler, PA (US)

( * ) Notice: Subject to any disclaimer, the term of this patent is extended or adjusted under 35 U.S.C. 154(b) by 487 days.

(21) Appl. No.: 10/640,962

(22) Filed: Aug. 14, 2003

(65) Prior Publication Data

US 2005/0208497 A1    Sep. 22, 2005

Related U.S. Application Data

(60) Provisional application No. 60/403,979, filed on Aug. 16, 2002.

(51) Int. Cl.
*C07H 21/02* (2006.01)
*C07H 21/04* (2006.01)
*C12N 1/20* (2006.01)
*C12N 15/00* (2006.01)

(52) U.S. Cl. .............. 536/23.1; 435/252.3; 435/320.1; 435/440; 536/23.2

(58) Field of Classification Search ............ 435/23.1, 435/23.2, 6, 440, 252.3, 320.1; 536/23.1, 536/23.2

See application file for complete search history.

(56) References Cited

U.S. PATENT DOCUMENTS

| 5,254,466 A | 10/1993 | Pitcataggio et al. |
| 6,331,420 B1 | 12/2001 | Wilson et al. |
| 6,673,613 B2 | 1/2004 | Craft et al. |

OTHER PUBLICATIONS

Kanai, T., et al. (2000) "An n-alkane-responsive promoter element found in the gene encoding the peroxisomal protein of *Candida tropicalis* does not contain a C(6) zinc cluster DNA-binding motif" *J. Bacteriol.* 182(9):2492-2497.

Kos, W., (1995) "Expression of genes encoding peroxisomal proteins in *Saccharomyces cerevisiae* is regulated by different circuits of transcriptional control", *Biochem.Biophys.Acta* 1264(1):79-86.

Luo, Y. (1996) "Purification, identification, and properties of a *Saccharomyces cerevisiae* oleate-activated upstream activating sequence-binding protein that is involved in the activation of POX1" *J.Biol.Chem.* 271(20):12068-12075.

(Continued)

Primary Examiner—Yong D. Pak
(74) Attorney, Agent, or Firm—John F. Daniels

(57) ABSTRACT

The present invention provides modified promoters from *Candida troplicalis* CYP and POX4 genes. The modified promoters have various sequence motifs added, deleted, or altered in order to modulate expression of a coding sequence operably linked thereto. The sequence motifs comprise repressors of gene induction (URS sequences) and activators of gene induction (UAS sequences) as well as oleic acid response elements (ORE sequences). Yeast host cells comprising such modified promoters are also provided. Methods of altering expression of a protein of the beta or omega oxidation pathways using a subject modified promoter are also provided.

2 Claims, 5 Drawing Sheets

OTHER PUBLICATIONS

Rozman, D. (1996) "Structure and mapping of the human lanosterol 14alpha-demethylase gene (CYP51 encoding the cytochrome P450 involved in cholesterol biosynthesis; comparison of exon/intron orginization with other mammalian and fungal CYP genes" *Genomics* 38(3):371-381.

Sanglard, D., et al. (1989) "Characterization of the alkane-inducible cytochrome P450 (P450alk) gene from the yeast *Candida tropocalis*; identification of a new P450 gene family" *Gene* 76:121-136.

Turi, T.G. (1992) "Multiple regulatory elements control expression of the gene encoding the *Saccharomyces cerevisiae* cytochrome P450, lanosterol 14alpha-demethylase (ERG11)" *J.Biol.Chem.* 267(3):2046-2056.

Ueda, M., et al. (1985) "Peroxisomal localization of enzymes related to fatty acid β-oxidation in an η-alkane-grown yeast, *Candida tropicalis*" *Agric.Biol.Chem.* 49(6):1821-1828.

Vamecq, J. et al. (1987) "Interactions between the ω- and β-oxidations of fatty acids" *J.Biochem.* 102(1):225-234.

POX4 Promoter Sequence          Range: 1 to 531

```
         10        20        30        40        50        60
GAGCTCCAATTGTAATATTTCGGGAGAAATATCGTTGGGGTAAAACAACAGAGAGAGAGA 70        80        90       100       110       120
GGGAGAGATGGTTCTGGTAGAATTATAATCTGGTTGTTGCAAATGCTACTGATCGACTCT 130       140       150       160       170       180
GGCAATGTCTGTAGCTCGCTAGTTGTATGCAACTTAGGTGTTATGCATACACACGGTTAT 190       200       210       220       230       240
TCGGTTGAATTGTGGAGTAAAAATTGTCTGAGTTGTGTCTTAGCTACTGGCTGGCCCCCC 250       260       270       280       290       300
GCGAAAGATAATCAAAATTACACTTGTGAATTTTTGCACACACACCGATTAACATTTCCC 310       320       330       340       350       360
TTTTTTGTCCACCGATACACGCTTGCCTCTTCTTTTTTTCTCTGTGCTTCCCCCTCCTG 370       380       390       400       410       420
TGACTTTTTCCACCATTGATATAAAATCAACTCCATTTCCCTAAAATCTCCCCAGATTCT 430       440       450       460       470       480
AAAAACAACTTCTTCTCTTCTGCTTTTCCTTTTTTTTTGTTATATTTATTTACCATCCCT 490       500       510       520       530
TTTTTTTGAATAGTTATTCCCCACTAACATTGTTCAAATCTTCACGACATA
```

FIGURE 1

(PRIOR ART)

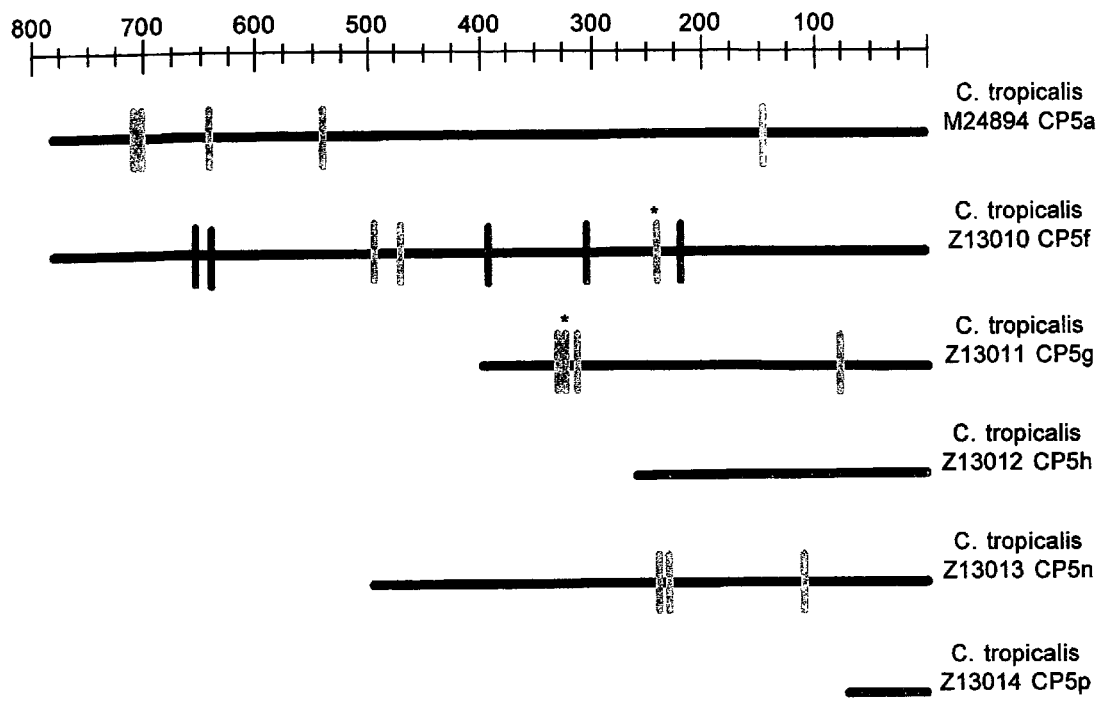
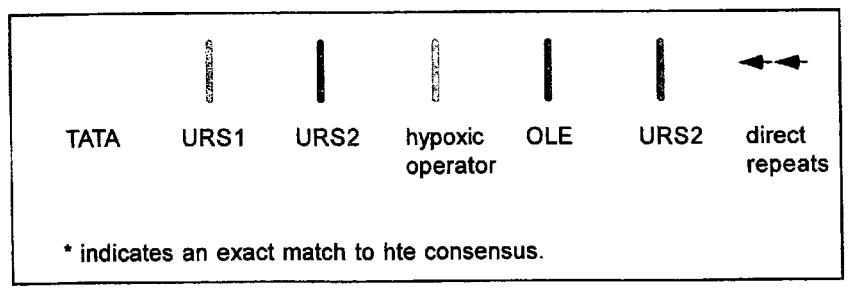
FIGURE 5

SEQUENCE LISTING

<160> NUMBER OF SEQ ID NOS: 115

<210> SEQ ID NO 1
<211> LENGTH: 6
<212> TYPE: DNA
<213> ORGANISM: Candida sp.

<400> SEQUENCE: 1 aaacga                                                                      6

<210> SEQ ID NO 2
<211> LENGTH: 6
<212> TYPE: DNA
<213> ORGANISM: Candida sp.

<400> SEQUENCE: 2 aaaccg                                                                      6

<210> SEQ ID NO 3
<211> LENGTH: 7
<212> TYPE: DNA
<213> ORGANISM: Candida sp.

<400> SEQUENCE: 3 aaagcca                                                                     7

<210> SEQ ID NO 4
<211> LENGTH: 9
<212> TYPE: DNA
<213> ORGANISM: Candida sp.
<220> FEATURE:
<221> NAME/KEY: misc_feature
<222> LOCATION: (1)..(1)
<223> OTHER INFORMATION: y is c or t
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (9)..(9)
<223> OTHER INFORMATION: v is c or a or g

<400> SEQUENCE: 4 yggttrttv                                                                   9

<210> SEQ ID NO 5
<211> LENGTH: 20
<212> TYPE: DNA
<213> ORGANISM: Candida sp.

<400> SEQUENCE: 5
gcccgggaat taccgggggc                                                      20

<210> SEQ ID NO 6
<211> LENGTH: 19
<212> TYPE: DNA
<213> ORGANISM: Candida sp.

<400> SEQUENCE: 6
ttacgtactc gcatgtatt                                                       19

<210> SEQ ID NO 7
<211> LENGTH: 6

```
<212> TYPE: DNA
<213> ORGANISM: Candida sp.

<400> SEQUENCE: 7 aaacaa                                                                    6

<210> SEQ ID NO 8
<211> LENGTH: 6
<212> TYPE: DNA
<213> ORGANISM: Candida sp.

<400> SEQUENCE: 8 aaacca                                                                    6

<210> SEQ ID NO 9
<211> LENGTH: 6
<212> TYPE: DNA
<213> ORGANISM: Candida sp.

<400> SEQUENCE: 9 aaatga                                                                    6

<210> SEQ ID NO 10
<211> LENGTH: 6
<212> TYPE: DNA
<213> ORGANISM: Candida sp.

<400> SEQUENCE: 10 aaacta                                                                    6

<210> SEQ ID NO 11
<211> LENGTH: 6
<212> TYPE: DNA
<213> ORGANISM: Candida sp.

<400> SEQUENCE: 11 aaacgg                                                                    6

<210> SEQ ID NO 12
<211> LENGTH: 6
<212> TYPE: DNA
<213> ORGANISM: Candida sp.

<400> SEQUENCE: 12 caacga                                                                    6

<210> SEQ ID NO 13
<211> LENGTH: 6
<212> TYPE: DNA
<213> ORGANISM: Candida sp.

<400> SEQUENCE: 13 aaaaga                                                                    6

<210> SEQ ID NO 14
<211> LENGTH: 6
<212> TYPE: DNA
<213> ORGANISM: Candida sp.

<400> SEQUENCE: 14 aaatga                                                                    6

<210> SEQ ID NO 15
```

```
<211> LENGTH: 6
<212> TYPE: DNA
<213> ORGANISM: Candida sp.

<400> SEQUENCE: 15 aaagga                                                                    6

<210> SEQ ID NO 16
<211> LENGTH: 6
<212> TYPE: DNA
<213> ORGANISM: Candida sp.

<400> SEQUENCE: 16 aagcga                                                                    6

<210> SEQ ID NO 17
<211> LENGTH: 6
<212> TYPE: DNA
<213> ORGANISM: Candida sp.

<400> SEQUENCE: 17 agacga                                                                    6

<210> SEQ ID NO 18
<211> LENGTH: 6
<212> TYPE: DNA
<213> ORGANISM: Candida sp.

<400> SEQUENCE: 18 acacga                                                                    6

<210> SEQ ID NO 19
<211> LENGTH: 6
<212> TYPE: DNA
<213> ORGANISM: Candida sp.

<400> SEQUENCE: 19 aaacgg                                                                    6

<210> SEQ ID NO 20
<211> LENGTH: 6
<212> TYPE: DNA
<213> ORGANISM: Candida sp.

<400> SEQUENCE: 20 atacga                                                                    6

<210> SEQ ID NO 21
<211> LENGTH: 6
<212> TYPE: DNA
<213> ORGANISM: Candida sp.

<400> SEQUENCE: 21 aaatca                                                                    6

<210> SEQ ID NO 22
<211> LENGTH: 6
<212> TYPE: DNA
<213> ORGANISM: Candida sp.

<400> SEQUENCE: 22 aaacgc                                                                    6
```

```
<210> SEQ ID NO 23
<211> LENGTH: 6
<212> TYPE: DNA
<213> ORGANISM: Candida sp.

<400> SEQUENCE: 23 aaaaga                                                                     6

<210> SEQ ID NO 24
<211> LENGTH: 6
<212> TYPE: DNA
<213> ORGANISM: Candida sp.

<400> SEQUENCE: 24 aaacgg                                                                     6

<210> SEQ ID NO 25
<211> LENGTH: 6
<212> TYPE: DNA
<213> ORGANISM: Candida sp.

<400> SEQUENCE: 25 aaacgt                                                                     6

<210> SEQ ID NO 26
<211> LENGTH: 6
<212> TYPE: DNA
<213> ORGANISM: Candida sp.

<400> SEQUENCE: 26 aaagga                                                                     6

<210> SEQ ID NO 27
<211> LENGTH: 5
<212> TYPE: DNA
<213> ORGANISM: Candida sp.

<400> SEQUENCE: 27 tacga                                                                      5

<210> SEQ ID NO 28
<211> LENGTH: 6
<212> TYPE: DNA
<213> ORGANISM: Candida sp.

<400> SEQUENCE: 28 taacga                                                                     6

<210> SEQ ID NO 29
<211> LENGTH: 6
<212> TYPE: DNA
<213> ORGANISM: Candida sp.

<400> SEQUENCE: 29 aatcga                                                                     6

<210> SEQ ID NO 30
<211> LENGTH: 6
<212> TYPE: DNA
<213> ORGANISM: Candida sp.

<400> SEQUENCE: 30 aaaccc                                                                     6
```

```
<210> SEQ ID NO 31
<211> LENGTH: 6
<212> TYPE: DNA
<213> ORGANISM: Candida sp.

<400> SEQUENCE: 31 aaacca                                                                    6

<210> SEQ ID NO 32
<211> LENGTH: 6
<212> TYPE: DNA
<213> ORGANISM: Candida sp.

<400> SEQUENCE: 32 aaagca                                                                    6

<210> SEQ ID NO 33
<211> LENGTH: 6
<212> TYPE: DNA
<213> ORGANISM: Candida sp.

<400> SEQUENCE: 33 aaatcg                                                                    6

<210> SEQ ID NO 34
<211> LENGTH: 7
<212> TYPE: DNA
<213> ORGANISM: Candida sp.

<400> SEQUENCE: 34 aaagcaa                                                                   7

<210> SEQ ID NO 35
<211> LENGTH: 6
<212> TYPE: DNA
<213> ORGANISM: Candida sp.

<400> SEQUENCE: 35 aaaccg                                                                    6

<210> SEQ ID NO 36
<211> LENGTH: 6
<212> TYPE: DNA
<213> ORGANISM: Candida sp.

<400> SEQUENCE: 36 aaacag                                                                    6

<210> SEQ ID NO 37
<211> LENGTH: 6
<212> TYPE: DNA
<213> ORGANISM: Candida sp.

<400> SEQUENCE: 37 aaacgg                                                                    6

<210> SEQ ID NO 38
<211> LENGTH: 6
<212> TYPE: DNA
<213> ORGANISM: Candida sp.

<400> SEQUENCE: 38 aaacaa                                                                    6
```

```
<210> SEQ ID NO 39
<211> LENGTH: 6
<212> TYPE: DNA
<213> ORGANISM: Candida sp.

<400> SEQUENCE: 39 aaactg                                                                     6

<210> SEQ ID NO 40
<211> LENGTH: 6
<212> TYPE: DNA
<213> ORGANISM: Candida sp.

<400> SEQUENCE: 40 aaacct                                                                     6

<210> SEQ ID NO 41
<211> LENGTH: 6
<212> TYPE: DNA
<213> ORGANISM: Candida sp.

<400> SEQUENCE: 41 acaccg                                                                     6

<210> SEQ ID NO 42
<211> LENGTH: 6
<212> TYPE: DNA
<213> ORGANISM: Candida sp.

<400> SEQUENCE: 42 aaagcc                                                                     6

<210> SEQ ID NO 43
<211> LENGTH: 7
<212> TYPE: DNA
<213> ORGANISM: Candida sp.

<400> SEQUENCE: 43 gaagcca                                                                    7

<210> SEQ ID NO 44
<211> LENGTH: 7
<212> TYPE: DNA
<213> ORGANISM: Candida sp.

<400> SEQUENCE: 44 aaagaca                                                                    7

<210> SEQ ID NO 45
<211> LENGTH: 7
<212> TYPE: DNA
<213> ORGANISM: Candida sp.

<400> SEQUENCE: 45 aaagcct                                                                    7

<210> SEQ ID NO 46
<211> LENGTH: 7
<212> TYPE: DNA
<213> ORGANISM: Candida sp.

<400> SEQUENCE: 46
```

-continued acagcca 7

<210> SEQ ID NO 47
<211> LENGTH: 7
<212> TYPE: DNA
<213> ORGANISM: Candida sp.

<400> SEQUENCE: 47 aaagaca 7

<210> SEQ ID NO 48
<211> LENGTH: 7
<212> TYPE: DNA
<213> ORGANISM: Candida sp.

<400> SEQUENCE: 48 aaatcca 7

<210> SEQ ID NO 49
<211> LENGTH: 7
<212> TYPE: DNA
<213> ORGANISM: Candida sp.

<400> SEQUENCE: 49 aaagcta 7

<210> SEQ ID NO 50
<211> LENGTH: 7
<212> TYPE: DNA
<213> ORGANISM: Candida sp.

<400> SEQUENCE: 50 aaagcaa 7

<210> SEQ ID NO 51
<211> LENGTH: 7
<212> TYPE: DNA
<213> ORGANISM: Candida sp.

<400> SEQUENCE: 51 aaagccc 7

<210> SEQ ID NO 52
<211> LENGTH: 9
<212> TYPE: DNA
<213> ORGANISM: Candida sp.

<400> SEQUENCE: 52 cggttagta 9

<210> SEQ ID NO 53
<211> LENGTH: 9
<212> TYPE: DNA
<213> ORGANISM: Candida sp.

<400> SEQUENCE: 53 tggttgatg 9

<210> SEQ ID NO 54
<211> LENGTH: 9
<212> TYPE: DNA
<213> ORGANISM: Candida sp.

<400> SEQUENCE: 54

-continued

```
cggttataa                                                                    9

<210> SEQ ID NO 55
<211> LENGTH: 9
<212> TYPE: DNA
<213> ORGANISM: Candida sp.

<400> SEQUENCE: 55 cggttttta                                                                    9

<210> SEQ ID NO 56
<211> LENGTH: 9
<212> TYPE: DNA
<213> ORGANISM: Candida sp.

<400> SEQUENCE: 56 gttgttgtc                                                                    9

<210> SEQ ID NO 57
<211> LENGTH: 9
<212> TYPE: DNA
<213> ORGANISM: Candida sp.

<400> SEQUENCE: 57 tggttgtga                                                                    9

<210> SEQ ID NO 58
<211> LENGTH: 9
<212> TYPE: DNA
<213> ORGANISM: Candida sp.

<400> SEQUENCE: 58 aggttgttc                                                                    9

<210> SEQ ID NO 59
<211> LENGTH: 9
<212> TYPE: DNA
<213> ORGANISM: Candida sp.

<400> SEQUENCE: 59 tggttgtga                                                                    9

<210> SEQ ID NO 60
<211> LENGTH: 9
<212> TYPE: DNA
<213> ORGANISM: Candida sp.

<400> SEQUENCE: 60 tggttaatg                                                                    9

<210> SEQ ID NO 61
<211> LENGTH: 9
<212> TYPE: DNA
<213> ORGANISM: Candida sp.

<400> SEQUENCE: 61 tggttcttc                                                                    9

<210> SEQ ID NO 62
<211> LENGTH: 9
<212> TYPE: DNA
<213> ORGANISM: Candida sp.
```

-continued

```
<400> SEQUENCE: 62 cggttattt                                                                  9

<210> SEQ ID NO 63
<211> LENGTH: 9
<212> TYPE: DNA
<213> ORGANISM: Candida sp.

<400> SEQUENCE: 63 cggtttttc                                                                  9

<210> SEQ ID NO 64
<211> LENGTH: 9
<212> TYPE: DNA
<213> ORGANISM: Candida sp.

<400> SEQUENCE: 64 tggtttttg                                                                  9

<210> SEQ ID NO 65
<211> LENGTH: 9
<212> TYPE: DNA
<213> ORGANISM: Candida sp.

<400> SEQUENCE: 65 tggttgtaa                                                                  9

<210> SEQ ID NO 66
<211> LENGTH: 9
<212> TYPE: DNA
<213> ORGANISM: Candida sp.

<400> SEQUENCE: 66 tggttgatc                                                                  9

<210> SEQ ID NO 67
<211> LENGTH: 7
<212> TYPE: DNA
<213> ORGANISM: Candida sp.

<400> SEQUENCE: 67 cacacca                                                                    7

<210> SEQ ID NO 68
<211> LENGTH: 10
<212> TYPE: RNA
<213> ORGANISM: Candida sp.
<220> FEATURE:
<221> NAME/KEY: misc_feature
<222> LOCATION: (6)..(6)
<223> OTHER INFORMATION: y is u or c
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (8)..(8)
<223> OTHER INFORMATION: m is a or c

<400> SEQUENCE: 68 cucucymmca                                                                10

<210> SEQ ID NO 69
<211> LENGTH: 12
```

-continued

```
<212> TYPE: RNA
<213> ORGANISM: Candida sp.
<220> FEATURE:
<221> NAME/KEY: misc_feature
<222> LOCATION: (4)..(4)
<223> OTHER INFORMATION: k is g or u
<220> FEATURE:
<221> NAME/KEY: misc_feature
<222> LOCATION: (10)..(10)
<223> OTHER INFORMATION: m is a or c
<220> FEATURE:
<221> NAME/KEY: misc_feature
<222> LOCATION: (11)..(11)
<223> OTHER INFORMATION: m is a or c

<400> SEQUENCE: 69
ggukucaagm ma                                                        12

<210> SEQ ID NO 70
<211> LENGTH: 6
<212> TYPE: RNA
<213> ORGANISM: Candida sp.

<400> SEQUENCE: 70 gggccc                                                                6

<210> SEQ ID NO 71
<211> LENGTH: 1020
<212> TYPE: DNA
<213> ORGANISM: Candida maltosa

<400> SEQUENCE: 71
atgcatgaac aggatttaat cccaagaaaa aagtctattt tctatttcca caaggaaact      60
ggaaaaacct ttttgtgttt tgaagtagct ccgtaataac ctgtaaaaaa ataaattttg     120
aagatttgac ttgctgatga aaatgctatc agtgtagctc tagacttgat actagactat    180
gatggcaaca catggtggtc aacgtgcaag acatcaccca atgagaagac tgctaaccag    240
aaaaaaaagg ggacaaaaga aaaactcgag agaaaaagtc aaattggtgt aaaattggct    300
atttttggta ctttcctaat ggggaaatta attgtttaaa attccagttt ttccagagtt    360
aagatttcga ccaattattt ttaatccata tgatcttcat cattatcaac ttgtgaaaaa    420
taataatcga ggtacgttta atacgagata ttagtctacg gctatgaatg ttggatatac    480
ttcattgacg atcagaagct tgattggtta ttcaggtgca tgtgtggata taaacccaac    540
aaattatcta gcaactgtgc cttccccaca ttggtcaaag aaaccctaaa gcaaattaaa    600
atctggataa ataaatcatt catttcacat tttccggtta gtataaggtt ttttaaattt    660
ttttttacag tttagcccct tcaattacca aatacggtaa caatgtgctt tgtaacatgc    720
aggggatttt ctccgttgct gttttctcca catgctttta atgtgtaata aattaaaaaa    780
attacaaaga aaaaccggca tataagcatc ggagtttaca ttgttaacta actgcaaaat    840
ggcgatcttt caaatcaaca aaatttaaaa aaaccccaaa aaaaaagtat catataaatt    900
aaactcaaaa tccttttgat tgcataaaat tttaaatct cttcttttt ttctttttta    960
ctttcttatc tattctattc ttttttata tatctaattc atttataaca tctggtcatg   1020

<210> SEQ ID NO 72
<211> LENGTH: 251
<212> TYPE: DNA
<213> ORGANISM: Candida maltosa

<400> SEQUENCE: 72
```

```
atgcatttga tgtgaaataa attaaaaaat tacaaagaaa atcctgcatg taaatatcgg      60
actttacatt gttaactaac tgcaaaatgt atactagatg tttcaaatca acaaaattaa     120
aaaaacccca aaaaaagtat cctataaatt aaactcaaaa tccttctgat ttttttattt     180 ttttttgtt tgttttctta tctagtcttt ttttttctct atatctaatt tatttataac      240
atctggtcat g                                                          251
```

<210> SEQ ID NO 73
<211> LENGTH: 742
<212> TYPE: DNA
<213> ORGANISM: Candida maltosa

<400> SEQUENCE: 73

```
aagcttcaca tggatcaatt gcgtttgtca catgtggtca tccagctatg gttgatgagg      60
ttagatattt tacttgtaag aatattaaca acccagaaaa gaaagagagt gattcctttg     120
aacaagtgca agtctgggct tagacgttta tttttgtttt tgttgagtgg taatacatat     180
tcttcgtatc tatgaagatt tttcacacgc ggatagtaat tgtactagcc gcttctttaa     240
gtaactgatt tacccaacaa gtacatggta atacaaactc tcactcacta gacttcgctt     300
ctagttgctt caaattagac ggttataatg tatgccaagg ttttgtgtaa tttcacggtg     360 attaacctt tccccttttt atactcctca ttatccacga tgtaatctga tctatgaacg      420
tgataagtaa cattacttag tcattaagta tggccaattc agttatacat attagtaatg     480
ctccacatcc attgtattca tatgtaatgc caaatatcac attcatttac acagaatcgg     540
ttttgttaaa tactccgcta ttgtacagca acaataggat tatgtacaga atgaaaaaca     600
aaaggcggag aaattcgacg gaaaaattta ttatttacaa atcgtattcc cgcattatct     660
ataaaacaga ttcaaaataa tctagatctc ttttttttgc ttcctttttat ttcttttttaa   720 ataagattaa actaaaaata tg                                              742
```

<210> SEQ ID NO 74
<211> LENGTH: 756
<212> TYPE: DNA
<213> ORGANISM: Candida maltosa

<400> SEQUENCE: 74

```
cagtgagcgc aacgcaatta atgtgagtta gctcactcat taggcacccc aggctttaca      60
ctttatgctt ccggctcgta tgttgtgtgg aattgtgagc ggataacaat ttcacacagg     120
aaacagctat gacatgatta cgaattccac ctatcaaaat tcacatcgat aatcgatgtg     180
tgattattgg tcaaattaat ttattactta atcccttgga aaaagcaca atcaagacc       240 cgtcttctcg taattacatt aattatatga atcatcccc ttttaatttt ttattttttt      300 atttttttg tccctgttcc aaagaatgct aactgtggag atatccaacg tccaattacc      360
atcaatagat ccgctttaat tgataatgat ggagatatga aattaccgat tccagtcaat     420
aggtccgctt ctattgataa tgatggagat atgaaattac cgattccaat caataggtcc     480
gcattaatca agtaaattac gtcagagata tatcaattaa cttatatact tgagcaaaac     540
atgtcaatct tctaacaatt acataacccg atttattcat aaacaaaaaa acaaacggag     600
aaaaaaaaat aaaacaaacg ttaaacatcg ttttacgtcc gtcttttcac acctgatcaa     660 gttactttt tttgcaatat ataaacccctt cgatttctct tcagtaaagt ataatttttta   720 tttttcatt tattttaaac tctatcaata attatg                                756
```

<210> SEQ ID NO 75
<211> LENGTH: 821
<212> TYPE: DNA
<213> ORGANISM: Candida maltosa

<400> SEQUENCE: 75

| | | |
|---|---|---|
| agtatccata attcaaagtt tagtttgaga tacatataaa tttaaacttg ttgtattttt | 60 | |
| ttaagagttt gatgttgaat gcattgaaca aaagttttta tagtttagct ttggatttaa | 120 | |
| gtaccccttg aatcacgttt tttgttattt gattcaccta gtttacgcac gatgtatcag | 180 | |
| aattagcaag tttgaggtta cttggaagtg gtggtcaact cagtaaccaa tacatatgac | 240 | |
| cagtagatat attcttataa actaataccc gtgatttaac tttatcattc gtaattacaa | 300 | |
| agctagaaac catcaaattt cacctatgta ttctttcatt gataatcaat ggttgattat | 360 | |
| tggacaaatt aaactcggaa ataacacaa acaggagac aattatttcc taattacatt | 420 | |
| aattatataa attccccctt ttattttatt ttgtcctttt gcattgataa ctgtccagat | 480 | |
| agctaccaat gcagttcaat aggtccgatt atatagatta cgtcagatat acatcaattc | 540 | |
| gcaacattaa ttcatatcaa aaccattata tttgtaggaa ttacataatc caatttattt | 600 | |
| ataaacaaac gaacggacaa aaaaaaaaat ctttaaaaca ttctcctcct ccttccttct | 660 | |
| tttcattgtt aaacatgaat ttttcccctt tgtatcatct attttcacca cacacaccaa | 720 | |
| attaagtaaa tttttttaat aatatataaa tccttctatt tctttctttc cctaaaaaaa | 780 | |
| aaatattctc tttttcttca gtccatcaat caactatcat g | 821 | |

<210> SEQ ID NO 76
<211> LENGTH: 150
<212> TYPE: DNA
<213> ORGANISM: Candida maltosa

<400> SEQUENCE: 76

| | | |
|---|---|---|
| atatgaaatt atttagatat taaccccctcg atcttttcta ataaaaaatc acacatgcaa | 60 | |
| atatcaaacc aaccaatata aataggatga aatcaaataa atgaatgatt tttgtttttt | 120 | |
| attttgatgt gtaaatccta aacaaacatg | 150 | |

<210> SEQ ID NO 77
<211> LENGTH: 771
<212> TYPE: DNA
<213> ORGANISM: Candida maltosa

<400> SEQUENCE: 77

| | | |
|---|---|---|
| aactctcttt accatcccca attatatgat gacacatctg cgtcaacgac cgaatgtagt | 60 | |
| tctgcgattc cggagtaaac ttaatatcaa gacctaagaa atcatccgg tcattctgtc | 120 | |
| ctcgcctcaa cttgaaatga tcctccaact caaatcgaag cactttcctc cttttattca | 180 | |
| aaatcttggc aatccctta tccctccaa cttcagccac taacgattcc ggaactggca | 240 | |
| atttacgtat atcgtcaatc aaccccgtcg ccaccgtgtc aaacctttca tcgctcggta | 300 | |
| tcattgtatt ggggaaaagt gtaatatgtt gtttaatatc tcgaattcga tcctatgtg | 360 | |
| gtgaaacaaa cctatagttt tgtacaagtt gtgggataag tgcaagggca tgccgacacc | 420 | |
| cttttttctat tttgctgact gttgtaatcg acggattcga tggtaaaaaa caatacgtgg | 480 | |
| caaacccttt gaacctcata ttttgttgat atttctgcag atatatttct atagtaggga | 540 | |
| gtggaacttg ttcttcttct tgttcggtat ctgactcggt gtcagaactg tattgtttga | 600 | |
| ttaattccat ctctaacttg aatctacaaa aaaaaaaaa aagaaaacga aaaaaaactt | 660 | |

```
cgatctcagc gctcggccga aagaacataa ctggactacc gttttttgata tgtttttagca      720 actccatctt cctttctttt ttctttttttg gtaatttgtt gctagttaat g                771

<210> SEQ ID NO 78
<211> LENGTH: 837
<212> TYPE: DNA
<213> ORGANISM: Candida apicola

<400> SEQUENCE: 78
gagctcggta cccggggatc tattcctcgt actatgctac gaatttagct gcctcttcta       60
ttcaggtatt tattgacctc ttcctgagca ataacaaact gctcatctta gatcaccagc      120
ggccggatgc cctgtctaac aattaatctt ccggcaaacg caaaccctct gcttctggtt      180
cggcaaattc ctcaaatcga gctcggggcg atggtggata cacgacccct ctaaatcctc      240
ttccagggtc aaatccaaga atttctccca atcgaatttc tctatttcca acgcttttag      300
ctcctctacg gcacggtcca accggacgcg ctcaaagccg tcccgagaaa gtttccatga      360
tactgtttac taacccatga tactgcttgt ctctgagagg tacagccggt gacagtcccg      420
aggagatttc aaggctataa caggtctgtg gtacccttta acgctctggg ccatctcacg      480
aaaaaattcc aactacttca atcgccgtcg cttccagttg ttgcagtgct tgagagtcaa      540
cttggtatat aatcacatgc tctgtgttca catggtgttg cattgcattt catagtgggg      600
tatttgacac gtgctcgatc acatgtaact cctaacggga aaaccgttat tcgctcgcag      660
aagctaattc cggggaatat aaatatatag agcttaattg tagattgtga gtgggatcca      720
gatagaaaag agaaatttga cgatcactta catcacgcgc agagctgttg tcgacaagta      780
atcctcttac taaatcatca attctgatag ttctcaaact gttcaacact tcccatg       837

<210> SEQ ID NO 79
<211> LENGTH: 400
<212> TYPE: DNA
<213> ORGANISM: Candida apicola

<400> SEQUENCE: 79
ataagtttct aattagtttg aaccgctaac agtttcaaca ttcgcgggat tcgggcgctc       60
tttccgtgct tcactccggt caatcgcagt gtgctacatg cttgtgggaa ttcagaccgc      120
atcgaaatag ggtagtaaca cgattatcat gtgactatgc acatgtgact tttattgcgg      180
ggtatgtacg ttatcgtccc agaaacccag ttccgacatt tgataatcaa tatataaagc      240
taacttgcgg ttttttagatt gaatagaggt ctgctggtgc tattcagata gaataggaaa      300
tttttcacaa caaggacaca acacattcaa atcaattgtt aacaagcgtt actgttgtta      360
gaccgtcatt cccagagtgt ctaatccaac acatcccatg                            400

<210> SEQ ID NO 80
<211> LENGTH: 1645
<212> TYPE: DNA
<213> ORGANISM: Yarrowia lipolytica

<400> SEQUENCE: 80
agatctgtgc gcctctacag acccatgtgg atcatgagga tgagtcacct gttggaaaat       60
gatgctctat aggttcacca acgatttagt cttgactact ggtaggaaaa caagagtgga      120
ttcgtccatc taatgactac aagtatttgc gtcgccatac ggagaaacca cagtttcaga      180
tgacgcggag tagtgggcgg tctgagtttg gcttccgcac aggatctgtc cagttacact      240
ttcacgttct tcctttgcat ggaattttct tttagcttta ctcaacaatt ttggactgtg      300
```

```
tagtgggtgg acaacaatgg agagaatgag acccagaaag tcgtatagcg acacccaaga      360
ccgaccagta gctcccatgt aaaatctctg acccaaactc ctgtcaattt ccttcattac      420
tccatgctaa aacgctagct tcggtgttcg ttttgctttt ttgattttgg cttagatttg      480
gcccaatgct tagcgaaacg cggggttccc aaacaagaca gtaatacact ggggagagga      540
caaaaatcct gacggagcaa agagaagcca gctcagaagc tattgtgagg ttccaaagag      600
accacatgct gcaggggaga ggtggggggag cccgcagaga gcacagaagt cacatctggg      660
gtctttacaa acaaacaggg ggtacctgaa tccactgact ctgggggtatg tccggggtat      720
gcagcccaca ggtcagttta gaacgccgtt tcaaacgcct gcaaaacgac ttttagagcc      780
acgagaagac tgacttgata cgcaactgga gaaacaagaa acaaatacat gtatgtactg      840
ctcaaatatc gacattgcac agatgtttca cccttcatac aacacaggta tacacgttcg      900
cagacgctaa taaccagctc tgcgatcaac tctaaccttg tgagtaaccc agcaaatgac      960
gattgcggag aagctccagc gggtgtcacg aacggtggag gtggaaaata atggtggttt     1020
aaagacataa aattggtagc aacagtgatg aggacacact ctaggacgtc tggtaccaca     1080
aggaggggcc aactgtcgct gtcatcgctg tctcctggac agcagagcta actgttgtac     1140
tccagtgacc aaccaaaatt cttctaatgt tgcggctcaa ggtctgtccc cacaactgtt     1200
gaaagcctaa gcgtcatggt aacaacgagg aacaagggct tttcgaacct tgtgcgatga     1260
caacagcatg tgaataagtg ttagtgggga agattcaaga cagcagaaag ttagcgggtg     1320
taaggggggg aggaccagag ggggtgttaa ctcatcagaa cctttcctgc cgagatgtca     1380
gcaatcaatt cgccttccat acatcttatg atgctataga ttccagttct gaggtgttcc     1440
tggtatgttt tcatcttctt tcattccatt cgagatccct caagagtgca tgtaaactga     1500
aaccttatgc caaactgagc gatcgtgaat atgaaaaagt ctgggaaagc gtcaattcaa     1560
aaaagcgaac aaaaaaagca cagaggtata tatataggtg acagcaccaa accataggtc     1620
ctccccagaa tactcctgca ctatg                                            1645
```

<210> SEQ ID NO 81
<211> LENGTH: 1819
<212> TYPE: DNA
<213> ORGANISM: Yarrowia lipolytica

<400> SEQUENCE: 81

```
gtcgacacgc ttgctgaggt tcgcgatggt ttcgtgctgg gccgacacca actggtgcaa       60
cttttcaaac tccccagcct gatgtgtctt gaaagactca tttgactgct tgagctcgtc      120
taaggctgag cggaattcct tggtattaac cgcggtagca gagtagtggt gatctcctgg      180
tgggagagcg tcaaggcgtc catcttcgcg gtgagagcct ggaactcgtc ttttgttact      240
ttcgacatgg tgaaaacgaa agaacggaaa gggaagtaaa atacgctggt acgacagtaa      300
aggcacaata aatctggcag gctatcactc gaaacaaaaa cgaggtgtcg tccaccagat      360
gtgagaaaat aaagtgcttt gtgcgtacca gggatagggt aggtagtgaa atctgagtta      420
gtacatcaac tctagacgat gggcgtcgcc tgtgtagaag aacaataact cacccggtaa      480
ctaacactat ttctcggtgg tcaatgcgtc agaagatatc aagacggtcc gttttgcgtt      540
taagccgagt gaatgttgcc tgccgttagt aaatttatta tgaaaaaccc cactatgaat      600
acatcagcct atactgatat accaagaagt gcaggggagg tggtcctgtt ccacctgaac      660
gcggttcccg acaggcggcg gtactgaagg gctttgtgag agaggtaacg ccgatttctc      720
```

```
tctgcagtcg taagcccagg tggtgtgtcc gaggcagtat cgctttccca actctagtaa      780
cctcggtagt gtgagacaca ctaccootaa cggtaggaca gccggacgac catggcgcag      840
caattggcga acgctgttat aaaacaattc acttacgtgc aatgaaagtt gtttgggcaa      900
taaacaataa atgtattaga gccagacgat agacaacaat ccagcagatg atgagcagga      960
aaattgagta agatcgacgt ggcaagaaga gttacagtta cgcagagtta ataaggtgtt     1020
gggagattag agttaccctg tcggatgact aactctccag agcgagtgtt acacatggaa     1080
cctttgctat ttcggggata accccctttg ccattgcacg atggacgtgg caaaagaaag     1140
atcgccctgc ggggatactt atcatgtggt cacatgctgt gattagaaat aaagaaaaag     1200
gtgctttttt ggcgctgtga ttaacatctc gtctgccgtg ctctactagt cgcaatagca     1260
aaaactcgct taatagtgtg catagtgcgg ggtagcagga tactgaacta cagtacgatt     1320
tgcttgctac tgcttgtagc aattacccttt actgtaggga ccacacctcc tggtttcaat     1380
gtctttcctc gcctcgacaa agcaaaactg tcacccaatc acaccttgtt catattcatt     1440
agtgcatccg ttaaccttga catgacactt ctcatactag tgatagggct gtagttgaga     1500
caagttgatt cacacggata cagacaaagc ctcagagagc aaatgttata tactcaggga     1560
ccgaccaatc aaaaaaacac actcctaata accaccattt ccatctacgc gtactcactc     1620
tgtcagctgc cccacattgc ccaatgcaca atgcacaatg atgtgtgcaa acaacgcaat     1680
caaaagtcta tgcatgctga ccaaactctg atcaccaagt tgcgaacatg aaaaagaaga     1740
cctgtgtata tataagtaag ggggagagcc ctaactagat cttttcgaaaa cccccccgacc     1800 ttcaccttcc acaaccatg                                                  1819

<210> SEQ ID NO 82
<211> LENGTH: 1036
<212> TYPE: DNA
<213> ORGANISM: Yarrowia lipolytica

<400> SEQUENCE: 82
ctgcagcggc gagaccggtt ctgggccgac tacgacgtgc ctggagggac gctccgggag       60
aatctctttg gacgggccaa gatcttcccc gaccaccctg ccggacagta caagtgggaa      120 gaggggggagt ttcccttgac caagagtgac aagagtgaga acggcaatgg agtcaatgga      180
gatgagcccg ctactaagaa acaaaaaatc tgaacaagag ccggttttag tacgatacaa      240
gagccggtac gtggacatgc agctgctttt cgaacatgaa gggagcacga ccccacgtat      300
cagtattatg caagggacca gaagtggcct cggcaaaaga ttggcctcgg tcaacaaaag      360
gtcatcatat ccgtctccgc atccgtctgt acgtgaatta tgttacttgt atctttactg      420
tactggtttg gagctacgtc gccaactaat gccaaccagt cctgtggtgt gtctataggt      480
atgtaataca agtacgagta aatgtattgt actggtgcag cacagtagat gacggagacg      540
atgaatcggt caccacccac aaacattgcc tccaaacacc gttatattgt cttactgtcg      600
tggctgagac agactcctcg gggccttgta agaggggaa tgtgtgagac agatgcccac      660
aagtgaccat gcatttgtgt gggcaggaga aaaaccaatg tttgtgggga tagaaccccat      720 caaatgaatc taaatgaact ctcccaaaat gaaccactct cttcctccaa tcaaagccct      780
gcgaaatgtc ctccgtctgt ttctcggacc cttagccgta cgacgccata ttacgatagc      840
ccgccacctt aatgcgttta acttgcatgc atgcgtctgc atacagctgc atctgtcata      900
tatgcaccat ttccccacac aactgaagtt tatatatata tactgtaagg actcctgaag      960
tggcacgaac acacctgatc acagcaacat tacagtacac tactctgctc gtatttaca     1020
```

```
atactggacg aaaatg                                                    1036

<210> SEQ ID NO 83
<211> LENGTH: 1683
<212> TYPE: DNA
<213> ORGANISM: Yarrowia lipolytica

<400> SEQUENCE: 83
aagctttcct gtaagcgtca ccgatcttgg ctgggctctt ggccgcagtt ctgattggac      60
gtgataggaa gcatctcatt agcgtcgata agataaggtg gagagtgtgg cttgagtgtg     120
acattgacgt ggataacaag acggaaaagt acgagaaggg gtctgtcagg gcagccattg     180
gttggataaa cctgatatcc cgttcttctt ggtctggagg ggataaaaat ggtgttgtat     240
ttagaaattg atgcttgtct tactccggca tcggcgagat tcggatattg gggtgagggt     300
gaacaacagc ctgtactcaa tgaaattatc ggcactaaat gtaagtacag tacataccct     360
attttttcgta cagtacttac atgatcatgg gtggaagtgt taatcaagct acagtataat     420
gtgatatctt ttggtttggc tttgcttctt gcgatccatt acatcgcaat cgactatgaa     480
tgatttcgag tttgccagaa acataaccaa gagaactatg aacttcatac tgtagtgaca     540
taagtacagg aaggcatatt tagatactca gattgagctc ttctgttttct actgaattgt     600
ttctcattta ttggtcattg ttggtatttt tttagccgaa agtatgtgtg aaatgctaaa     660
atacctctcc aaagagaagc cacctgtat tgatttcacg cagtctcttt atgaaacaaa     720
ttcttcacaa agactcttga tactacaaac acctctcaga tacctctcaa ccaccagtgt     780
tgctcatgct gaagtagtga tggcgaattg ttgattccat cttcccgaca atcacagttc     840
cacaaccaca ttccacaact ctctaataca gtaatagcct ttaatgggct gttgttcctg     900
agcctctcac cgccctggac cgtttccccc cgtttgtagc tcgcttttac tgagactgtt     960
tcgtctaaag ccttttcaaa tttatgatta ttcgtctcgg tccaaccttg tgtaaatagt    1020
gtggagaaat gatgctctat cggtgcgcat ctgtgcatga ttacatgacc atttgagctg    1080
gatatctcgt gtttggtaat gaatcaacag aaaagtttta aatcattgga acacactaca    1140
gtaacccatg ccacataaaa cgggcaccgc tcgtatataa agaatcgtcc cactagcctt    1200
agggctgcct ggattccttc tcatcacttg tcgcttttaa ttggtaaaca gcgacactct    1260
attgggagcg tgggagagaa gtaagcaaca tgaagcctat atacgagtat gcaaagtggg    1320
gccgtaagca aggacggaaa tgttgatttt cacagacagg ttgggggttg ttgtcagttt    1380
ttattgacga ttattgataa gacagatcga ggagagatat aaacccttc acccccctc     1440
ccaattgccc tcgaagctgc tcgatcaact cctttcacca cctctcttcg tccccatctt    1500
atgtttaact ttcacgttcc tcaatgcacc ccaaccaaac atggatttgg attcaagcag    1560
gttatatagt cagggccttg ctctgattcc ctttgcacct catattcctc tcacgccatg    1620
ttgaccaatc ttacgatcgt gctgatcacc cttctggtga catatacggt gctgacccgt    1680
acg                                                                  1683

<210> SEQ ID NO 84
<211> LENGTH: 1066
<212> TYPE: DNA
<213> ORGANISM: Yarrowia lipolytica

<400> SEQUENCE: 84
gtagacctcg caattcaatc ttcaatctta cgaccacttt caccacccaa aactacgtgc      60
```

-continued

| | |
|---|---|
| ctccaaatat tttcctcacc gagaccgaag tgcgagccgt cgcgtatttg gacatttcag | 120 |
| caaactctac agtaccttcg ccactgctct acttataagt aaattctctt ctatgtttat | 180 |
| attcactgca taactacaag catcgtcata caagtgccgg tacagtatgt ctcttcgatt | 240 |
| tggccctgca taatgtgggg ctatgtgaga tgacggagta atcaactcct ccgatatgcg | 300 |
| aggctgacag ttgacattat cacaagctga cactcgacgc ccccgcaaca aaggcctgtt | 360 |
| aaaaatacat ccgcatcggc ttctgtcaca aatacgcgg gcaactgctt gtacgggagt | 420 |
| ttgaaggctc ccttgtttgt taatgtcctt aagcgcttca cttcatcata ttatacatgg | 480 |
| ctgccaagag tattgccatt ctccgtggtt gcagccgggt tgaaatgtgt ttgaacgccc | 540 |
| tataacaggt gactgggcgg tcaggaagta gcaaaaaaac cattgttaga ctcgctgaaa | 600 |
| acagaatatc actccacacc tttcaaaatc ccacaactcg acctgccacc gtaaactaat | 660 |
| atctctcaaa caattggatg ggtggagaaa acggataaag cctaaaccca gatacagcac | 720 |
| tagcaactct aacccaagtt cggtggaagt cactgtgggg aaaagacga gacattgtaa | 780 |
| caggtggcac aagacgaggt ataaaacgca gttttggaaa gagaaaatga gttaaaatgg | 840 |
| cccaaatatt gccctggtag ctgtttcacc ttttatacac taaccccgaa gactttatac | 900 |
| cgcctcgtag tgcacacaaa gaccctgcac atcactccta cgtctctgcg atcactcatc | 960 |
| atagcacctt tcttgaacct tgttctgaga cccctcctgg agggagtgta taagagagag | 1020 |
| tcgtgcggca cactgagatg agccccaaac tatccattgc aatatg | 1066 |

<210> SEQ ID NO 85
<211> LENGTH: 1032
<212> TYPE: DNA
<213> ORGANISM: Yarrowia lipolytica

<400> SEQUENCE: 85

| | |
|---|---|
| gttaacgctc tttctccgtt gtcaccgact aaaactggcg cactttagat cacttgtacg | 60 |
| ctaacaaagc caccgccacg tttcagccat ttttgaaagg gtaaggatac ttgaatcatg | 120 |
| attttatgt tttcattttg tcatttccaa gtcgttcgtt atgcaccca gattttttat | 180 |
| ttttattttt atttcaacat cattttctat ttaaacatca attttatttt aaacatcaat | 240 |
| ttctatttaa acaccaattt ctatttaaac accaatttct atttcaagtt ctattcgatt | 300 |
| tccatttata tatatatttc catttccaaa atccatttcc atttccatta ttattcatct | 360 |
| ccagattcac atgtgaacct gtggcaaaac aacctttata gtcatggtgg gggatggtgg | 420 |
| catagcgggg cagtttcagc agaaaaatga tatggagcct ccggacagtc atgcggctat | 480 |
| cgagcataca tccggtcata tgtacaagta cgccccatgt accatactcg taccgtattg | 540 |
| taccgtctat gcgccgggtc accaaggtct agacgcgttt cagtgcatta caagcaccat | 600 |
| aacggcacat ctccagaccc cagattgcaa ccaaagtttg tcctgagaca gttctacaaa | 660 |
| acacactaat gtagacggag caacaatagg cgaccggata tccaaacgcg caccgtaaaa | 720 |
| accgcagcag ccgccgctca gttgcgattc acgtgaccag gagcactcct ccggggcgca | 780 |
| atctgctttt tctcgatgct gtttagtctc tatccacgtg actcgtaaaa agacccttcc | 840 |
| tcgccccccc actccactcc acaccatcgg accgtttagc gttttccgt gatgcaccct | 900 |
| tctttcacag gctgctcgta cccttccccc aaagtggaac gaagtttatc tggatggata | 960 |
| taagaagaga gaagcccaag ttggacctca gcagcgcctc aaaccacatc caccgaccac | 1020 |
| cacaatatca tg | 1032 |

<210> SEQ ID NO 86
<211> LENGTH: 690
<212> TYPE: DNA
<213> ORGANISM: Yarrowia lipolytica

<400> SEQUENCE: 86

```
gaattcccca tcgactcaca tcagggacac tacaagtgtc aatgtccagt gcacctaaaa        60
acggatctga ctaatgggat cttccgcatt acccgctgat cggagtcgaa ccatgtctct       120
ttgatgtcac acgtctgcag ggacgctttg attagctcca atgccatgtt gcgttgacaa       180
aaggtgggca tgagacactc gacatgatat ccctggaacg acaccggttc gagatggact       240
gataacatca attggcacgc cacacgtgga gagccgcctc agataaccaa ctagcgctgt       300
ctgtcggacc gaggccagcc caattacacg cacaaaacgg cactaaacgc aaacccagaa       360
catgagacaa gagtgagtga gacagggtgg agaaatgaga gatagaggag aaggaggaga       420
cgagaaatgt gacctggcg gtggagagaa gaggaaaaaa gaaactacaa gtatccagca       480
caaggagaca ctgctgagac attacatttc tgtccaatgg ggtgtgatcg acaactctgt       540
ttcactagcc taaacggcga taccgccttg cctgtcttga tcacgctcct tgtcctctga       600
ctcaagtcgc aactcctttg ttctggccca ccatggggta tatatagggt agccggtgtt       660
gttgctcatg acgacaaccg atttgacatg                                        690
```

<210> SEQ ID NO 87
<211> LENGTH: 821
<212> TYPE: DNA
<213> ORGANISM: Yarrowia lipolytica

<400> SEQUENCE: 87

```
ctgcaggttg cacttgtatc tctctcgttt attttccct attcttttg tatcgttatt         60
gaccaactac gagaggttgc attcttgtcc ctcaattaca cgctcagacc accagagaga       120
ggaggggaag aggtacgagt atgagcacaa gagcattctt tgaggacac ctgaatcgca       180
attaataata tggaaagttg tccatctttt cctcattcag ttggagaccc gacgcagttc       240
agtattgatc aaagtacaag tagatctccg aacagccaca acgtagagtc tctagcggat       300
actgtacagg ttctgtccac gaatggaatc accagaagaa gggctaagtg ttggtatatt       360
tacctcaaaa gttgctacat gaaatcttga gctttgacct agataaaact ctccctgtac       420
aagcagtcgc acaacaccac attgacgaga tgtttacaac atgatataat aactgcatga       480
aatcaaacgt aatcgaagca ctccaacttg gataaccatt gaccaatggt caacctcacg       540
tgactcaatt gtcccggggt ggcctcgtac tcgtccccac accgacacaa ccacgtgcag       600
ccgctacccc acagtcacga tccccgctag cgtcttcggg gttctgttag cgtatcaatc       660
acatgtcgag gtgtgtttta agtcgtctt tagggtggag gaatcaaggg gttgtagtag        720
tgtaccagat acatccacac aaagacatga gattacgata tatacccctaa ccaggtgttt      780
caaaaaacta caacatatca acacagaaac gctctaagat g                          821
```

<210> SEQ ID NO 88
<211> LENGTH: 1008
<212> TYPE: DNA
<213> ORGANISM: Candida tropicalis

<400> SEQUENCE: 88

```
catcaagatc atctatgggg ataattacga cagcaacatt gcagaaagag cgttggtcac        60
aatcgaaaga gcctatggcg ttgccgtcgt tgaggcaaat gacagcacca acaataacga       120
```

```
tggtcccagt gaagagcctt cagaacagtc cattgttgac gcttaaggca cggataatta      180 cgtgggcaa aggaacgcgg aattagttat gggggatca aaagcggaag atttgtgttg       240
cttgtgggtt ttttcctttta tttttcatat gatttctttg cgcaagtaac atgtgccaat    300
ttagtttgtg attagcgtgc cccacaattg gcatcgtgga cgggcgtgtt ttgtcatacc    360
ccaagtctta actagctcca cagtctcgac ggtgtctcga cgatgtcttc ttccacccct     420
cccatgaatc attcaaagtt gttggggat ctccaccaag ggcaccggag ttaatgctta     480
tgtttctccc actttggttg tgattggggt agtctagtga gttggagatt ttctttttt     540 cgcaggtgtc tccgatatcg aaatttgatg aatatagaga gaagccagat cagcacagta    600
gattgccttt gtagttagag atgttgaaca gcaactagtt gaattacacg ccaccacttg    660
acagcaagtg cagtgagctg taaacgatgc agccagagtg tcaccaccaa ctgacgttgg    720
gtggagttgt tgttgttgtt gttggcaggg ccatattgct aaacgaagac aagtagcaca    780
aaacccaagc ttaagaacaa aaataaaaaa aattcatacg acaattccaa agccattgat    840
ttacataatc aacagtaaga cagaaaaaac tttcaacatt tcaaagttcc cttttcccta    900
ttacttcttt tttttcttct ttccttcttt ccttctgttt ttcttacttt atcagtcttt    960
tacttgtttt tgcaattcct catcctcctc ctactcctcc tcaccatg                1008
```

<210> SEQ ID NO 89
<211> LENGTH: 1035
<212> TYPE: DNA
<213> ORGANISM: Candida tropicalis
<400> SEQUENCE: 89

```
tatatgatat atgatatatc ttcctgtgta attattattc gtattcgtta atacttacta     60
catttttttt tctttatttta tgaagaaaag gagagttcgt aagttgagtt gagtagaata   120
ggctgttgtg catacgggga gcagaggaga gtatccgacg aggaggaact gggtgaaatt   180
tcatctatgc tgttgcgtcc tgtactgtac tgtaaatctt agatttccta gaggttgttc   240
tagcaaataa agtgtttcaa gatacaattt tacaggcaag ggtaaaggat caactgatta   300
gcggaagatt ggtgttgcct gtggggttct tttattttttc atatgatttc tttgcgcgag   360
taacatgtgc caatctagtt tatgattagc gtacctccac aattggcatc ttggacgggc   420
gtgttttgtc ttaccccaag ccttatttag ttccacagtc tcgacggtgt ctcgccgatg   480
tcttctccca ccctcgcag gaatcattcg aagttgttgg gggatctcct ccgcagttta   540
tgttcatgtc tttcccactt tggttgtgat tggggtagcg tagtgagttg gtgatttttct  600 ttttcgcag gtgtctccga tatcgaagtt tgatgaatat aggagccaga tcagcatggt   660
atattgcctt tgtagataga gatgttgaac aacaactagc tgaattacac accaccgcta   720
aacgatgcgc acagggtgtc accgccaact gacgttgggt ggagttgttg ttggcagggc   780
catattgcta aacgaagaga agtagcacaa aacccaaggt taagaacaat taaaaaaatt   840
catacgacaa ttccacagcc atttacataa tcaacagcga caaatgagac agaaaaaact   900
ttcaacattt caaagttccc tttttcctat tacttctttt tttctttcct tcctttcatt   960
tcctttcctt ctgcttttat tactttacca gtcttttgct tgttttttgca attcctcatc  1020 ctcctcctca ccatg                                                    1035
```

<210> SEQ ID NO 90
<211> LENGTH: 1178
<212> TYPE: DNA
<213> ORGANISM: Candida tropicalis

<400> SEQUENCE: 90

```
catatgcgct aatcttcttt ttctttttat cacaggagaa actatcccac ccccacttcg      60
aaacacaatg acaactcctg cgtaacttgc aaattcttgt ctgactaatt gaaaactccg     120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat ttttttagtc ccagcattct    360
gtgggttgct ctgggtttct agaataggaa atcacaggag aatgcaaatt cagatggaag    420
aacaaagaga taaaaacaa aaaaaaactg agttttgcac aatagaatg tttgatgata     480
tcatccactc gctaaacgaa tcatgtgggt gatcttctct ttagttttgg tctatcataa    540
aacacatgaa agtgaaatcc aaatacacta cactccgggt attgtccttc gttttacaga    600
tgtctcattg tcttactttt gaggtcatag gagttgcctg tgagagatca cagagattat    660
acactcacat ttatcgtagt ttcctatctc atgctgtgtg tctctggttg gttcatgagt    720
ttggattgtt gtacattaaa ggaatcgctg gaaagcaaag ctaactaaat tttctttgtc    780
acaggtacac taacctgtaa aacttcactg ccacgccagt cttcctgat tgggcaagtg    840
cacaaactac aacctgcaaa acagcactcc gcttgtcaca ggttgtctcc ctcaaccaa    900
caaaaaata agattaaact ttctttgctc atgcatcaat cggagttatc tctgaaagag    960
ttgcctttgt gtaatgtgtg ccaaactcaa actgcaaaac taaccacaga atgatttccc   1020
tcacaattat ataaactcac ccacatttcc acagaccgta atttcatgtc tcactttctc   1080
ttttgctctt cttttactta gtcaggtttg ataacttcct ttttattac cctatcttat    1140
ttatttattt attcatttat accaaccaac caaccatg                            1178
```

<210> SEQ ID NO 91
<211> LENGTH: 1201
<212> TYPE: DNA
<213> ORGANISM: Candida tropicalis

<400> SEQUENCE: 91

```
gacctgtgac gcttccggtg tcttgccacc agtctccaag ttgaccgacg cccaagtcat     60
gtaccacttt atttccggtt acacttccaa gatggctggt actgaagaag gtgtcacgga    120
accacaagct actttctccg cttgtttcgg tcaaccattc ttggtgttgc acccaatgaa    180
gtacgctcaa caattgtctg acaagatctc gcaacacaag gctaacgcct ggttgttgaa    240
caccggttgg gttggttctt ctgctgctag aggtggtaag agatgctcat tgaagtacac    300
cagagccatt ttggacgcta tccactctgg tgaattgtcc aaggttgaat acgaaacttt    360
cccagtcttc aacttgaatg tcccaacctc ctgtccaggt gtcccaagtg aaatcttgaa    420
cccaaccaag gcctggaccg aaggtgttg actccttcaa caaggaaatc aagtctttgg    480
ctggtaagtt tgctgaaaac ttcaagacct atgctgacca gctaccgct gaagtgagag     540
ctgcaggtcc agaagcttaa agatatttat tcattattta gtttgcctat ttatttctca    600
ttacccatca tcattcaaca ctatatataa agttacttcg gatatcattg taatcgtgcg    660
tgtcgcaatt ggatgatttg gaactgcgct tgaaacggat tcatgcacga agcggagata    720
aaagattacg taatttatct cctgagacaa tttttagccgt gttcacacgc ccttctttgt    780
tctgagcgaa ggataaataa ttagacttcc acagctcatt ctaatttccg tcacgcgaat    840
```

```
attgaagggg ggtacatgtg gccgctgaat gtgggggcag taaacgcagt ctctcctctc      900
ccaggaatag tgcaacggag gaaggataac ggatagaaag cggaatgcga ggaaaatttt      960
gaacgcgcaa gaaaagcaat atccgggcta ccaggttttg agccagggaa cacactccta     1020
tttctgctca atgactgaac atagaaaaaa caccaagacg caatgaaacg cacatggaca     1080
tttagacctc cccacatgtg atagtttgtc ttaacagaaa agtataataa gaacccatgc     1140
cgtccctttt ctttcgccgc ttcaactttt ttttttttat cttacacaca tcacgaccat     1200
g                                                                    1201
```

<210> SEQ ID NO 92
<211> LENGTH: 1071
<212> TYPE: DNA
<213> ORGANISM: Candida tropicalis

<400> SEQUENCE: 92

```
gctcaacaat tgtctgacaa gatctcgcaa cacaaggcta acgcctggtt gttgaacact       60
ggttgggttg gttcttctgc tgctagaggt ggtaagagat gttcattgaa gtacaccaga      120
gccattttgg acgctatcca ctctggtgaa ttgtccaagg ttgaatacga gactttccca      180
gtcttcaact tgaatgtccc aacctcctgc ccaggtgtcc caagtgaaat cttgaaccca      240
accaaggcct ggaccgaagg tgttgactcc ttcaacaagg aaatcaagtc tttggctggt      300
aagtttgctg aaaacttcaa gacctatgct gaccaagcta ccgctgaagt tagagctgca      360
ggtccagaag cttaaagata tttattcact atttagtttg cctatttatt tctcatcacc      420
catcatcatt caacaatata tataaagtta tttcggaact catatatcat tgtaatcgtg      480
cgtgttgcaa ttgggtaatt tgaaactgta gttggaacgg attcatgcac gatgcggaga      540
taacacgaga ttatctccta agacaatttt ggcctcattc acacgccctt cttctgagct      600
aaggataaat aattagactt cacaagttca ttaaaatatc cgtcacgcga aaactgcaac      660
aataaggaag ggggggtag acgtagccga tgaatgtggg gtgccagtaa acgcagtctc      720
tctctccccc cccccccccc cccctcagg aatagtacaa cggggaagg ataacggata       780 gcaagtggaa tgcgaggaaa atttttgaatg cgcaaggaaa gcaatatccg ggctatcagg      840
ttttgagcca ggggacacac tcctcttctg cacaaaaact taacgtagac aaaaaaaaaa      900
aactccacca agacacaatg aatcgcacat ggacatttag acctccccac atgtgaaagc      960
ttctctggcg aaagcaaaaa agtataata aggacccatg ccttccctct tcctgggccg     1020
tttcaacttt ttcttttct ttgtctatca acacacacac acctcacgac c              1071
```

<210> SEQ ID NO 93
<211> LENGTH: 1128
<212> TYPE: DNA
<213> ORGANISM: Candida tropicalis

<400> SEQUENCE: 93

```
gacatcataa tgacccggtt atttcgccct caggttgctt atttgagccg taaagtgcag       60
tagaaacttt gccttgggtt caaactctag tataatggtg ataactggtt gcactcttgc      120
cataggcatg aaaataggcc gttatagtac tatatttaat aagcgtagga gtataggatg      180
catatgaccg gttttctat attttaaga taatctctag taaattttgt attctcagta       240
ggatttcatc aaatttcgca accaattctg gcgaaaaaat gattcttta cgtcaaaagc       300 tgaatagtgc agtttaaagc acctaaaatc acatatacag cctctagata cgacagagaa      360
gctctttatg atctgaagaa gcattagaat agctactatg agccactatt ggtgtatata      420
```

| | | | | | |
|---|---|---|---|---|---|
| ttagggattg | gtgcaattaa | gtacgtacta | ataaacagaa | gaaaatactt | aaccaatttc | 480 |
| tggtgtatac | ttagtggtga | gggacctttt | ctgaacattc | gggtcaaact | ttttttttgga | 540 |
| gtgcgacatc | gattttttcgt | ttgtgtaata | atagtgaacc | tttgtgtaat | aaatcttcat | 600 |
| gcaagacttg | cataattcga | gcttgggagt | tcacgccaat | ttgacctcgt | tcatgtgata | 660 |
| aaagaaaagc | caaaggtaa | ttagcagacg | caatgggaac | atggagtgga | agcaatgga | 720 |
| agcacgccca | ggacggagta | atttagtcca | cactacatct | gggggttttt | tttttgtgcg | 780 |
| caagtacaca | cctggacttt | agttttttgcc | ccataaagtt | aacaatctaa | cctttggctc | 840 |
| tccaactctc | tccgccccca | aatattcgtt | tttacaccct | caagctagcg | acagcacaac | 900 |
| acccattaga | ggaatggggc | aaagttaaac | acttttggct | tcaatgattc | ctattcgcta | 960 |
| ctacattctt | ctcttgtttt | gtgctttgaa | ttgcaccatg | tgaaataaac | gacaattata | 1020 |
| tataccttttt | catccctcct | cctatatctc | ttttttgctac | atttttgtttt | ttacgtttct | 1080 |
| tgcttttgca | ctctcccact | cccacaaaga | aaaaaaaact | acactatg | | 1128 |

<210> SEQ ID NO 94
<211> LENGTH: 915
<212> TYPE: DNA
<213> ORGANISM: Candida tropicalis

<400> SEQUENCE: 94

| | | | | | |
|---|---|---|---|---|---|
| cctgcagaat | tcgcggccgc | gtcgacagag | tagcagttat | gcaagcatgt | gattgtggtt | 60 |
| tttgcaacct | gtttgcacga | caaatgatcg | acagtcgatt | acgtaatcca | tattatttag | 120 |
| aggggtaata | aaaataaat | ggcagccaga | atttcaaaca | ttttgcaaac | aatgcaaaag | 180 |
| atgagaaact | ccaacagaaa | aaataaaaaa | actccgcagc | actccgaacc | aacaaaacaa | 240 |
| tgggggggcgc | cagaattatt | gactattgtg | acttttttttt | attttttccg | ttaactttca | 300 |
| ttgcagtgaa | gtgtgttaca | cggggtggtg | atggtgttgg | tttctacaat | gcaagggcac | 360 |
| agttgaaggt | ttccacataa | cgttgcacca | tatcaactca | atttatcctc | attcatgtga | 420 |
| taaaagaaga | gccaaaaggt | aattggcaga | cccccccaagg | ggaacacgga | gtagaaagca | 480 |
| atggaaacac | gcccatgaca | gtgccattta | gcccacaaca | catctagtat | tctttttttttt | 540 |
| ttttgtgcgc | aggtgcacac | ctggactttta | gttattgccc | cataaagtta | acaatctcac | 600 |
| ctttggctct | cccagtgtct | ccgcctccag | atgctcgttt | tacaccctcg | agctaacgac | 660 |
| aacacaacac | ccatgaggggg | aatgggcaaa | gttaaacact | tttggtttca | atgattccta | 720 |
| tttgctactc | tcttgtttttg | tgttttgatt | tgcaccatgt | gaaataaacg | acaattatat | 780 |
| ataccttttc | gtctgtcctc | caatgtctct | ttttgctgcc | attttgcttt | ttgcttttttg | 840 |
| cttttgcact | ctctcccact | cccacaatca | gtgcagcaac | acacaaagaa | gaaaaataaa | 900 |
| aaaacctaca | ctatg | | | | | 915 |

<210> SEQ ID NO 95
<211> LENGTH: 769
<212> TYPE: DNA
<213> ORGANISM: Candida tropicalis

<400> SEQUENCE: 95

| | | | | | |
|---|---|---|---|---|---|
| gatgtggtgc | ttgatttctc | gagacacatc | cttgtgaggt | gccatgaatc | tgtacctgtc | 60 |
| tgtaagcaca | gggaactgct | tcaacacctt | attgcatatt | ctgtctattg | caagcgtgtg | 120 |
| ctgcaacgat | atctgccaag | gtatatagca | gaacgtgctg | atggttcctc | cggtcatatt | 180 |

| | |
|---|---|
| ctgttggtag ttctgcaggt aaatttggat gtcaggtagt ggagggaggt ttgtatcggt | 240 |
| tgtgttttct tcttcctctc tctctgattc aacctccacg tctccttcgg gttctgtgtc | 300 |
| tgtgtctgag tcgtactgtt ggattaagtc catcgcatgt gtgaaaaaaa gtagcgctta | 360 |
| tttagacaac cagttcgttg ggcgggtatc agaaatagtc tgttgtgcac gaccatgagt | 420 |
| atgcaacttg acgagacgtc gttaggaatc cacagaatga tagcaggaag cttactacgt | 480 |
| gagagattct gcttagagga tgttctcttc ttgttgattc cattaggtgg gtatcatctc | 540 |
| cggtggtgac aacttgacac aagcagttcc gagaaccacc cacaacaatc accattccag | 600 |
| ctatcacttc tacatgtcaa cctacgtgt atctcatcac catctagttt cttggcaatc | 660 |
| gtttatttgt tatgggtcaa catccaatac aactccacca atgaagaaga aaaacggaaa | 720 |
| gcagaatacc agaatgacag tgtgagttcc tgaccattgc taatctatg | 769 |

<210> SEQ ID NO 96
<211> LENGTH: 1105
<212> TYPE: DNA
<213> ORGANISM: Candida tropicalis

<400> SEQUENCE: 96

| | |
|---|---|
| tggagtcgcc agacttgctc acttttgact cccttcgaaa ctcaaagtac gttcaggcgg | 60 |
| tgctcaacga aacgctccgt atctacccgg gggtaccacg aaacatgaag acagctacgt | 120 |
| gcaacacgac gttgccacgc ggaggaggca aagacggcaa ggaacctatc ttggtgcaga | 180 |
| agggacagtc cgttgggttg attactattg ccacgcagac ggacccagag tattttgggg | 240 |
| ccgacgctgg tgagtttaag ccggagagat ggtttgattc aagcatgaag aacttggggt | 300 |
| gtaaatactt gccgttcaat gctgggccac ggacttgctt ggggcagcag tacactttga | 360 |
| ttgaagcgag ctacttgcta gtccggttgg cccagaccta ccgggcaata gatttgcagc | 420 |
| caggatcggc gtaccaccca agaaagaagt cgttgatcaa catgagtgct gccgacgggg | 480 |
| tgtttgtaaa gctttataag gatgtaacgg tagatggata gttgtgtagg aggagcggag | 540 |
| ataaattaga tttgattttg tgtaaggttt tggatgtcaa cctactccgc acttcatgca | 600 |
| gtgtgtgtga cacaagggtg tactacgtgt gcgtgtgcgc aagagacag cccaagggg | 660 |
| tggtagtgtg tgttggcgga agtgcatgtg acacaacgcg tgggttctgg ccaatggtgg | 720 |
| actaagtgca ggtaagcagc gacctgaaac attcctcaac gcttaagaca ctggtggtag | 780 |
| agatgcggac caggctattc ttgtcgtgct acccggcgca tggaaaatca actgcgggaa | 840 |
| gaataaattt atccgtagaa tccacagagc ggataaattt gcccacctcc atcatcaacc | 900 |
| acgccgccac taactacatc actcccctat tttctctctc tctctttgtc ttactccgct | 960 |
| cccgtttcct tagccacaga tacacaccca ctgcaaacag cagcaacaat tataaagata | 1020 |
| cgccaggccc accttctttc tttttcttca cttttttgac tgcaactttc tacaatccac | 1080 |
| cacagccacc accacagccg ctatg | 1105 |

<210> SEQ ID NO 97
<211> LENGTH: 1143
<212> TYPE: DNA
<213> ORGANISM: Candida tropicalis

<400> SEQUENCE: 97

| | |
|---|---|
| ttacaatcat ggagctcgct aggaacccag atgtctggga gaagctccgc gaagaggtca | 60 |
| acacgaactt tggcatggag tcgccagact tgctcacttt tgactctctt agaagctcaa | 120 |
| agtacgttca ggcggtgctc aacgaaacgc ttcgtatcta cccgggggtg ccacgaaaca | 180 |

```
tgaagacagc tacgtgcaac acgacgttgc cgcgtggagg aggcaaagac ggtaaggaac      240
ctattttggt gcagaagggc cagtccgttg ggttgattac tattgccacg cagacggacc      300
cagagtattt tggggcagat gctggtgagt tcaaaccgga gagatggttt gattcaagca      360
tgaagaactt ggggtgtaag tacttgccgt tcaatgctgg ccccggactt gtttggggca      420
gcagtacact ttgattgaag cgagctattt gctagtcagg ttggcgcaga cctaccgggt      480
aatcgatttg ctgccagggt cggcgtaccc accaagaaag aagtcgttga tcaatatgag      540
tgctgccgat ggggtggttg taaagtttca caaggatcta gatggatatg taaggtgtgt      600
aggaggagcg gagataaatt agatttgatt ttgtgtaagg tttagcacgt caagctactc      660
cgcactttgt gtgtagggag cacatactcc gtctgcgcct gtgccaagag acggcccagg      720
ggtagtgtgt ggtggtggaa gtgcatgtga cacaataccc tggttctggc caattgggga      780
tttagtgtag gtaagctgcg acctgaaaca ctcctcaacg cttgagacac tggtgggtag      840
agatgcgggc caggaggcta ttcttgtcgt gctacccgtg cacggaaaat cgattgaggg      900
aagaacaaat ttatccgtga atccacaga gcggataaat ttgtcacatt gctgcgttgc      960
ccacccacag cattctcttt tctctctctt tgtcttactc cgctcctgtt tccttatcca     1020
gaaatacaca ccaactcata taaagatacg ctagcccagc tgtctttctt tttcttcact     1080
ttttttggtg tgttgctttt ttggctgcta ctttctacaa ccaccaccac caccaccacc     1140
atg                                                                   1143

<210> SEQ ID NO 98
<211> LENGTH: 466
<212> TYPE: DNA
<213> ORGANISM: Candida tropicalis

<400> SEQUENCE: 98
gaattctttg gatctaattc cagctgatct tgctaatcct tatcaacgta gttgtgatca       60
ttgtttgtct gaattataca caccagtgga agaatatggt ctaatttgca cgtcccactg      120
gcattgtgtt tttgtggggg gggggggggtg cacacatttt tagtgccatt ctttgttgat      180 taccccctccc ccctatcatt cattcccaca ggattagttt tttcctcact ggaattcgct      240
gtccacctgt caacccccc ccccccccc ccactgccc tacccctgccc tgccctgcac      300 gtcctgtgtt ttgtgctgtg tctttcccac gctataaaag ccctggcgtc cggccaaggt      360
ttttccaccc agccaaaaaa acagtctaaa aaatttggtt gatcctttt ggttgcaagg      420 ttttccacca ccacttccac cacctcaact attcgaacaa aagatg                    466

<210> SEQ ID NO 99
<211> LENGTH: 782
<212> TYPE: DNA
<213> ORGANISM: Candida tropicalis

<400> SEQUENCE: 99
aaaaccgata caagaagaag acagtcaaca agaacgttaa tgtcaaccag gcgccaagaa       60
gacggtttgg cggacttgga agaatgtggc atttgcccat gatgtttatg ttctggagag      120 gttttttcaag gaatcgtcat cctccgccac cacaagaacc accagttaac gagatccata      180
ttcacaaccc accgcaaggt gacaatgctc aacaacaaca gcaacaacaa caaccccccac      240 aagaacagtg gaataatgcc agtcaacaaa gagtggtgac agacgaggga gaaaacgcaa      300
gcaacagtgg ttctgatgca agatcagcta caccgcttca tcaggaaaag caggagctcc      360
```

```
caccaccata tgcccatcac gagcaacacc agcaggttag tgtatagtag tctgtagtta      420
agtcaatgca atgtaccaat aagactatcc cttcttacaa ccaagttttc tgccgcgcct      480
gtctggcaac agatgctggc cgacacactt tcaactgagt ttggtctaga attcttgcac      540
atgcacgaca aggaaactct tacaaagaca acacttgtgc tctgatgcca cttgatcttg      600
ctaagcctta tcaacgtaat tgagatcatt gtttgtctga attatacaca ccagtggaag      660
aatctggtct aatctgcacg cctcatgggc attgtgtgtt ttgggggggg ggggggggt       720 gcacacattt ttagtgcgaa tgtttgtttg ctggttcccc ctcccccctc cccctatca       780 tg                                                                    782

<210> SEQ ID NO 100
<211> LENGTH: 773
<212> TYPE: DNA
<213> ORGANISM: Candida tropicalis

<400> SEQUENCE: 100
aaagaagaca agaaaaaga tttgcggtca aatagaaaa agaaaaaga aacaactgtc         60 cgggctagtg aaatactata ctattgctag aggggtaata gaacaacggg ggattataga    120
caatttgaaa acaatagaag acacaaaata ctccatgata aaatagaaat tgatttgcaa    180
gactacaaca ggtagactta agaaaaaaa ttccgcaata ctccgaaaat acacaaaaac    240
aatactgtcc gtttccatcg cattaagaag tctattcaac aatagtttca aggagtttga    300
atatagactc cgttagaaga ttgatgttct gatttcatgt gaaaaaaat atctaatgga    360 agtatacaat taatgataat caataagtaa ctattaagaa tgtcaaatat tccaacttat    420
tcgtatcctg acaaaagtac acgccccgtt tatgcggtac ttttgtcaat tcaatttt      480 ttccccaata aagttacttt gttcaccaac aacaaccatg aggggaacca cagaattctg    540
taattttttt aaacaccagg gttcaatttc ccttccctt ttttaggtta tgaagattgg    600
ttatgttaat accatgtgaa ataaactaca aatatatata tctttttaat tgcccatctc    660
tgctactccc tctctctctc tgatgtaggt ttttctttt tttttattgt acgtgaactt    720
ggctgcacag tagaatcaat tacttttgca cctggttcta ttacacaaaa atg          773

<210> SEQ ID NO 101
<211> LENGTH: 787
<212> TYPE: DNA
<213> ORGANISM: Candida tropicalis

<400> SEQUENCE: 101
gatatcatca aagaggtcg tctgtagtga ataaatcata tggctgtagt gaatctgcta       60
cgttaaaaaa aataaaccca catgaaaagt cgaaacctac attgttagct attgttacac    120
aagttaagct gaacttgttt gacaagttat cacattcact ttctttgtgg atagctattg    180
taaagcacat ctattacaat aactagctat cttttgtaat accattcgta tcgttatggt    240
ttcatttggt gttgaagaga aaatgaataa ttgatcatta gtacacgaac ccttctatca    300
ccaaaaaatt aaaacaccaa ttttctttgt gacaattaac gtattcctaa ttaggaagta    360
ttacatggca taaacctgta aaaaatgcag aagacataaa atgcccataa taaaagttga    420
tttctccgca tgcagatggt taagtaaagt cttatgcata aatcggactt tactagtttg    480 ccctttttgtt tttgcttctt cttcttcttt ttctaatttt gttggtactg caaaaacgaa    540
ccccaaaatc aaactcttaa aacctaatta caaataacaa ctatataaac acaatgtcat    600 ttcccttttcc ccaaagttttt ccctttttttt atttttagtt tcttatatct ttacttgtac    660
```

```
ataaggtttt ctacaacttc ttttttttgga ttacttaatt aggttttact ttgacacagt    720
ccgtacttac taaattattt attccattca ttccattcat ttattcatat cacatcatat    780
aactatg                                                              787

<210> SEQ ID NO 102
<211> LENGTH: 407
<212> TYPE: DNA
<213> ORGANISM: Candida tropicalis

<400> SEQUENCE: 102
acaagatgtg gtataattac aatccaagta ttacaacgcc caagtgtgaa ggggaatgaa     60
aagaaaacga aaaaaaaaag aaataaaaac acattatcca ttctttctttt gtatagctat   120 attatatatt agtcaaacca gtatatcccc gccttgtacg gggtcctttc gttgtaattt    180
catctcgtgc ccctcctcct tcttatcacg cccatttat ttttttttttt gttcgacttt    240 ccctgtgtga aattccaacc gtggtataaa actttgtcaa tttgaccaag attgtcaagt    300
gtaaagataa aggctaaata aaagatatac tttctctttg aatagtgaca ataatctcaa    360
agtttggttg caagagtttt atttccatag tcactaatag aataatg                  407

<210> SEQ ID NO 103
<211> LENGTH: 268
<212> TYPE: DNA
<213> ORGANISM: Candida tropicalis

<400> SEQUENCE: 103
gaattctaac ggagaaatag tttcagttga cttatcattg attcctttca taaagaaaaa     60
atgatgtaac aaagggagaa caaaaaaaaa aaaggagaag caataaactc cgctccttct    120
aacaattagg caaccacaca cgttggacat atatatatat atatatgttc tggtatgttg    180
tctcctttaa ttttttccag cgattttcat cgacaacata atttattgat ctttttttt    240 tcaattagac atattccaac ccacaatg                                       268

<210> SEQ ID NO 104
<211> LENGTH: 498
<212> TYPE: DNA
<213> ORGANISM: Candida tropicalis

<400> SEQUENCE: 104
gaattcaatc ggccgttgat tagataagcc aattgttgct gtaatgtcat acagtttttt     60
tttttttttt tgattcgggt ttacagtagt tcaactggat tgttttacga gagtgataga    120
gtgacaaaat ctcgtagaca gtacaactgt atcttattgt attttttttt tgtcatcatc    180
ttcttcgcag tatacaaatg tgccggacta aaatgactgc aaaatataaa ttttagatta    240
tataaacaaa ataacaaag gagctaaaaa taggtactaa atcacggacg gtactagtac     300
tagacattgt gtatgatgag tgattgtatt gagtcaagaa taaacattag atcactattg    360
gtaaaatgtc tctttggaaa tgattaattg tacacatagt ttcgtaatgc agcatagagt    420
ggattatata aagagcagtc ataggacaaa aattatgata tcgatatcat tttgtttgta    480
tacataccat cgaccatg                                                  498

<210> SEQ ID NO 105
<211> LENGTH: 71
<212> TYPE: DNA
<213> ORGANISM: Candida tropicalis
```

-continued

```
<400> SEQUENCE: 105
acataagtat attctcttta ctatccaaat aactttatat tcattcatca aaaacctttt      60
acaccgtgat g                                                          71

<210> SEQ ID NO 106
<211> LENGTH: 3900
<212> TYPE: DNA
<213> ORGANISM: Candida tropicalis
<220> FEATURE:
<221> NAME/KEY: CDS
<222> LOCATION: (1126)..(2745)

<400> SEQUENCE: 106
gacatcataa tgacccggtt atttcgccct caggttgctt atttgagccg taaagtgcag      60
tagaaacttt gccttgggtt caaactctag tataatggtg ataactggtt gcactcttgc     120
cataggcatg aaaataggcc gttatagtac tatatttaat aagcgtagga gtataggatg     180
catatgaccg gtttttctat atttttaaga taatctctag taaattttgt attctcagta     240
ggatttcatc aaatttcgca accaattctg gcgaaaaaat gattctttta cgtcaaaagc     300
tgaatagtgc agtttaaagc acctaaaatc acatatacag cctctagata cgacagagaa     360
gctctttatg atctgaagaa gcattagaat agctactatg agccactatt ggtgtatata     420
ttagggattg gtgcaattaa gtacgtacta ataaacagaa gaaaatactt aaccaatttc     480
tggtgtatac ttagtggtga gggacctttt ctgaacattc gggtcaaact ttttttttgga   540 gtgcgacatc gattttttcgt ttgtgtaata atagtgaacc tttgtgtaat aaatcttcat    600
gcaagacttg cataattcga gcttgggagt tcacgccaat ttgacctcgt tcatgtgata     660
aaagaaaagc caaaggtaa ttagcagacg caatgggaac atggagtgga aagcaatgga     720
agcacgccca ggacggagta atttagtcca cactacatct gggggttttt tttttgtgcg     780
caagtacaca cctggacttt agttttttgcc ccataaagtt aacaatctaa cctttggctc    840
tccaactctc tccgccccca atattcgtt tttacaccct caagctagcg acagcacaac     900
acccattaga ggaatggggc aaagttaaac acttttggct tcaatgattc ctattcgcta     960
ctacattctt ctcttgtttt gtgctttgaa ttgcaccatg tgaaataaac gacaattata    1020
tatacctttt catccctcct cctatatctc ttttttgctac atttttgtttt ttacgtttct   1080 tgcttttgca ctctcccact cccacaaaga aaaaaaaact acact atg tcg tct tct    1137
                                                  Met Ser Ser Ser
                                                  1 cca tcg ttt gcc caa gag gtt ctc gct acc act agt cct tac atc gag      1185
Pro Ser Phe Ala Gln Glu Val Leu Ala Thr Thr Ser Pro Tyr Ile Glu
5                   10                  15                  20 tac ttt ctt gac aac tac acc aga tgg tac tac ttc ata cct ttg gtg      1233
Tyr Phe Leu Asp Asn Tyr Thr Arg Trp Tyr Tyr Phe Ile Pro Leu Val
            25                  30                  35 ctt ctt tcg ttg aac ttt ata agt ttg ctc cac aca agg tac ttg gaa      1281
Leu Leu Ser Leu Asn Phe Ile Ser Leu Leu His Thr Arg Tyr Leu Glu
        40                  45                  50 cgc agg ttc cac gcc aag cca ctc ggt aac ttt gtc agg gac cct acg      1329
Arg Arg Phe His Ala Lys Pro Leu Gly Asn Phe Val Arg Asp Pro Thr
    55                  60                  65 ttt ggt atc gct act ccg ttg ctt ttg atc tac ttg aag tcg aaa ggt      1377
Phe Gly Ile Ala Thr Pro Leu Leu Leu Ile Tyr Leu Lys Ser Lys Gly
70                  75                  80 acg gtc atg aag ttt gct tgg ggc ctc tgg aac aac aag tac atc gtc      1425
Thr Val Met Lys Phe Ala Trp Gly Leu Trp Asn Asn Lys Tyr Ile Val
```

```
                85                  90                  95                 100
aga gac cca aag tac aag aca act ggg ctc agg att gtt ggc ctc cca          1473
Arg Asp Pro Lys Tyr Lys Thr Thr Gly Leu Arg Ile Val Gly Leu Pro
                    105                 110                 115 ttg att gaa acc atg gac cca gag aac atc aag gct gtt ttg gct act          1521
Leu Ile Glu Thr Met Asp Pro Glu Asn Ile Lys Ala Val Leu Ala Thr
            120                 125                 130 cag ttc aat gat ttc tct ttg gga acc aga cac gat ttc ttg tac tcc          1569
Gln Phe Asn Asp Phe Ser Leu Gly Thr Arg His Asp Phe Leu Tyr Ser
                135                 140                 145 ttg ttg ggt gac ggt att ttc acc ttg gac ggt gct ggc tgg aaa cat          1617
Leu Leu Gly Asp Gly Ile Phe Thr Leu Asp Gly Ala Gly Trp Lys His
        150                 155                 160 agt aga act atg ttg aga cca cag ttt gct aga gaa cag gtt tct cac          1665
Ser Arg Thr Met Leu Arg Pro Gln Phe Ala Arg Glu Gln Val Ser His
165                 170                 175                 180 gtc aag ttg ttg gag cca cac gtt cag gtg ttc ttc aag cac gtt aga          1713
Val Lys Leu Leu Glu Pro His Val Gln Val Phe Phe Lys His Val Arg
                    185                 190                 195 aag cac cgc ggt caa acg ttc gac atc caa gaa ttg ttc ttc agg ttg          1761
Lys His Arg Gly Gln Thr Phe Asp Ile Gln Glu Leu Phe Phe Arg Leu
            200                 205                 210 acc gtc gac tcc gcc acc gag ttc ttg ttt ggt gag tct gct gaa tcc          1809
Thr Val Asp Ser Ala Thr Glu Phe Leu Phe Gly Glu Ser Ala Glu Ser
                215                 220                 225 ttg agg gac gaa tct att gga ttg acc cca acc acc aag gat ttc gat          1857
Leu Arg Asp Glu Ser Ile Gly Leu Thr Pro Thr Thr Lys Asp Phe Asp
        230                 235                 240 ggc aga aga gat ttc gct gac gct ttc aac tat tcg cag act tac cag          1905
Gly Arg Arg Asp Phe Ala Asp Ala Phe Asn Tyr Ser Gln Thr Tyr Gln
245                 250                 255                 260 gcc tac aga ttt ttg ttg caa caa atg tac tgg atc ttg aat ggc tcg          1953
Ala Tyr Arg Phe Leu Leu Gln Gln Met Tyr Trp Ile Leu Asn Gly Ser
                    265                 270                 275 gaa ttc aga aag tcg att gct gtc gtg cac aag ttt gct gac cac tat          2001
Glu Phe Arg Lys Ser Ile Ala Val Val His Lys Phe Ala Asp His Tyr
            280                 285                 290 gtg caa aag gct ttg gag ttg acc gac gat gac ttg cag aaa caa gac          2049
Val Gln Lys Ala Leu Glu Leu Thr Asp Asp Asp Leu Gln Lys Gln Asp
                295                 300                 305 ggc tat gtg ttc ttg tac gag ttg gct aag caa acc aga gac cca aag          2097
Gly Tyr Val Phe Leu Tyr Glu Leu Ala Lys Gln Thr Arg Asp Pro Lys
        310                 315                 320 gtc ttg aga gac cag tta ttg aac att ttg gtt gcc ggt aga gac acg          2145
Val Leu Arg Asp Gln Leu Leu Asn Ile Leu Val Ala Gly Arg Asp Thr
325                 330                 335                 340 acc gcc ggt ttg ttg tca ttt gtt ttc tac gag ttg tca aga aac cct          2193
Thr Ala Gly Leu Leu Ser Phe Val Phe Tyr Glu Leu Ser Arg Asn Pro
                    345                 350                 355 gag gtg ttt gct aag ttg aga gag gag gtg gaa aac aga ttt gga ctc          2241
Glu Val Phe Ala Lys Leu Arg Glu Glu Val Glu Asn Arg Phe Gly Leu
            360                 365                 370 ggt gaa gaa gct cgt gtt gaa gag atc tcg ttt gag tcc ttg aag tct          2289
Gly Glu Glu Ala Arg Val Glu Glu Ile Ser Phe Glu Ser Leu Lys Ser
                375                 380                 385 tgt gag tac ttg aag gct gtc atc aat gaa acc ttg aga ttg tac cca          2337
Cys Glu Tyr Leu Lys Ala Val Ile Asn Glu Thr Leu Arg Leu Tyr Pro
        390                 395                 400 tcg gtt cca cac aac ttt aga gtt gct acc aga aac act acc ctc cca          2385
```

| | | | | | | | | | | | | | | | |
|---|---|---|---|---|---|---|---|---|---|---|---|---|---|---|---|
| Ser | Val | Pro | His | Asn | Phe | Arg | Val | Ala | Thr | Arg | Asn | Thr | Thr | Leu | Pro |
| 405 | | | | 410 | | | | 415 | | | | 420 | | | |

```
aga ggt ggt ggt gaa gat gga tac tcg cca att gtc gtc aag aag ggt    2433
Arg Gly Gly Gly Glu Asp Gly Tyr Ser Pro Ile Val Val Lys Lys Gly
                425                 430                 435 caa gtt gtc atg tac act gtt att gct acc cac aga gac cca agt atc    2481
Gln Val Val Met Tyr Thr Val Ile Ala Thr His Arg Asp Pro Ser Ile
        440                 445                 450 tac ggt gcc gac gct gac gtc ttc aga cca gaa aga tgg ttt gaa cca    2529
Tyr Gly Ala Asp Ala Asp Val Phe Arg Pro Glu Arg Trp Phe Glu Pro
455                 460                 465 gaa act aga aag ttg ggc tgg gca tac gtt cca ttc aat ggt ggt cca    2577
Glu Thr Arg Lys Leu Gly Trp Ala Tyr Val Pro Phe Asn Gly Gly Pro
    470                 475                 480 aga atc tgt ttg ggt caa cag ttt gcc ttg acc gaa gct tca tac gtc    2625
Arg Ile Cys Leu Gly Gln Gln Phe Ala Leu Thr Glu Ala Ser Tyr Val
485                 490                 495                 500 act gtc aga ttg ctc cag gag ttt gca cac ttg tct atg gac cca gac    2673
Thr Val Arg Leu Leu Gln Glu Phe Ala His Leu Ser Met Asp Pro Asp
                505                 510                 515 acc gaa tat cca cca aaa ttg cag aac acc ttg acc ttg tcg ctc ttt    2721
Thr Glu Tyr Pro Pro Lys Leu Gln Asn Thr Leu Thr Leu Ser Leu Phe
        520                 525                 530 gat ggt gct gat gtt aga atg tac taaggttgct tttccttgct aattttcttc   2775
Asp Gly Ala Asp Val Arg Met Tyr
535                 540 tgtatagctt gtgtatttaa attgaatcgg caattgattt ttctgatacc aataaccgta   2835
gtgcgatttg accaaaaccg ttcaaacttt ttgttctctc gttgacgtgc tcgctcatca   2895
gcactgtttg aagacgaaag agaaaatttt ttgtaaacaa cactgtccaa atttacccaa   2955
cgtgaaccat tatgcaaatg agcggcccct tcaactggtc gctggaagca ttcggggata   3015
tctacaacgc ccttaagttt gaaacagaca ttgatttaga caccatagat ttcagcggca   3075
tcaagaatga ccttgcccac attttgacga ccccaacacc actggaagaa tcacgccaga   3135
aactaggcga tggatccaag cctgtgacct tgcccaatgg agacaagtg gagttgaacc    3195 aagcgttcct agaagttacc acattattgt cgaatgagtt tgacttggac caattgaacg    3255
cggcagagtt gttatactac gctggcgaca tatcctacaa gaagggcaca tcaatcgcag    3315
acagtgccag attgtcttat tatttgagag caaactacat cttgaacata cttgggtatt    3375
tgatttcgaa gcagcgattg gatttgatag tcacggacaa cgacgcgttg tttgatagta    3435
ttttgaaaag ttttgaaaag atctacaagt tgataagcgt gttgaacgat atgattgaca    3495
agcaaaaggt gacaagcgac atcaacagtc tagcattcat caattgcatc aactactcga    3555
gaggtcaact attctccgca cacgaacttt tgggactggt tttgtttgga ttggtcgaca    3615
tctatttcaa ccagtttggc acattagaca actacaagaa ggtattggca ttgatactga    3675
agaacatcag cgatgaagac atcttgatca tacacttcct cccatcgaca ctacaattgt    3735
ttaagctggt gttggacaag aaagacgacg ctgcagttga acagttctac aagtacatca    3795
cttcaacagt gtcacgagac tacaactcca acatcggctc cacagccaaa gatgatatcg    3855
atttgtccaa aaccaaactc agtggctttg aggtgttgac gagtt                    3900
```

<210> SEQ ID NO 107
<211> LENGTH: 540
<212> TYPE: PRT
<213> ORGANISM: Candida tropicalis

<400> SEQUENCE: 107

```
Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
                35                  40                  45

Arg Tyr Leu Glu Arg Arg Phe His Ala Lys Pro Leu Gly Asn Phe Val
    50                  55                  60

Arg Asp Pro Thr Phe Gly Ile Ala Thr Pro Leu Leu Leu Ile Tyr Leu
65                  70                  75                  80

Lys Ser Lys Gly Thr Val Met Lys Phe Ala Trp Gly Leu Trp Asn Asn
                85                  90                  95

Lys Tyr Ile Val Arg Asp Pro Lys Tyr Lys Thr Thr Gly Leu Arg Ile
                100                 105                 110

Val Gly Leu Pro Leu Ile Glu Thr Met Asp Pro Glu Asn Ile Lys Ala
            115                 120                 125

Val Leu Ala Thr Gln Phe Asn Asp Phe Ser Leu Gly Thr Arg His Asp
130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
            195                 200                 205

Phe Phe Arg Leu Thr Val Asp Ser Ala Thr Glu Phe Leu Phe Gly Glu
        210                 215                 220

Ser Ala Glu Ser Leu Arg Asp Glu Ser Ile Gly Leu Thr Pro Thr Thr
225                 230                 235                 240

Lys Asp Phe Asp Gly Arg Arg Asp Phe Ala Asp Ala Phe Asn Tyr Ser
                245                 250                 255

Gln Thr Tyr Gln Ala Tyr Arg Phe Leu Leu Gln Gln Met Tyr Trp Ile
        260                 265                 270

Leu Asn Gly Ser Glu Phe Arg Lys Ser Ile Ala Val Val His Lys Phe
        275                 280                 285

Ala Asp His Tyr Val Gln Lys Ala Leu Glu Leu Thr Asp Asp Asp Leu
        290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
            355                 360                 365

Arg Phe Gly Leu Gly Glu Glu Ala Arg Val Glu Glu Ile Ser Phe Glu
    370                 375                 380

Ser Leu Lys Ser Cys Glu Tyr Leu Lys Ala Val Ile Asn Glu Thr Leu
385                 390                 395                 400

Arg Leu Tyr Pro Ser Val Pro His Asn Phe Arg Val Ala Thr Arg Asn
                405                 410                 415
```

```
Thr Thr Leu Pro Arg Gly Gly Glu Asp Gly Tyr Ser Pro Ile Val
        420                 425                 430

Val Lys Lys Gly Gln Val Val Met Tyr Thr Val Ile Ala Thr His Arg
        435                 440                 445

Asp Pro Ser Ile Tyr Gly Ala Asp Ala Asp Val Phe Arg Pro Glu Arg
        450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
            485                 490                 495

Ala Ser Tyr Val Thr Val Arg Leu Leu Gln Glu Phe Ala His Leu Ser
            500                 505                 510

Met Asp Pro Asp Thr Glu Tyr Pro Pro Lys Leu Gln Asn Thr Leu Thr
            515                 520                 525

Leu Ser Leu Phe Asp Gly Ala Asp Val Arg Met Tyr
            530                 535                 540
```

<210> SEQ ID NO 108
<211> LENGTH: 6
<212> TYPE: DNA
<213> ORGANISM: Artificial Sequence
<220> FEATURE:
<223> OTHER INFORMATION: oligonucleotide

<400> SEQUENCE: 108 gggttg                                                                    6

<210> SEQ ID NO 109
<211> LENGTH: 18
<212> TYPE: DNA
<213> ORGANISM: Artificial Sequence
<220> FEATURE:
<223> OTHER INFORMATION: primer

<400> SEQUENCE: 109
caagacttgc ataattcg                                                      18

<210> SEQ ID NO 110
<211> LENGTH: 19
<212> TYPE: DNA
<213> ORGANISM: Artificial Sequence
<220> FEATURE:
<223> OTHER INFORMATION: primer

<400> SEQUENCE: 110
ccccagatgt agtgtggac                                                     19

<210> SEQ ID NO 111
<211> LENGTH: 18
<212> TYPE: DNA
<213> ORGANISM: Artificial Sequence
<220> FEATURE:
<223> OTHER INFORMATION: primer

<400> SEQUENCE: 111
gacatcataa tgacccgg                                                      18

<210> SEQ ID NO 112
<211> LENGTH: 21
<212> TYPE: DNA
<213> ORGANISM: Artificial Sequence
<220> FEATURE:

```
<223> OTHER INFORMATION: primer

<400> SEQUENCE: 112
gctcgaatta tgcaagtctt g                                              21

<210> SEQ ID NO 113
<211> LENGTH: 22
<212> TYPE: DNA
<213> ORGANISM: Artificial Sequence
<220> FEATURE:
<223> OTHER INFORMATION: primer

<400> SEQUENCE: 113
ttagtccaca ctacatctgg gg                                             22

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
catagtgtag ttttttttc                                                 20

<210> SEQ ID NO 115
<211> LENGTH: 162
<212> TYPE: DNA
<213> ORGANISM: Candida tropicalis

<400> SEQUENCE: 115
caagacttgc ataattcgag cttgggagtt cacgccaatt tgacctcgtt catgtgataa    60
aagagggttg aaaggtaatt agcagacgca atgggaacat ggagtggaaa gcaatggaag  120
cacgcccagg acggagtaat ttagtccaca ctacatctgg gg                     162
```

PROMOTER MOTIFS IN *CANDIDA TROPICALIS*

CROSS REFERENCE TO RELATED APPLICATIONS

This application claims priority from U.S. Provisional Application No. 60/403,979, filed Aug. 16, 2002, which application is incorporated by reference herein.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain rights in the invention.

BACKGROUND OF THE INVENTION

Studies of the biochemical processes by which yeasts metabolize alkanes and fatty acids have revealed three types of oxidation reactions: α-oxidation of alkanes to alcohols, ω-oxidation of fatty acids to α, ω-dicarboxylic acids and the degradative β-oxidation of fatty acids to $CO_2$ and water. The first two types of oxidations are catalyzed by microsomal enzymes while the last type takes place in the peroxisomes. In *C. tropicalis*, the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids as described, e.g., in Gilewicz et al., *Can. J. Microbiol.* 25:201 (1979), incorporated herein by reference. The genes which encode the cytochrome P450 and NADPH reductase components of the complex have previously been identified as P450ALK and P450RED respectively, and have also been cloned and sequenced as described, e.g., in Sanglard et al., *Gene* 76:121-136 (1989), incorporated herein by reference. P450ALK has also been designated P450ALK1. More recently, ALK genes have been designated by the symbol CYP and RED genes have been designated by the symbol CPR. See, e.g., Nelson, *Pharmacogenetics* 6(1):1-42 (1996), which is incorporated herein by reference. See also Ohkuma et al., *DNA and Cell Biology* 14:163-173 (1995), Seghezzi et al., *DNA and Cell Biology*, 11:767-780 (1992) and Kargel et al., *Yeast* 12:333-348 (1996), each incorporated herein by reference. In addition, CPR genes are now also referred to as NCP genes. See, e.g., De Backer et al., *Antimicrobial Agents and Chemotherapy*, 45:1660 (2001). For example, P450ALK is also designated CYP52 according to the nomenclature of Nelson, supra. Fatty acids are ultimately formed from alkanes after two additional oxidation steps, catalyzed by alcohol oxidase as described, e.g., in Kemp et al., *Appl. Microbiol. and Biotechnol.* 28: 370-374 (1988), incorporated herein by reference, and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.*, 102:225-234 (1987)). In yeast, β-oxidation takes place solely in the peroxisomes (*Agr. Biol. Chem.* 49:1821-1828 (1985)).

Cytochrome P450 monooxygenases (P450s) are terminal monooxidases of a multicomponent enzyme system including P450 and CPR (NCP). In some instances, a second electron carrier, cytochrome b5(CYTb5) and its associated reductase are involved as described below and in Morgan, et al., *Drug Metab. Disp.* 12:358-364 (1984). The P450s comprise a superfamily of proteins which exist widely in nature having been isolated from a variety of organisms as described e.g., in Nelson, supra. These organisms include various mammals, fish, invertebrates, plants, mollusk, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493-509 (1958), which is incorporated herein by reference, P450s were later named based on their absorption at 450 nm in a reduced-CO coupled difference spectrum as described, e.g., in Omura et al., *J. Biol. Chem.* 239:2370-2378 (1964), which is incorporated herein by reference.

Monooxygenation reactions catalyzed by cytochromes P450 in a eukaryotic membrane-bound system require the transfer of electrons from NADPH to P450 via NADPH-cytochrome P450 reductase (CPR) as described, e.g., in Taniguchi et al., *Arch. Biochem. Biophys.* 232:585 (1984), incorporated herein by reference. CPR is a flavoprotein of approximately 78,000 Da containing 1 mol of flavin adenine dinucleotide (FAD) and 1 mol of flavin mononucleotide (FMN) per more of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to P450 as described, e.g., in Vermilion et al., *J. Biol. Chem.* 253:8812 (1978), incorporated herein by reference. The overall reaction is as follows:

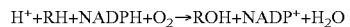

$$H^+ + RH + NADPH + O_2 \rightarrow ROH + NADP^+ + H_2O$$

Binding of a substrate to the catalytic site of P450 apparently results in a conformational change initiating electron transfer from CPR to P450. Subsequent to the transfer of the first electron, $O_2$ binds to the $Fe_2^+$-P450 substrate complex to form $Fe_3^+$-P450-substrate complex. This complex is then reduced by a second electron from CPR, or, in some cases, NADH via a second electron carrier, cytochrome b5 (CYTb5) and its associated NADH-cytochrome b5 reductase as described, e.g., in Guengerich et al., *Arch. Biochem. Biophys.* 205:365 (1980), incorporated herein by reference, and Morgan, supra. Most of the aforementioned studies implicate CYTb5 as being involved in the pathway only for the transfer of the second electron. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology*, Macmillan, New York (1986), incorporated herein by reference. With respect to the CYTb5, several other models of the role of this protein in P450 expression have been proposed besides its role as an electron carrier.

While several chemical routes to the synthesis of long-chain α,ω.-dicarboxylic acids as 9-octadecenedioic acid are available, such methods are complex and usually result in mixtures containing shorter chain lengths. As a result, extensive purification steps are necessary. As an alternative to chemical syntheses, long chain α,ω-dicarboxylic acids such as 9-octadecenedioic acid can be made via fermentation methods such as microbial transformation of the corresponding hydrocarbons such as alkanes or alkenes, fatty acids or esters thereof. One method for producing substantially pure α,ω-dicarboxylic acids in substantially quantitative yield is described in U.S. Pat. No. 5,254,466, the entire contents of which are incorporated herein by reference. This method comprises culturing a *C. tropicalis* strain wherein both copies of the chromosomal POX5 and each of the POX4A and POX4B genes are disrupted in a culture medium containing a nitrogen source, an organic substrate and a cosubstrate.

The POX4 and POX5 gene disruptions effectively block the β-oxidation pathway at its first reaction (which is catalyzed by acyl-CoA oxidase) in a *C. tropicalis* host strain. The POX4A and POX5 genes encode distinct subunits of long chain acyl-CoA oxidase, which are the peroxisomal polypeptides (PXPs) designated PXP-4 and PXP-5, respectively. The disruption of one or more of these genes results in a partial or complete inactivation of the β-oxidation pathway thus allowing enhanced yields of dicarboxylic acid by redirecting the substrate toward the α-oxidation pathway and also prevents reutilization of the dicarboxylic acid products through the β-oxidation pathway.

Another method for producing substantially pure α,ω-dicarboxylic acids in substantial yield is described in U.S. Pat. No. 6,331,420, the entire contents of which is incorporated herein by reference. This method includes increasing the CYP and CPR (NCP) enzymes by amplification of the CYP and CPR gene copy number in a *C. tropicalis* strain, and culturing the genetically modified strain in media containing an organic substrate.

Gene(s) involved in the bioconversion of various feed stocks, e.g., HOSFFA (high oleic sunflower oil, i.e., fatty acid mixtures containing oleic acid commercially available from Cognis Corp. as Edenor® and Emersol®), have native promoters that control their transcriptional regulation. These promoters are sometimes inadequate to achieve the level of transcription needed to make a gene(s) product, that is involved in a given process. Accordingly, there exists a need for tailored promoters which can aid in pocesses for increasing dicarboxylic acid production in yeast.

BRIEF SUMMARY OF THE INVENTION

The present invention provides a modified *Candida tropicalis* CYP gene promoter comprising a nucleotide sequence for a CYP gene promoter wherein one or more URS1 or URS1-like sequences have been deleted or altered so that such sequences no longer function. Preferably, the modified promoter having a deleted or altered URS1 or URS1-like sequence is substituted with another nucleotide sequence of the same or similar length. In another preferred embodiment, the deleted URS1 sequence consists of a nucleotide sequence as set forth in SEQ ID NO:1. Preferably, a deleted URS1-like sequence consists of a nucleotide sequence as set forth in at least one of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29.

Also provided by the present invention is a modified *Candida tropicalis* CYP gene promoter comprising a nucleotide sequence for a CYP gene promoter wherein one or more URS2 or URS2-like sequences have been deleted or altered to no longer function. Preferably, the deleted URS2 or URS-like sequence is substituted with another nucleotide sequence of the same or similar length.

In another preferred embodiment, the deleted URS2 sequence consists of a nucleotide sequence as set forth in SEQ ID NO:2 or SEQ ID NO:3 and the deleted URS2-like sequence consists of a nucleotide sequence as set forth in at least one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, or SEQ ID NO:51.

The present invention also provides a modified *Candida tropicalis* CYP gene promoter comprising a nucleotide sequence for a CYP gene promoter wherein one or more UAS1 sequences have been added. Preferably, the UAS1 sequence is a nucleotide sequence as set forth in SEQ ID NO:5.

In another embodiment of the invention, there is provided a modified *Candida tropicalis* CYP gene promoter wherein a contiguous sequence of 20 nucleotides comprises one or more nucleotide substitutions to form a UAS1 sequence having the sequence set forth in SEQ ID NO:5.

In still another embodiment of the invention, there is provided a modified *Candida tropicalis* CYP gene promoter comprising a nucleotide sequence for a CYP gene promoter wherein one or more UAS2 sequences have been added. Preferably, the UAS2 sequence is a nucleotide sequence as set forth in SEQ ID NO:6.

There is further provided a modified *Candida tropicalis* CYP gene promoter wherein a contiguous sequence of 19 nucleotides comprises one or more nucleotide substitutions to form a UAS2 sequence having the sequence set forth in SEQ ID NO:6.

A modified *Candida tropicalis* POX4 gene promoter comprising a nucleotide sequence for a POX4 gene promoter wherein one or more URS1 or URS1-like sequences have been added is also provided by the present invention. Preferably, the added URS1 sequence consists of a nucleotide sequence having the sequence set forth in SEQ ID NO:1 and the added URS1-like sequence consists of a nucleotide sequence having the sequence set forth in at least one of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29.

In accordance with the present invention, there is provided a modified *Candida tropicalis* POX4 gene promoter comprising a nucleotide sequence for a POX4 gene promoter wherein one or more URS2 or URS2-like sequences have been added. Preferably, the URS2 sequence is a nucleotide sequence as set forth in SEQ ID NO:2 or SEQ ID NO:3 and the added URS2-like sequence is a nucleotide sequence as set forth in at least one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, or SEQ ID NO:51.

The present invention further provides a modified *Candida tropicalis* POX4 gene promoter wherein a contiguous sequence of 6 nucleotides comprises one or more nucleotide substitutions to form a URS1 sequence having the sequence set forth in SEQ ID NO:1.

In addition, the present invention provides a modified *Candida tropicalis* POX4 gene promoter wherein a contiguous sequence of 6 nucleotides comprises one or more nucleotide substitutions to form a URS2 sequence having the sequence set forth in SEQ ID NO:2 or wherein a contiguous sequence of 7 nucleotides comprises one or more nucleotide substitutions to form a URS2 sequence having the sequence set forth in SEQ ID NO:3.

Still further, the present invention provides a modified *Candida tropicalis* POX4 gene promoter wherein a contiguous sequence of 6 nucleotides comprises one or more nucleotide substitutions to form a URS1-like sequence having the sequence set forth in at least one of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:28, or SEQ ID NO:29 or a contiguous sequence of 5 nucleotides comprises one or more nucleotide substitutions to form a URS1-like sequence having the sequence set forth SEQ ID NO:27.

A modified *Candida tropicalis* POX4 gene promoter is also provided wherein a contiguous sequence of 6 nucleotides comprises one or more substitutions to form a URS2-like sequence having the sequence set forth in at least one of: SEQ ID NO:30, SEQ ID NO:31, SEQ ID NO:32, SEQ ID NO:33, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

Still further provided is a modified *Candida tropicalis* POX4 gene promoter wherein a contiguous sequence of 7 nucleotides comprises one or more substitutions to form a URS2-like sequence having the sequence set forth in at least one of SEQ ID NO:34, SEQ ID NO:43, SEQ ID NO:44, SEQ ID NO:45, SEQ ID NO:46, SEQ ID NO:47, SEQ ID NO:48, SEQ ID NO:49, SEQ ID NO:50, or SEQ ID NO:51.

In another embodiment of the invention, there is provided a modified *Candida tropicalis* POX4 gene promoter comprising a nucleotide sequence for a POX4 gene promoter wherein one or more oleic acid response element (ORE) sequences have been deleted.

In yet another embodiment, there is provided a modified *Candida tropicalis* POX4 gene promoter comprising a nucleotide sequence for a POX4 gene promoter wherein one or more oleic acid response element (ORE) sequences have been altered so that the ORE sequence no longer functions. Preferably, the ORE consists of a nucleotide sequence as set forth in SEQ ID NO:4.

The present invention also provides a modified *Candida tropicalis* CYP gene promoter comprising a nucleotide sequence for a CYP gene promoter wherein one or more oleic acid response element (ORE) sequences or ORE-like sequences have been added. Preferably, the ORE sequence consists of a nucleotide sequence as set forth in SEQ ID NO:4 and the ORE-like sequence consists of a nucleotide sequence as set forth in any one of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO: 65, or SEQ ID NO:66.

Examples of CYP genes which may have modified promoters in accordance with the present invention include, e.g., CYP52A1A, CYP52A2A, CYP52A2B, CYP52A3A, CYP52A3B, CYP52A5A, CYP52A5B, CYP52A8A, CYP52A8B, and CYP52D4A genes, the sequences of which are disclosed in U.S. Pat. No. 6,331,420, and incorporated by reference herein as if fully set forth.

Yeast host cells comprising any of the subject modified promoters are also provided by the present invention. Preferably, the yeast host cell is *Candida* sp. Even more preferably, the yeast host cell is *Candida tropicalis*.

The present invention also provides a method for modulating expression of a protein of the beta or omega oxidation pathway in a yeast cell. The method comprises the steps of: (a) isolating a CYP gene promoter from *C. tropicalis*, (b) modifying the promoter by deletion of one or more URS1, URS2, URS1-like, or URS2-like sequences; (c) operably linking the modified promoter with a coding sequence for a protein of the omega or beta oxidation pathway, (d) transforming a yeast cell with the modified promoter operably linked to the coding sequence; and (e) growing the yeast under conditions favorable for expression of the coding sequence under the control of the modified promoter.

In another embodiment of the invention, there is provided a method for modulating expression of a protein of the beta or omega oxidation pathway in a yeast cell. The method comprises the steps of: (a) isolating a CYP gene promoter from *C. tropicalis*, (b) modifying the promoter by addition of one or more UAS1 or UAS2 sequences; (c) operably linking the modified promoter with a coding sequence for a protein of the omega or beta oxidation pathway, (d) transforming a yeast cell with the modified promoter operably linked to the coding sequence; and (e) growing the yeast under conditions favorable for expression of the coding sequence under the control of the modified promoter.

BRIEF DESCRIPTION OF THE DRAWINGS

FIG. 5 is a graphical representation of CYP gene regulatory regions in different strains of *C. tropicalis*.

DETAILED DESCRIPTION OF THE INVENTION

Figure 2:
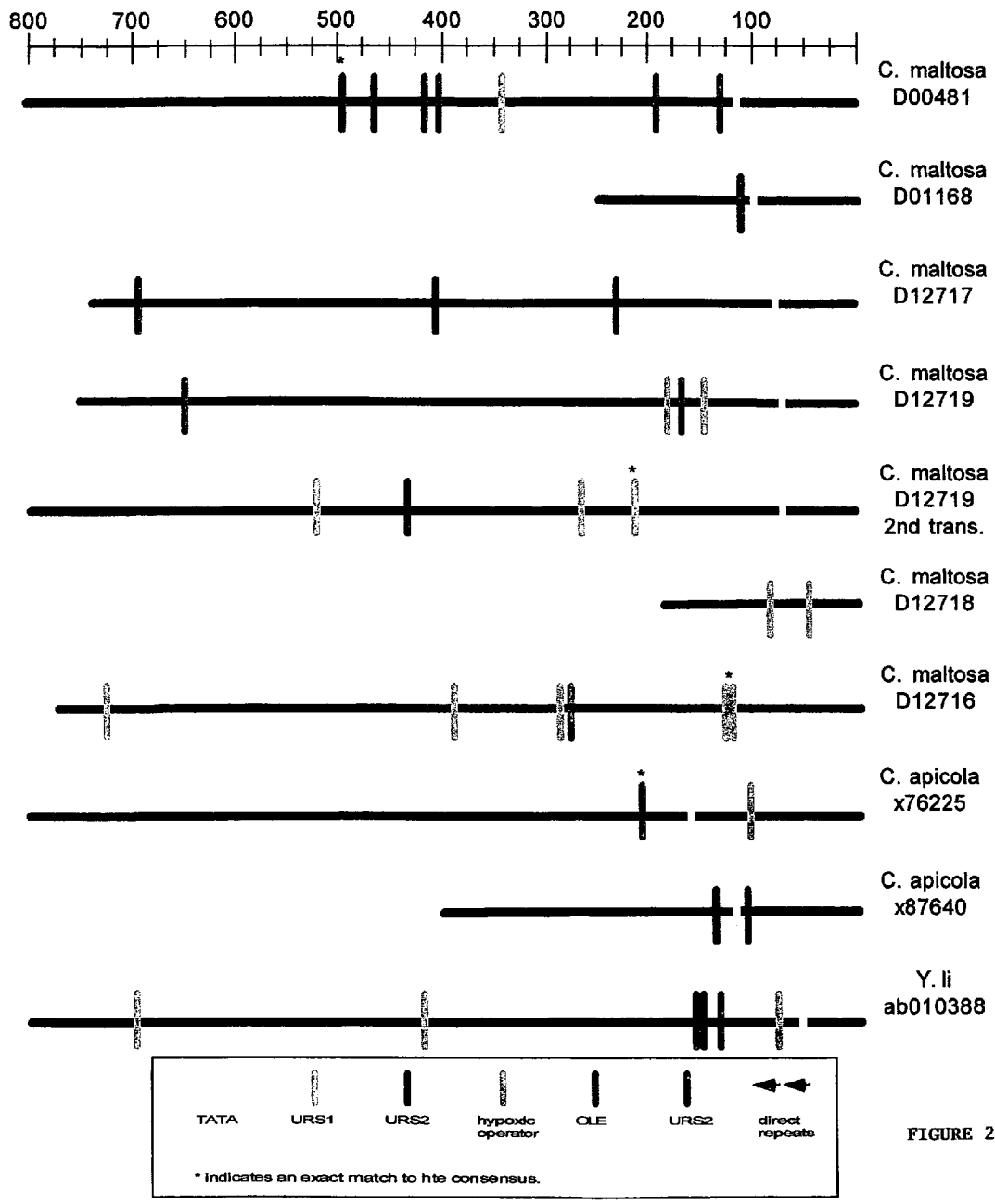
FIG. 2 is a graphical representation of CYP gene regulatory regions for different strains of *Candida maltosa*, *Candida apicola*, and *Yarrowia lipolytica*.
Figure 3:
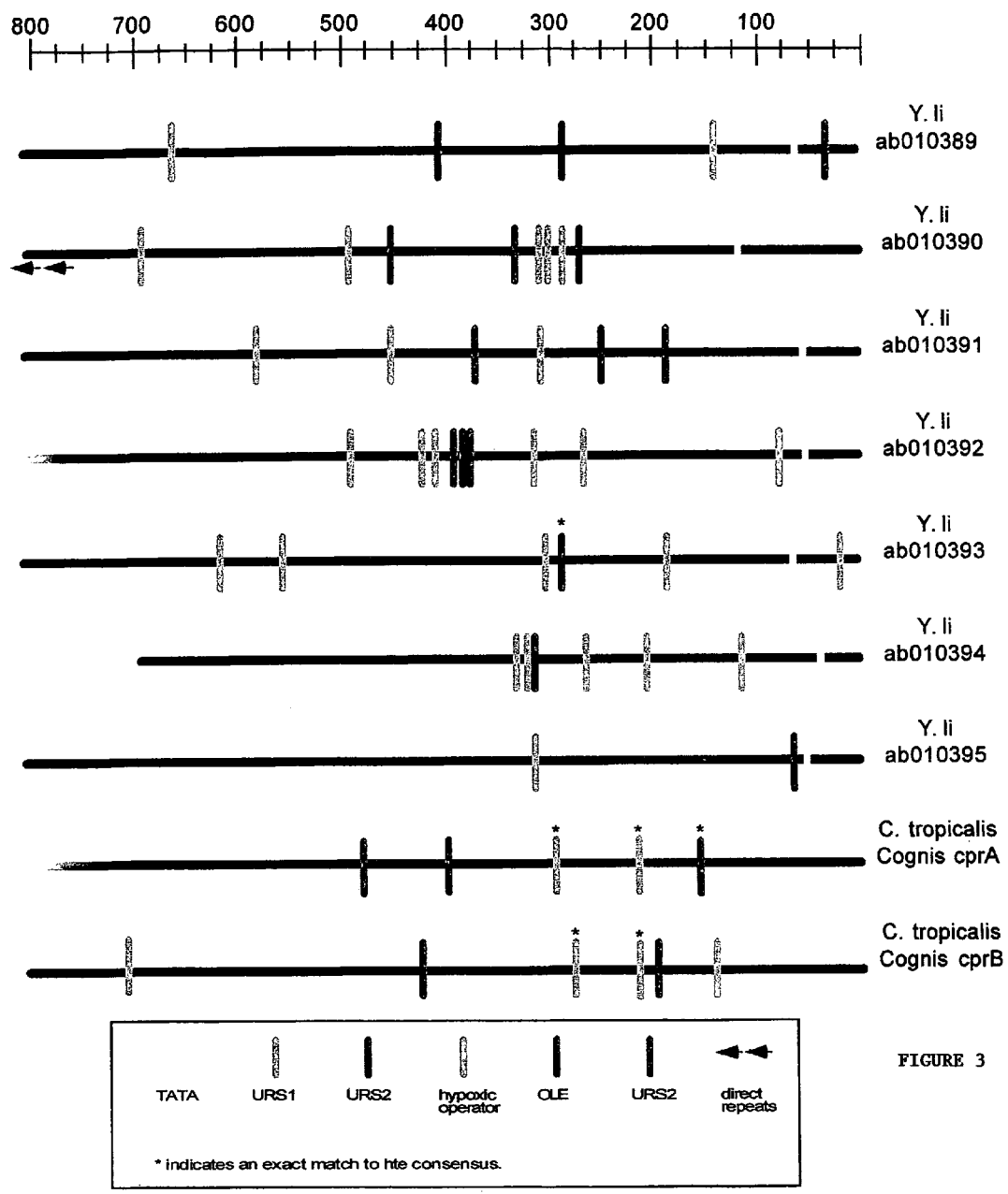
FIG. 3 is a graphical representation of CYP gene regulatory regions for different strains of *Yarrowia lipolytica* and CPR gene regulatory regions for *Candida tropicalis*.
Figure 4:
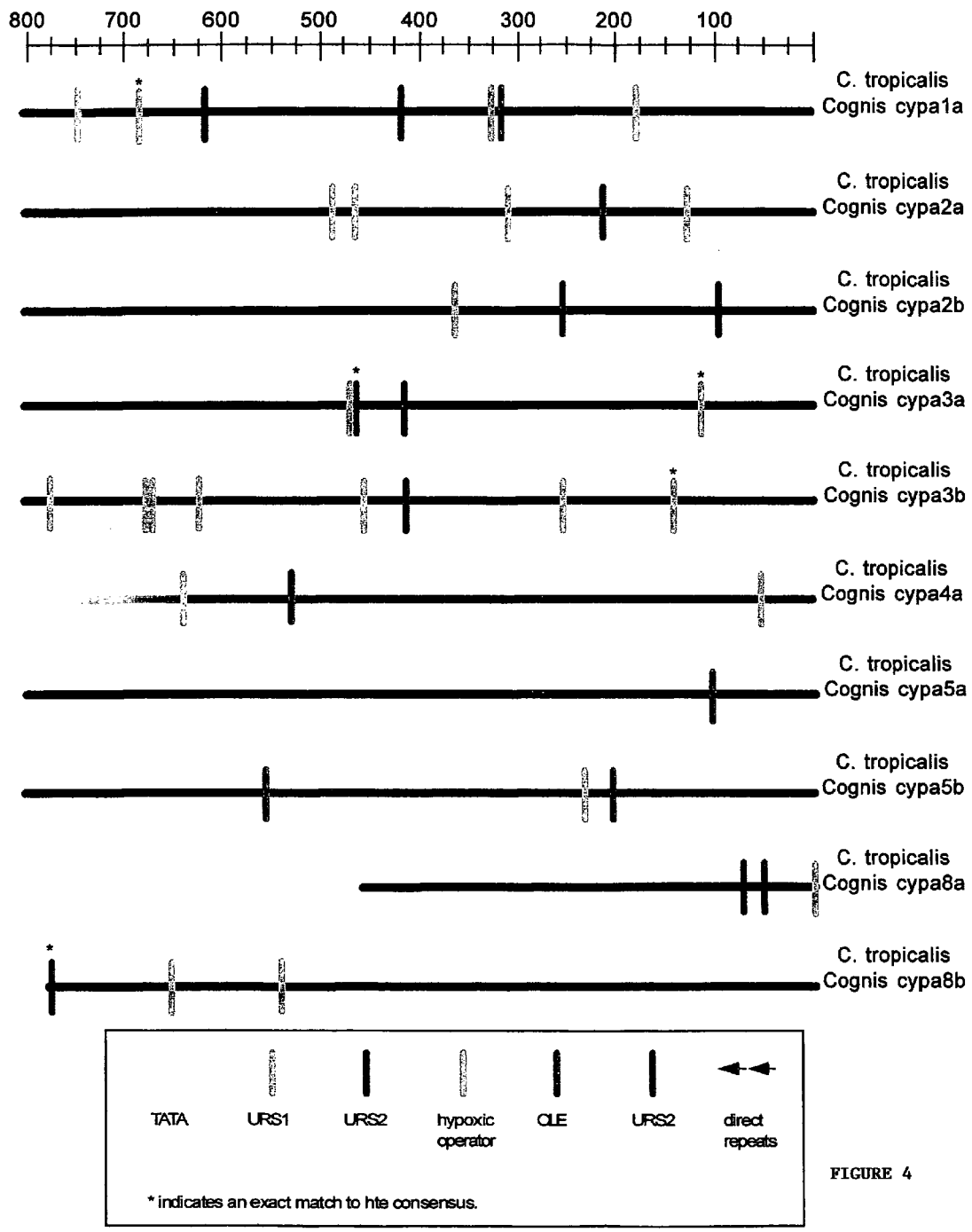
FIG. 4 is a graphical representation of regulatory regions in *C. tropicalis* CYP genes. CYP521A, CYP52A2A, CYP52A2B, CYP52A3A, CYP52A3B, CYP52A4A, CYP52A5A, CYP52A5B, CYP52A8A, and CYP52A8B are all represented.

In accordance with the present invention, sequence motifs in the upstream regulatory regions of *Candida tropicalis* cytochrome P450 monooxygenase genes (CYP52) and POX genes have been identified. These sequence motifs (also referred to herein as regulatory sequences or promoter motifs) act as either inducers or repressors of gene expression. The present invention is directed to such sequence motifs as well as to the use thereof for the regulation of coding sequences located either upstream or downstream to a subject sequence motif. In addition, the present invention provides upstream regulatory sequences, including promoter sequences, wherein one or more subject sequence motifs has been deleted as well as the use of such sequences in the regulation of coding sequences operably linked thereto. Also provided by the present invention are upstream regulatory sequences, including promoter sequences, wherein one or more subject sequence motifs has been added or substituted, as well as the use of such sequences. The term "operably linked" refers to the association of nucleic acid sequences so that the function of one is affected by the other. A promoter is operably linked with an open reading frame when it is capable of affecting the expression of the open reading frame (ORF) (i.e., the ORF is under the transcriptional control of the promoter). Notwithstanding the presence of other sequences between a promoter and an ORF, or between a subject sequence motif and an ORF, it should be understood that such a promoter or such a sequence motif is still considered operably linked to the ORF.

The sequence motifs of the present invention may be broadly characterized into: (i) URS sequences which function as repressors of gene induction; and (ii) UAS sequences, which function as activators of gene induction. The sequence motifs of the present invention may be used in conjunction with the corresponding genes from which they are derived, or with other, heterologous coding and non-coding sequences, to modulate expression thereof. In one embodiment, there is provided a sequence motif designated URS1, having the following nucleotide sequence in the 5' to 3' direction:

5' A A A C G A 3' (SEQ ID NO:1)

In another embodiment of the invention, there is provided a sequence motif designated URS2, having the following nucleotide sequence in the 5' to 3' direction:

5' A A A C C G 3' (SEQ ID NO:2)

Alternatively, the URS2 sequence motif has the following nucleotide sequence in the 5' to 3' direction:

5' A A A G C C A 3' (SEQ ID NO:3)

In still another embodiment of the invention, there is provided an oleic acid responsive element, ORE, having a positive influence on gene induction and having the following nucleotide sequence in the 5' to 3' direction:

5' C/T GGTT A/G TT C/A/G 3' (SEQ ID NO:4)

wherein the nucleotide at position 1 may be C or T, the nucleotide at position 6 may be A or G, and the nucleotide at position 9 may be C, A, or G.

The present invention also provides a sequence motif designated UAS1 having the following nucleotide sequence in the 5' to 3' direction:

(SEQ ID NO:5)
5' G C C C G G G A A T T A C C G G G G C 3'

A sequence motif designated UAS2 is also provided, having the following nucleotide sequence in the 5' to 3' direction:

(SEQ ID NO:6)
5' T T A C G T A C T C G C A T G T A T T 3'

In accordance with the present invention, a subject URS, UAS, or ORE sequence may have the exact nucleotide sequence described above, or may differ in one or more nucleotide positions. Preferably, a URS, UAS, or ORE of the present invention differs in no more than two nucleotide positions from the sequences defined above. More preferably, a URS, UAS, or ORE of the present invention differs in no more than one nucleotide position from the sequences defined above. Most preferably, a URS, UAS, or ORE of the present invention does not differ in any nucleotide position from the sequences defined above. When a sequence motif differs from the nucleotide sequences defined above for URS1, URS2, UAS1, UAS2, or ORE, such a sequence may be termed a URS-like sequence, UAS-like sequence or ORE-like sequence. All of such sequences, either the URS1, URS2, UAS1, UAS2, and ORE sequences defined above, as well as URS1-like sequences, URS2-like sequences, UAS1-like sequences, UAS2-like sequences and ORE-like sequences are encompassed by the present invention.

For example, a URS1-like sequence includes but is not limited to the following sequences:

| | |
|---|---|
| AAACAA | (SEQ ID NO:7) |
| AAACCA | (SEQ ID NO:8) |
| AAATGA | (SEQ ID NO:9) |
| AAACTA | (SEQ ID NO:10) |
| AAACGG | (SEQ ID NO:11) |
| CAACGA | (SEQ ID NO:12) |
| AAAAGA | (SEQ ID NO:13) |
| AAATGA | (SEQ ID NO:14) |
| AAAGGA | (SEQ ID NO:15) |
| AAGCGA | (SEQ ID NO:16) |
| AGACGA | (SEQ ID NO:17) |
| ACACGA | (SEQ ID NO:18) |
| AAACGG | (SEQ ID NO:19) |
| ATACGA | (SEQ ID NO:20) |
| AAATCA | (SEQ ID NO:21) |
| AAACGC | (SEQ ID NO:22) |
| AAAAGA | (SEQ ID NO:23) |
| AAACGG | (SEQ ID NO:24) |
| AAACGT | (SEQ ID NO:25) |
| AAAGGA | (SEQ ID NO:26) |
| TACGA | (SEQ ID NO:27) |
| TAACGA | (SEQ ID NO:28) |
| AATCGA | (SEQ ID NO:29) |

Examples of URS2-like sequences include but are not limited to:

| | |
|---|---|
| AAACCC | (SEQ ID NO:30) |
| AAACCA | (SEQ ID NO:31) |

-continued

| | |
|---|---|
| AAAGCA | (SEQ ID NO:32) |
| AAATCG | (SEQ ID NO:33) |
| AAAGCAA | (SEQ ID NO:34) |
| AAACCG | (SEQ ID NO:35) |
| AAACAG | (SEQ ID NO:36) |
| AAACGG | (SEQ ID NO:37) |
| AAACAA | (SEQ ID NO:38) |
| AAACTG | (SEQ ID NO:39) |
| AAACCT | (SEQ ID NO:40) |
| ACACCG | (SEQ ID NO:41) |
| AAAGCC | (SEQ ID NO:42) |
| GAAGCCA | (SEQ ID NO:43) |
| AAAGACA | (SEQ ID NO:44) |
| AAAGCCT | (SEQ ID NO:45) |
| ACAGCCA | (SEQ ID NO:46) |
| AAAGACA | (SEQ ID NO:47) |
| AAATCCA | (SEQ ID NO:48) |
| AAAGCTA | (SEQ ID NO:49) |
| AAAGCAA | (SEQ ID NO:50) |
| AAAGCCC | (SEQ ID NO:51) |

Examples of ORE-like sequences include but are not limited to:

| | |
|---|---|
| CGGTTAGTA | (SEQ ID NO:52) |
| TGGTTGATG | (SEQ ID NO:53) |
| CGGTTATAA | (SEQ ID NO:54) |
| CGGTTTTTA | (SEQ ID NO:55) |
| GTTGTTGTC | (SEQ ID NO:56) |
| TGGTTGTGA | (SEQ ID NO:57) |
| AGGTTGTTC | (SEQ ID NO:58) |
| TGGTTGTGA | (SEQ ID NO:59) |
| TGGTTAATG | (SEQ ID NO:60) |
| TGGTTCTTC | (SEQ ID NO:61) |
| CGGTTATTT | (SEQ ID NO:62) |
| CGGTTTTTC | (SEQ ID NO:63) |
| TGGTTTTTG | (SEQ ID NO:64) |
| TGGTTGTAA | (SEQ ID NO:65) |
| TGGTTGATC | (SEQ ID NO:66) |

The present invention provides numerous compositions and methods using such compositions to effect gene expression. For example, a promoter sequence may be modified to delete that portion of the promoter 3' to the last repressing sequence (URS or URS-like sequence) and the truncated promoter together with its corresponding open reading frame (ORF) may be inserted back into a host cell. In the case of a *Candida* sp. CYP52 gene, described in detail in U.S. Pat. No. 6,331,420, all or a portion of a CYP52 gene promoter 3' to the last URS or URS-like sequence may be deleted and the truncated promoter together with its corresponding ORF inserted into a yeast host cell. Preferably, insertion is by homologous recombination. Alternatively, all or a portion of a CYP52 gene promoter 3' to the last URS or URS-like sequence may be deleted and the truncated promoter operably linked to coding sequence for a heterologous protein may be inserted into a yeast host cell. Preferably, insertion is by homologous recombination. Especially preferred sequences coding for heterologous proteins or corresponding reading frames include coding sequences for proteins of the omega oxidation pathway such as e.g. cytochrome P450 monooxygenase (CYP), NADPH cytochrome P450 oxidoreductase (CPR), cytochrome b5 (CYTb5), fatty alcohol oxidase (FAO), and aldehyde dehydrogenase. Coding sequences for CYP and CPR genes are disclosed in U.S. Pat. No. 6,331,420, which disclosure is incorporated by reference herein as if fully set forth. Coding sequence for a CTYb5 gene is disclosed in U.S. Pat. No. 6,503,734, which disclosure is incorporated by reference herein as if fully set forth. Coding sequences for proteins of the beta oxidation pathway may also be used e.g., POX4 or POX5, which coding sequences are known and available. Coding sequences for FAO genes are set forth in copending U.S. patent application Ser. No. 10,418,819.

In another aspect of the invention, one or more URS or URS-like sequences may be deleted from a native CYP52 gene promoter. In a preferred embodiment, all of the URS or URS-like sequences are deleted from a native CYP52 gene promoter.

When creating the modified promoters of the present invention by deleting any of the sequence motifs desribed herein, the deleted motif is preferably replaced with a nucleotide sequence of corresponding length. In this way, the binding site for an activating or repressing factor is disrupted while maintaining the spatial integrity of the promoter.

In yet another aspect of the invention, a UAS (including a UAS-like sequence) or ORE (including an ORE-like sequence) may be amplified in a promoter sequence and the modified promoter sequence operably linked either to its corresponding coding sequence or coding sequence for a heterologous protein. A subject sequence motif may be added to a promoter sequence of any target gene.

PCR may be used in order to introduce a subject sequence motif into any target gene. PCR primers can be made such that the sequence motif can be directly incorporated into a PCR product. This product can then be used in an additional PCR in order to generate a promoter comprising the additional sequence motif PCR may also be used to generate a promoter fragment which deletes a subject sequence motif. The resulting promoter is devoid of the subject sequence motif PCR technology is well known to those of skill in the art. Methodologies may be found in many texts such as e.g., *PCR: A Practical Approach*, M. J. McPherson, P. Quirke and G. R. Taylor, IRL Press at Oxford University Press, Oxford, England, 1991.

One method to effect deletion of a promoter motif of the present invention is as follows. Two complimentary oligonucleotides spanning the region of the promoter motif are designed and made such that the DNA sequence of the motif is absent and replaced with a random DNA sequence identical in length. Alternatively, one or more DNA base pairs are changed in order to disturb the effectiveness of the sequence motif. These oligonucleotides are then denatured and then re-annealed to generate a double stranded DNA molecule. This molecule is then subjected to PCR so as to amplify its number while incorporating DNA sequences complimentary to the native promoter at its flanking sequence. In this way, the native promoter motif is deleted and the oligonucleotide is inserted in a position as would be found in the native promoter. The modified PCR fragment comprising a native promoter sequence minus the subject motif is then fused in two separate steps by PCR to the native promoter sequence. The modified promoter can then be fused to a target ORF and introduced (transformed) into *Candida*. Preferably, introduction is by homologous recombination whereby the native promoter at its chromosomal locus is substituted with the modified promoter sequence.

Activating sequences may be amplified using well known procedures. For example, two complimentary oligonucleotides spanning the region of the promoter motif, e.g., ORE, are designed and made such that the DNA sequence of the motif is duplicated, yet spaced a given length from the resident ORE in the nucleotides or DNA base pairs. Alternatively, DNA base pairs may be changed in order to create an ORE motif in a region of DNA where such motif was not previously found. These oligonucleotides are then denatured and re-annealed to generate a double stranded DNA molecule. The molecule is then subjected to PCR in order to amplify its number while incorporating DNA sequence complimentary to the native promoter at its flanking sequence. In this way, the amplified sequence in inserted in a position as it would normally be found in the native promoter. This modified PCR fragment containing native promoter sequence plus the amplified motif is then fused in two separate steps by PCR to the native promoter sequence. The modified promoter can then be fused to a target ORF and then used to transform *Candida*. Preferably, introduction into *Candida* is by homologous recombination whereby the native promoter at its chromosomal locus is substituted with the modified promoter sequence.

In accordance with the present invention, it has been discovered that the best candidates for modifying promoters with the sequence motifs of the present invention include the *C. tropicalis* POX4 and CYP52A genes. Studies of the CYP52 genes from *Candida tropicalis* reveal that only CYP52A2A and CYP52A2B genes comprise an oleic acid response element. The *C. tropicalis* POX4 gene has two copies of this element in the upstream region, yet *C. tropicalis* POX5 and CPR genes have none. The POX4 gene has a TATA box at −68 to −66, and has an A at positions −1 and −3. Two ORE consensus sequences are located at −358 to −350 and −441 to −433. No URS sequences are found in the promoter region. The CYP52A2A gene promoter has a TATA box at positions −76 to −73 and has an A at positions −3 and −6. One ORE sequence appears at −969 to −961 and another ORE sequence appears at −946 to −938. There are several URS-like sequences between ORE and TATA.

For example, the POX4 promoter located on a 531 bp fragment can be truncated at the 5' end to delete about 100 bp in order to delete the first ORE. Alternatively, the POX4 promoter can be truncated by about 190 bp at the 5' end to delete both OREs. In another embodiment, either or both of the ORE sequences can be altered (substitution of one or more nucleotides) so that the ORE motif no longer functions. In yet another embodiment, the spacing between OREs may be altered. In still another embodiment, the spacing between ORE and TATA may be altered either by insertion or deletion of nucleotides.

With respect to a subject URS motif, a URS1 or URS1-like sequence or URS2 or URS2-like sequence may be inserted into the POX4 promoter region. Alternatively, existing sequence may be converted to a URS or URS-like sequence by changing a few bases in the POX4 promoter region. Various combinations of URS1 and URS2 may be inserted into the POX4 promoter region. Spacing between/among URSs can also be changed. The position between the ORE and URSs may be altered by insertion or deletion of sequence. The position of one or more URSs may be changed relative to the TATA box.

The CYP52A2A/B promoter may also be used as a template for promoter alteration. For example, the promoter may be truncated systematically from the 5' end to ascertain the up-regulating and down-regulating regions. With respect to an ORE, the ORE or ORE-like sequence can be altered so that it no longer functions as an ORE or ORE-like sequence. An ORE-like sequence may be changed to an ORE. The nucleotide sequence between the ORE and ORE-like sequences may be altered. In yet another embodiment, the spacing between the ORE and ORE-like sequences may be changed. In still another embodiment, the ORE or ORE-like sequence may be replaced with an ORE or ORE-like sequence from the POX4 promoter.

With respect to a URS and URS-like sequences, individual URS-like sequences may be altered to non-URS and/or non-UAS-like sequences. Alternatively, a URS-like sequence may be altered to become a URS sequence. Similarly, a UAS-like sequence may be altered to become a UAS sequence. In still another embodiment of the invention, combinations of URS-like sequences may be altered to URS or non-URS sequences. In yet another embodiment of the present invention, the spacing among ORE/ORE-like, URS/URS-like sequences, UAS/UAS-like sequences and the TATA box may be altered.

The CYP52A1A promoter likely comprises unique promoter motifs since the mRNA is primarily induced by alkane. The present invention contemplates use of such promoter motifs as described hereinabove for the URS, URA, ORE and URS-like, URA-like, and ORE-like sequences.

A subject modified promoter or modified promoter/ORF fusion construct may then be utilized to create a DNA integration vector for transformation into any suitable host cells. For example, suitable yeast host cells for use in accordance with the present invention include, but are not limited to, *Yarrowia, Bebaromyces, Saccharomyces, Schizosaccharomyces,* and *Pichia* and more preferably those of the *Candida* genus. Preferred species of *Candida* are *tropicalis, maltosa, apicola, paratropicalis, albicans, cloacae, guillermondii, intermedia, lipolytica, parapsilosis* and *zeylenoides*. Most preferably, *Candida tropicalis* is the host cell.

The modified promoter constructs described herein may be cloned and expressed in suitable expression vectors. Examples include, but are not limited to vectors such as plasmids, phagemids, phages or cosmids, yeast episomal plasmids, yeast artificial chromosomes, and yeast replicative plasmids. Host cells may also be transformed by introducing into a cell a linear DNA vector(s) containing the desired gene sequence. Such linear DNA may be advantageous when it is desirable to avoid introduction of non-native (foreign) DNA into the cell. For example, DNA consisting of a desired target gene(s) flanked by DNA sequences which are native to the cell can be introduced into the cell by methods such as, but not limited to electroporation, lithium acetate transformation, and spheroplasting. Flanking DNA sequences can include selectable markers and/or other tools for genetic engineering. Yeast cells may be transformed with any of the expression vectors described herein. The term "expression vector" is used broadly herein and is intended to encompass any medium which includes nucleic acid and which can be used to transform a target cell. Expression vectors thus encompass all the examples of vectors listed herein including, e.g., integration vectors.

In a preferred embodiment, a DNA construct is used to transform a yeast cell, e.g., a cell of Candida sp., to obtain modulated expression therein of a protein, e.g., a protein of the omega or beta oxidation pathway in yeast. The DNA construct comprises a promoter modified by substitution, addition, deletion, or changes in spacing between or among one or more sequences motifs hereinbefore described, operably linked to DNA coding for a protein (ORF), to enable expression thereof in the yeast cell.

The present invention is also directed to a method for modulating expression of a protein in a yeast cell. The method comprises isolating a promoter which functions in a yeast cell, modifying the promoter by the addition or deletion of one or more subject sequence motifs, operably linking the modified promoter with a coding sequence (ORF), transforming a yeast cell with the modified promoter operably linked to the coding sequence, and growing the yeast under conditions favorable for expression of the coding sequence under the control of the modified promoter. Preferably, the method is directed to a method for modulating expression of a protein of the beta or omega oxidation pathway in yeast. Such method comprises: isolating a promoter which functions in a yeast cell, modifying the promoter by the addition or deletion of one or more subject sequence motifs, operably linking the modified promoter with a coding sequence (ORF) for a protein of the omega or beta oxidation pathway, transforming a yeast cell with the modified promoter operably linked to the coding sequence, and growing the yeast under conditions favorable for expression of the coding sequence under the control of the modified promoter. Preferably, the yeast is Candida sp.

The yeast cells transformed with one of the aforementioned vectors, may be cultured in media containing an organic substrate, to provide modulated expression of a protein. Culturing the yeast, i.e., fermenting the yeast, may be accomplished by procedures well known in the art as described, e.g., in aforesaid U.S. Pat. No. 5,254,466, which disclosure is incorporated by reference herein as if fully set forth.

In any of the methods hereinbefore described, in addition to the promoter being modified by the addition or deletion of one or more subject sequence motifs, the promoter may also be modified by substitution of a sequence motif with other nucleotide sequences or by changes in spacing between or among the subject sequence motifs and the TATA box.

In a preferred embodiment, the modified promoter/ORF construct is used to transform a yeast cell, e.g., a cell of Candida sp., to obtain modulated expression therein of a protein, e.g., a CYP or NCP protein or any other protein of the beta or omega oxidation pathway.

The following examples further illustrate the invention.

EXAMPLE 1

A detailed sequence analysis of the promoter and upstream regulatory regions was performed on CYP and CPR genes. A direct sequence analysis was performed by comparison of all the upstream regions using the Clustal G algorithm and a search for consensus sequences, direct repeats, and palindromes. Consensus sequences were derived from two sources, previous analysis done in S. cerevisiae and by looking for novel repeated motifs found in multiple CYP and CPR genes.

The Genbank CYP and CPR genes were harvested using the BLAST tool found at the NCBI website. Saccharomyces cerevisiae promoter consensus sequences were found at the Saccharomyces Genome Database. Sequence analysis was performed using the following sequence analysis software: (i) DAMBE (Data analysis and Molecular Biology in Evolution), version 3.7.49, written by Xuhua Xia; (ii) Clustal G, version 1.0, Thompson J. D. et al., (1997) "The Clustal X windows interface; flexible strategies for multiple sequence alignment aided by quality analysis tools." Nucleic Acids Res. 24: 4876-482; (III) GeneDoc: Multiple sequence alignment editor and Shading utility, version 1.1004, written by Karl B. Nicholas and Hugh B. Nicholas.

In order to identify essential regulatory regions, the TATA box for each of the genes was located for each of the genes except CYP52A4A and CPRB. Sequences that were present upstream from the coding sequence in a multiple of CYP genes were identified as consensus sequences. In addition, sequences that have been previously identified as regulatory elements in S. cerevisiae were also identified in the promoter regions of the CYP genes.

Clustal analysis of the available upstream sequences from all the genes in the study revealed a novel consensus sequence (CACACCA) [Consensus sequence 1] (SEQ ID NO:67), was found upstream of all the CYP and CPR genes. Consensus sequence 2 (CUCUCYMMCA) (SEQ ID NO:68) was found upstream all of the genes except CYP52A8A, CYP52A8B and the CPR genes. It is therefore likely that these sequences have a regulatory function. Some genes had multiple copies of consensus sequence 1. Interestingly, consensus sequence 1 was always found within 100 bps of the putative TATA box. When present, consensus sequence 2 was located just upstream of consensus 1. A third consensus sequence was also identified. This sequence was found 900 to 1200 bases upstream of the ATG codon. The sequence GGUg/uUCAAGMMA (SEQ ID NO:69) (wherein Y is U or C; M is A or C), is related to the reverse complement of the consensus sequence 1.

In addition to the sequences mentioned hereinabove, a binding site for GCR1, a factor required for expression of many glycolytic enzymes was found in all the upstream regions except CYP52a3b. The binding site for ADR1, the trans-acting factor for the alcohol dehydrogenase genes, was found upstream of all the genes except CYP52a3ab, CYP52a8a, and CYP52a4a. The C. albicans analog to Adr1 has been identified (Candida albicans genome project. See http://www.sequence.stanford.edu/group/candida; http://alces.med.umn.edu/bin/genelist?genes). Both of these binding sites are found upstream of the S. cerevisiae ERG11 gene (cytochrome p450). In addition, sites previously found as repressible regulatory elements in S. cerevisiae were also identified. The GC/FAR factor binds to the sequence GGGCCC (SEQ ID NO:70). This site was characterized initially for the yeast ORE1 gene (fatty acid metabolism). This site was found upstream of the CYP52A5A and CYP52A5B genes. Other S. cerevisiae regulatory elements were also identified.

Upstream Regulatory Regions of Known CYP Genes from Different Yeast Species

```
URS1-AAACGA (SEQ. ID. NO.1)

URS2-AAACCG (SEQ. ID. NO.2)

AAAGCCA (SEQ. ID. NO.3)
``` hypoxic operator-ATTGTTCTC

ORE-c/tGGTTa/gTTc/a/g (SEQ. ID. NO.4)

Exact matches are underlined; one based mismatches are shown in bold but are not underlined. For USR1 and 2 one base mismatches could be for either operator element. All sequences end at the ATG start codon.

```
>D00481 52a03 C. maltosa; 1020 nt
ATGCATGAACAGGATTTAATCCCAAGAAAAAAGTCTATTTTCTATTTTCACAAGGAAACT      60 (SEQ ID NO: 71)

GGAAAAACCTTTTTGTGTTTTGAAGTAGCTCCGTAATAACCTGTAAAAAAATAAATTTTG     120

AAGATTTGACTTGCTGATGAAAATGCTATCAGTGTAGCTCTAGACTTGATACTAGACTAT     180

GATGGCAACACATGGTGGTCAACGTGCAAGACATCACCCAATGAGAAGACTGCTAACCAG     240

AAAAAAAGGGGACAAAAGAAAAACTCGAGAGAAAAAGTCAAATTGGTGTAAAATTGGCT      300

ATTTTTGGTACTTTCCTAATGGGGAAATTAATTGTTTAAAATTCCAGTTTTTCCAGAGTT     360

AAGATTTCGACCAATTATTTTTAATCCATATGATCTTCATCATTATCAACTTGTGAAAAA     420

TAATAATCGAGGTACGTTTAATACGAGATATTAGTCTACGGCTATGAATGTTGGATATAC     480

TTCATTGACGATCAGAAGCTTGATTGGTTATTCAGGTGCATGTGTGGATATAAACCCAAC     540

AAATTATCTAGCAACTGTGCCTTCCCCACATTGGTCAAAGAAACCCTAAAGCAAATTAAA     600

ATCTGGATAAATAAATCATTCATTTCACATTTTCCGGTTAGTATAAGGTTTTTTAAATTT     660

TTTTTTACAGTTTAGCCCTTTCAATTACCAAATACGGTAACAATGTGCTTTGTAACATGC     720

AGGGGATTTTCTCCGTTGCTGTTTTCTCCACATGCTTTTAATGTGTAATAAATTAAAAAA     780

ATTACAAAGAAAAACCGGCATATAAGCATCGGAGTTTACATTGTTAACTAACTGCAAAAT     840

GGCGATCTTTCAAATCAACAAAATTTAAAAAAACCCCAAAAAAAAAGTATCATATAAATT     900

AAACTCAAAATCCTTTTGATTGCATAAAATTTTTAAATCTCTTCTTTTTTTTCTTTTTTA     960

CTTTCTTATCTATTCTATTCTTTTTTTATATATCTAATTCATTTATAACATCTGGTCATG    1020

>D01168 52A03 C. maltosa; 251 nt
ATGCATTTGATGTGAAATAAATTAAAAAATTACAAAGAAAATCCTGCATGTAAATATCGG      60 (SEQ ID NO: 72)

ACTTTACATTGTTAACTAACTGCAAAATGTATACTAGATGTTTCAAATCAACAAAATTAA     120

AAAAACCCCAAAAAAAGTATCCTATAAATTAAACTCAAAATCCTTCTGATTTTTTTATTT     180

TTTTTTTGTTTGTTTTCTTATCTAGTCTTTTTTTTTCTCTATATCTAATTTATTTATAAC     240

ATCTGGTCATG

>D12717 52A09 C. maltosa; 742 nt
AAGCTTCACATGGATCAATTGCGTTTGTCACATGTGGTCATCCAGCTATGGTTGATGAGG      60 (SEQ ID NO: 73)

TTAGATATTTTACTTGTAAGAATATTAACAACCCAGAAAAGAAAAGAGTTGATTTCTTTG     120

AACAAGTGCAAGTCTGGGCTTAGACGTTTATTTTTGTTTTTGTTGAGTGGTAATACATAT     180

TCTTCGTATCTATGAAGATTTTTCACACGCGGATAGTAATTGTACTAGCCGCTTCTTTAA     240

GTAACTGATTTACCCAACAAGTACATGGTAATACAAACTCTCACTCACTAGACTTCGCTT     300

CTAGTTGCTTCAAATTAGACGGTTATAATGTATGCCAAGGTTTTGTGTAATTTCACGGTG     360

ATTAACCTTTTCCCCTTTTTATACTCCTCATTATCCACGATGTAATCTGATCTATGAACG     420

TGATAAGTAACATTACTTAGTCATTAAGTATGGCCAATTCAGTTATACATATTAGTAATG     480

CTCCACATCCATTGTATTCATATGTAATGCCAAATATCACATTCATTTACACAGAATCGG     540

TTTTGTTAAATACTCCGCTATTGTACAGCAACAATAGGATTATGTACAGAATGAAAAACA     600
```

```
AAAGGCGGAGAAATTCGACGGAAAAATTTATTATTTACAAATCGTATTCCCGCATTATCT        660

ATAAAACAGATTCAAAATAATCTAGATCTCTTTTTTTTGCTTCCTTTTATTTCTTTTTAA        720

ATAAGATTAAACTAAAAATATG

D12719 52A10 C. maltosa; 756 nt
CAGTGAGCGCAACGCAATTAATGTGAGTTAGCTCACTCATTAGGCACCCCAGGCTTTACA         60 (SEQ ID NO: 74)

CTTTATGCTTCCGGCTCGTATGTTGTGTGGAATTGTGAGCGGATAACAATTTCACACAGG        120

AAACAGCTATGACATGATTACGAATTCCACCTATCAAAATTCACATCGATAATCGATGTG        180

TGATTATTGGTCAAATTAATTTATTACTTAATCCCTTGGAAAAAAGCACAAATCAAGACC        240

CGTCTTCTCGTAATTACATTAATTATATGAAATCATCCCCTTTTAATTTTTTATTTTTTT        300

ATTTTTTTTGTCCCTGTTCCAAAGAATGCTAACTGTGGAGATATCCAACGTCCAATTACC        360

ATCAATAGATCCGCTTTAATTGATAATGATGGAGATATGAAATTACCGATTCCAGTCAAT        420

AGGTCCGCTTCTATTGATAATGATGGAGATATGAAATTACCGATTCCAATCAATAGGTCC        480

GCATTAATCAAGTAAATTACGTCAGAGATATATCAATTAACTTATATACTTGAGCAAAAC        540

ATGTCAATCTTCTAACAATTACATAACCCGATTTATTCATAAACAAAAAAACAAACGGAG        600

AAAAAAAAATAAAACAAACGTTAAACATCGTTTTACGTCCGTCTTTTCACACCTGATCAA        660

GTTACTTTTTTTGCAATATATAAACCCTTCGATTTCTCTTCAGTAAAGTATAATTTTTA        720

TTTTTCATTTTATTTTAAACTCTATCAATAATTATG

>D12719 52A10 second transcript; 821 nt
AGTATCCATAATTCAAAGTTTAGTTTGAGATACATATAAATTTAAACTTGTTGTATTTTT       2760 (SEQ ID NO: 75)

TTAAGAGTTTGATGTTGAATGCATTGAACAAAAGTTTTTATAGTTTAGCTTTGGATTTAA       2820

GTACCCCTTGAATCACGTTTTTTGTTATTTGATTCACCTAGTTTACGCACGATGTATCAG       2880

AATTAGCAAGTTTGAGGTTACTTGGAAGTGGTGGTCAACTCAGTAACCAATACATATGAC       2940

CAGTAGATATATTCTTATAAACTAATACCCGTGATTTAACTTTATCATTCGTAATTACAA       3000

AGCTAGAAACCATCAAATTTCACCTATGTATTCTTTCATTGATAATCAATGGTTGATTAT       3060

TGGACAAATTAAACTCGGAAAATAACACAAAACAGGAGACAATTATTCCTAATTACATT       3120

AATTATATAAATTCCCCCTTTTATTTTATTTTGTCCTTTTGCATTGATAACTGTCCAGAT       3180

AGCTACCAATGCAGTTCAATAGGTCCGATTATATAGATTACGTCAGATATACATCAATTC       3240

GCAACATTAATTCATATCAAAACCATTATATTTGTAGGAATTACATAATCCAATTTATTT       3300

ATAAACAAACGAACGGACAAAAAAAAAAATCTTTAAAACATTCTCCTCCTCCTTCCTTCT       3360

TTTCATTGTTAAACATGAATTTTTCCCCTTTGTATCATCTATTTTCACCACACACACCAA       3420

ATTAAGTAAATTTTTTAATAATATATAAATCCTTCTATTTCTTTCTTTCCCTAAAAAAA       4480

AAATATTCTCTTTTTCTTCAGTCCATCAATCAACTATCATG

D>12718 52c C. maltosa; 150 nt
ATATGAAATTATTTAGATATTAACCCCTCGATCTTTTCTAATAAAAAATCACACATGCAA        60 (SEQ ID NO: 76)

ATATCAAACCAACCAATATAAATAGGATGAAATCAAATAAATGAATGATTTTTGTTTTTT        120

ATTTTGATGTGTAAATCCTAAACAAACATG

D12716 52d C. maltosa; 771 nt
AACTCTCTTTACCATCCCCAATTATATGATGACACATCTGCGTCAACGACCGAATGTAGT        60 (SEQ ID NO: 77)

TCTGCGATTCCGGAGTAAACTTAATATCAAGACCTAAGAAAATCATCCGGTCATTCTGTC        120

CTCGCCTCAACTTGAAATGATCCTCCAACTCAAATCGAAGCACTTTCCTCCTTTTATTCA        180

AAATCTTGGCAATCCCTTTATCCCCTCCAACTTCAGCCACTAACGATTCCGGAACTGGCA        240

ATTTACGTATATCGTCAATCAACCCCGTCGCCACCGTGTCAAACCTTTCATCGCTCGGTA        300
```

-continued

```
TCATTGTATTGGGGAAAAGTGTAATATGTTGTTTAATATCTCGAATTCGATCCTTATGTG      360

GTGAAACAAACCTATAGTTTTGTACAAGTTGTGGGATAAGTGCAAGGGCATGCCGACACC      420

CTTTTTCTATTTTGCTGACTGTTGTAATCGACGGATTCGATGGTAAAAAACAATACGTGG      480

CAAACCCTTTGAACCTCATATTTTGTTGATATTTCTGCAGATATATTTCTATAGTAGGGA      540

GTGGAACTTGTTCTTCTTCTTGTTCGGTATCTGACTCGGTGTCAGAACTGTATTGTTTGA      600

TTAATTCCATCTCTAACTTGAATCTACAAAAAAAAAAAAAAAGAAAACGAAAAAAAACTT      660

CGATCTCAGCGCTCGGCCGAAAGAACATAACTGGACTACCGTTTTTGATATGTTTTAGCA      720

ACTCCATCTTCCTTTCTTTTTCTTTTTGGTAATTTGTTGCTAGTTAATG

>X76225 52E01 C. apicola; 837 nt
GAGCTCGGTACCCGGGGATCTATTCCTCGTACTATGCTACGAATTTAGCTGCCTCTTCTA      60  (SEQ ID NO: 78)

TTCAGGTATTTATTGACCTCTTCCTGAGCAATAACAAACTGCTCATCTTAGATCACCAGC     120

GGCCCGGATGCCCTGTCTAACAATTAATCTTCCGGCAAACGCAACCCTCTGCTTCTGGTT     180

CGGCAAATTCCTCAAATCGAGCTCGGGGCGATGGTGGATACACGACCCCTCTAAATCCTC     240

TTCCAGGGTCAAATCCAAGAATTTCTCCCAATCGAATTTCTCTATTTCCAACGCTTTTAG     300

CTCCTCTACGGCACGGTCCAACCGGACGCGCTCAAAGCCGTCCCGAGAAAGTTTCCATGA     360

TACTGTTTACTAACCCATGATACTGCTTGTCTCTGAGAGGTACAGCCGGTGACAGTCCCG     420

AGGAGATTTCAAGGCTATAACAGGTCTGTGGTACCCTTTAACGCTCTGGGCCATCTCACG     480

AAAAAATTCCAACTACTTCAATCGCCGTCGCTTCCAGTTGTTGCAGTGCTTGAGAGTCAA     540

CTTGGTATATAATCACATGCTCTGTGTTCACATGGTGTTGCATTGCATTTCATAGTGGGG     600

TATTTGACACGTGCTCGATCACATGTAACTCCTAACGGGAAAACCGTTATTCGCTCGCAG     660

AAGCTAATTCCGGGGAATATAAATATATAGAGCTTAATTGTAGATTGTGAGTGGGATCCA     720

GATAGAAAAGAGAAATTTGACGATCACTTACATCACGCGCAGAGCTGTTGTCGACAAGTA     780

ATCCTCTTACTAAATCATCAATTCTGATAGTTCTCAAACTGTTCAACACTTCCCATG

>X87640 52E02 C. apicola; 400 nt
ATAAGTTTCTAATTAGTTTGAACCGCTAACAGTTTCAACATTCGCGGGATTCGGGCGCTC      60  (SEQ ID NO: 79)

TTTCCGTGCTTCACTCCGGTCAATCGCAGTGTGCTACATGCTTGTGGGAATTCAGACCGC     120

ATCGAAATAGGGTAGTAACACGATTATCATGTGACTATGCACATGTGACTTTTATTGCGG     180

GGTATGTACGTTATCGTCCCAGAAACCCAGTTCCGACATTTGATAATCAATATATAAAGC     240

TAACTTGCGGTTTTTAGATTGAATAGAGGTCTGCTGGTGCTATTCAGATAGAATAGGAAA     300

TTTTTCACAACAAGGACACAACACATTCAAATCAATTGTTAACAAGCGTTACTGTTGTTA     360

GACCGTCATTCCCAGAGTGTCTAATCCAACACATCCCATG

>AB010388 52F01 Yarrowia lipolytica 1645 nt
AGATCTGTGCGCCTCTACAGACCCATGTGGATCATGAGGATGAGTCACCTGTTGGAAAAT      60  (SEQ ID NO: 80)

GATGCTCTATAGGTTCACCAACGATTTAGTCTTGACTACTGGTAGGAAAACAAGAGTGGA     120

TTCGTCCATCTAATGACTACAAGTATTTGCGTCGCCATACGGAGAAACCACAGTTTCAGA     180

TGACGCGGAGTAGTGGGCGGTCTGAGTTTGGCTTCCGCACAGGATCGTCCAGTTACACT     240

TTCACGTTCTTCCTTTGCATGGAATTTTCTTTTAGCTTTACTCAACAATTTTGGACTGTG     300

TAGTGGGTGGACAACAATGGAGAGAATGAGACCCAGAAAGTCGTATAGCGACACCCAAGA     360

CCGACCAGTAGCTCCCATGTAAAATCTCTGACCCAAACTCCTGTCAATTTCCTTCATTAC     420

TCCATGCTAAAACGCTAGCTTCGGTGTTCGTTTTGCTTTTTTGATTTTGGCTTAGATTTG     480

GCCCAATGCTTAGCGAAACGCGGGGTTCCCAAACAAGACAGTAATACACTGGGGAGAGGA     540
```

-continued

```
CAAAAATCCTGACGGAGCAAAGAGAAGCCAGCTCAGAAGCTATTGTGAGGTTCCAAAGAG      600
ACCACATGCTGCAGGGGAGAGGTGGGGGAGCCCGCAGAGAGCACAGAAGTCACATCTGGG      660
GTCTTTACAAACAAACAGGGGGTACCTGAATCCACTGACTCTGGGGTATGTCCGGGGTAT      720
GCAGCCCACAGGTCAGTTTAGAACGCCGTTTCAAACGCCTGCAAAACGACTTTTAGAGCC      780
ACGAGAAGACTGACTTGATACGCAACTGGAGAAACAAGAAACAAATACATGTATGTACTG      840
CTCAAATATCGACATTGCACAGATGTTTCACCCTTCATACAACACAGGTATACACGTTCG      900
CAGACGCTAATAACCAGCTCTGCGATCAACTCTAACCTTGTGAGTAACCCAGCAAATGAC      960
GATTGCGGAGAAGCTCCAGCGGGTGTCACGAACGGTGGAGGTGGAAAATAATGGTGGTTT     1020
AAAGACATAAAATTGGTAGCAACAGTGATGAGGACACACTCTAGGACGTCTGGTACCACA     1080
AGGAGGGGCCAACTGTCGCTGTCATCGCTGTCTCCTGGACAGCAGAGCTAACTGTTGTAC     1140
TCCAGTGACCAACCAAAATTCTTCTAATGTTGCGGCTCAAGGTCTGTCCCCACAACTGTT     1200
GAAAGCCTAAGCGTCATGGTAACAACGAGGAACAAGGGCTTTTCGAACCTTGTGCGATGA     1260
CAACAGCATGTGAATAAGTGTTAGTGGGGAAGATTCAAGACAGCAGAAAGTTAGCGGGTG     1320
TAAGGGGGGGAGGACCAGAGGGGGTGTTAACTCATCAGAACCTTTCCTGCCGAGATGTCA     1380
GCAATCAATTCGCCTTCCATACATCTTATGATGCTATAGATTCCAGTTCTGAGGTGTTCC     1440
TGGTATGTTTTCATCTTCTTTCATTCCATTCGAGATCCCTCAAGAGTGCATGTAAACTGA     1500
AACCTTATGCCAAACTGAGCGATCGTGAATATGAAAAGTCTGGGAAAGCGTCAATTCAA     1560
AAAAGCGAACAAAAAAAGCACAGAGGTATATATATAGGTGACAGCACCAAACCATAGGTC     1620
CTCCCCAGAATACTCCTGCACTATG

>AB010389 52F02 Yarrowia lipolytica; 1819 nt
GTCGACACGCTTGCTGAGGTTCGCGATGGTTTCGTGCTGGGCCGACACCAACTGGTGCAA       60   (SEQ ID NO: 81)
CTTTTCAAACTCCCCAGCCTGATGTGTCTTGAAAGACTCATTTGACTGCTTGAGCTCGTC      120
TAAGGCTGAGCGGAATTCCTTGGTATTAACCGCGGTAGCAGAGTAGTGGTGATCTCCTGG      180
TGGGAGAGCGTCAAGGCGTCCATCTTCGCGGTGAGAGCCTGGAACTCGTCTTTTGTTACT      240
TTCGACATGGTGAAAACGAAAGAACGGAAAGGGAAGTAAAATACGCTGGTACGACAGTAA      300
AGGCACAATAAATCGGCAGGCTATCACTCGAAACAAAAACGAGGTGTCGTCCACCAGAT      360
GTGAGAAAATAAAGTGCTTTGTGCGTACCAGGGATAGGGTAGGTAGTGAAATCTGAGTTA      420
GTACATCAACTCTAGACGATGGGCGTCGCCTGTGTAGAAGAACAATAACTCACCCGGTAA      480
CTAACACTATTTCTCGGTGGTCAATGCGTCAGAAGATATCAAGACGGTCCGTTTTGCGTT      540
TAAGCCGAGTGAATGTTGCCTGCCGTTAGTAAATTTATTATGAAAAACCCCACTATGAAT      600
ACATCAGCCTATACTGATATACCAAGAAGTGCAAGGGAGGTGGTCCTGTTCCACCTGAAC      660
GCGGTTCCCGACAGGCGGCGGTACTGAAGGGCTTTGTGAGAGAGGTAACGCCGATTTCTC      720
TCTGCAGTCGTAAGCCCAGGTGGTGTGTCCGAGGCAGTATCGCTTTCCCAACTCTAGTAA      780
CCTCGGTAGTGTGAGACACACTACCCCTAACGGTAGGACAGCCGGACGACCATGGCGCAG      840
CAATTGGCGAACGCTGTTATAAAACAATTCACTTACGTGCAATGAAAGTTGTTTGGGCAA      900
TAAACAATAAATGTATTAGAGCCAGACGATAGACAACAATCCAGCAGATGATGAGCAGGA      960
AAATTGAGTAAGATCGACGTGGCAAGAAGAGTTACAGTTACGCAGAGTTAATAAGGTGTT     1020
GGGAGATTAGAGTTACCCTGTCGGATGACTAACTCTCCAGAGCGAGTGTTACACATGGAA     1080
CCTTTGCTATTTCGGGGATAACCCCCTTTGCCATTGCACGATGGACGTGGCAAAAGAAAG     1140
ATCGCCCTGCGGGGATACTTATCATGTGGTCACATGCTGTGATTAGAAATAAAGAAAAAG     1200
GTGCTTTTTTGGCGCTGTGATTAACATCTCGTCTGCCGTGCTCTACTAGTCGCAATAGCA     1260
```

-continued

```
AAAACTCGCTTAATAGTGTGCATAGTGCGGGGTAGCAGGATACTGAACTACAGTACGATT    1320
TGCTTGCTACTGCTTGTAGCAATTACCTTTACTGTAGGGACCACACCTCCTGGTTTCAAT    1380
GTCTTTCCTCGCCTCGACAAAGCAAAACTGTCACCCAATCACACCTTGTTCATATTCATT    1440
AGTGCATCCGTTAACCTTGACATGACACTTCTCATACTAGTGATAGGGCTGTAGTTGAGA    1500
CAAGTTGATTCACACGGATACAGACAAAGCCTCAGAGAGCAAATGTTATATACTCAGGGA    1560
CCGACCAATCAAAAAAACACACTCCTAATAACCACCATTTCCATCTACGCGTACTCACTC    1620
TGTCAGCTGCCCCACATTGCCCAATGCACAATGCACAATGATGTGTGCAAACAACGCAAT    1680
CAAAAGTCTATGCATGCTGACCAAACTCTGATCACCAAGTTGCGAACATGAAAAAGAAGA    1740
CCTGTGTATATATAAGTAAGGGGGAGAGCCCTAACTAGATCTTTCGAAAACCCCCCGACC    1800
TTCACCTTCCACAACCATG
```

>AB010390 52f03 *Yarrowia lipolytica*; 1036 nt    (SEQ ID NO: 82)
```
CTGCAGCGGCGAGACCGGTTCTGGGCCGACTACGACGTGCCTGGAGGGACGCTCCGGGAG      60
AATCTCTTTGGACGGGCCAAGATCTTCCCCGACCACCCTGCCGGACAGTACAAGTGGGAA     120
GAGGGGGAGTTTCCCTTGACCAAGAGTGACAAGAGTGAGAACGGCAATGGAGTCAATGGA     180
GATGAGCCCGCTACTAAGAAACAAAAAATCTGAACAAGAGCCGGTTTTAGTACGATACAA     240
GAGCCGGTACGTGGACATGCAGCTGCTTTTCGAACATGAAGGGAGCACGACCCCACGTAT     300
CAGTATTATGCAAGGGACCAGAAGTGGCCTCGGCAAAAGATTGGCCTCGGTCAACAAAAG     360
GTCATCATATCCGTCTCCGCATCCGTCTGTACGTGAATTATGTTACTTGTATCTTTACTG     420
TACTGGTTTGGAGCTACGTCGCCAACTAATGCCAACCAGTCCTGTGGTGTGTCTATAGGT     480
ATGTAATACAAGTACGAGTAAATGTATTGTACTGGTGCAGCACAGTAGATGACGGAGACG     540
ATGAATCGGTCACCACCCACAAACATTGCCTCCAAACACCGTTATATTGTCTTACTGTCG     600
TGGCTGAGACAGACTCCTCGGGGCCTTGTAAGAGGGGGAATGTGTGAGACAGATGCCCAC     660
AAGTGACCATGCATTTTGTGGGCAGGAGAAAACCAATGTTTGTGGGGATAGAACCCAT      720
CAAATGAATCTAAATGAACTCTCCCAAAATGAACCACTCTCTTCCTCCAATCAAAGCCCT     780
GCGAAATGTCCTCCGTCTGTTTCTCGGACCCTTAGCCGTACGACGCCATATTACGATAGC     840
CCGCCACCTTAATGCGTTTAACTTGCATGCATGCGTCTGCATACAGCTGCATCTGTCATA     900
TATGCACCATTTCCCCACACAACTGAAGTTTATATATATATACTGTAAGGACTCCTGAAG     960
TGGCACGAACACACCTGATCACAGCAACATTACAGTACACTACTCTGCTCGTATTTTACA    1020
ATACTGGACGAAAATG
```

>AB010391 52F04 *Yarrowia. lipolytica*; 1683 nt    (SEQ ID NO: 83)
```
AAGCTTTCCTGTAAGCGTCACCGATCTTGGCTGGGCTCTTGGCCGCAGTTCTGATTGGAC      60
GTGATAGGAAGCATCTCATTAGCGTCGATAAGATAAGGTGGAGAGTGTGGCTTGAGTGTG     120
ACATTGACGTGGATAACAAGACGGAAAAGTACGAGAAGGGGTCTGTCAGGGCAGCCATTG     180
GTTGGATAAACCTGATATCCCGTTCTTCTTGGTCTGGAGGGGAATAAAATGGTGTTGTAT     240
TTAGAAATTGATGCTTGTCTTACTCCGGCATCGGCGAGATTCGGATATTGGGGTGAGGGT     300
GAACAACAGCCTGTACTCAATGAAATTATCGGCACTAAATGTAAGTACAGTACATACCTC     360
ATTTTTCGTACAGTACTTACATGATCATGGGTGGAAGTGTTAATCAAGCTACAGTATAAT     420
GTGATATCTTTTGGTTTGGCTTTGCTTCTTGCGATCCATTACATCGCAATCGACTATGAA     480
TGATTTCGAGTTTGCCAGAAACATAACCAAGAGAACTATGAACTTCATACTGTAGTGACA     540
TAAGTACAGGAAGGCATATTTAGATACTCAGATTGAGCTCTTCTGTTTCTACTGAATTGT     600
TTCTCATTTATTGGTCATTGTTGGTATTTTTTAGCCGAAAGTATGTGTGAAATGCTAAA     660
```

-continued

```
ATACCTCTCCAAAGAGAAGCCACCTGATATTGATTTCACGCAGTCTCTTTATGAAACAAA      720
TTCTTCACAAAGACTCTTGATACTACAAACACCTCTCAGATACCTCTCAACCACCAGTGT      780
TGCTCATGCTGAAGTAGTGATGGCGAATTGTTGATTCCATCTTCCCGACAATCACAGTTC      840
CACAACCACATTCCACAACTCTCTAATACAGTAATAGCCTTTAATGGGCTGTTGTTCCTG      900
AGCCTCTCACCGCCCTGGACCGTTTCCCCCCGTTTGTAGCTCGCTTTTACTGAGACTGTT      960
TCGTCTAAAGCCTTTTCAAATTTATGATTATTCGTCTCGGTCCAACCTTGTGTAAATAGT     1020
GTGGAGAAATGATGCTCTATCGGTGCGCATCTGTGCATGATTACATGACCATTTGAGCTG     1080
GATATCTCGTGTTTGGTAATGAATCAACAGAAAAGTTTTAAATCATTGGAACACACTACA     1140
GTAACCCATGCCACATAAAACGGCACCGCTCGTATATAAAGAATCGTCCCACTAGCCTT      1200
AGGGCTGCCTGGATTCCTTCTCATCACTTGTCGCTTTTAATTGGTAAACAGCGACACTCT     1260
ATTGGGAGCGTGGGAGAGAAGTAAGCAACATGAAGCCTATATACGAGTATGCAAAGTGGG     1320
GCCGTAAGCAAGGACGGAAATGTTGATTTTCACAGACAGGTTGGGGGTTGTTGTCAGTTT     1380
TTATTGACGATTATTGATAAGACAGATCGAGGAGAGATATAAACCCTTTCACCCCCCCTC     1440
CCAATTGCCCTCGAAGCTGCTCGATCAACTCCTTTCACCACCTCTCTTCGTCCCCATCTT     1500
ATGTTTAACTTTCACGTTCCTCAATGCACCCCAACCAAACATGGATTTGGATTCAAGCAG     1560
GTTATATAGTCAGGGCCTTGCTCTGATTCCCTTTGCACCTCATATTCCTCTCACGCCATG     1620
TTGACCAATCTTACGATCGTGCTGATCACCCTTCTGGTGACATATACGGTGCTGACCCGT     1680
ACG
```

>AB010392 52F05 *Yarrowia lipolytica*; 1066 nt

```
GTAGACCTCGCAATTCAATCTTCAATCTTACGACCACTTTCACCACCCAAAACTACGTGC       60   (SEQ ID NO: 84)
CTCCAAATATTTTCCTCACCGAGACCGAAGTGCGAGCCGTCGCGTATTTGGACATTTCAG      120
CAAACTCTACAGTACCTTCGCCACTGCTCTACTTATAAGTAAATTCTCTTCTATGTTTAT      180
ATTCACTGCATAACTACAAGCATCGTCATACAAGTGCCGGTACAGTATGTCTCTTCGATT      240
TGGCCCTGCATAATGTGGGGCTATGTGAGATGACGGAGTAATCAACTCCTCCGATATGCG      300
AGGCTGACAGTTGACATTATCACAAGCTGACACTCGACGCCCCCGCAACAAAGGCCTGTT      360
AAAAATACATCCGCATCGGCTTCTGTCACAAATACGGCGGGCAACTGCTTGTACGGGAGT      420
TTGAAGGCTCCCTTGTTTGTTAATGTCCTTAAGCGCTTCACTTCATCATATTATACATGG      480
CTGCCAAGAGTATTGCCATTCTCCGTGGTTGCAGCCGGGTTGAAATGTGTTTGAACGCCC      540
TATAACAGGTGACTGGGCGGTCAGGAAGTAGCAAAAAAACCATTGTTAGACTCGCTGAAA     600
ACAGAATATCACTCCACACCTTTCAAAATCCCACAACTCGACCTGCCACCGTAAACTAAT      660
ATCTCTCAAACAATTGGATGGGTGGAGAAAACGGATAAAGCCTAAACCCAGATACAGCAC     720
TAGCAACTCTAACCCAAGTTCGGTGGAAGTCACTGTGGGGAAAAAGACGAGACATTGTAA     780
CAGGTGGCACAAGACGAGGTATAAAACGCAGTTTTGGAAAGAGAAAATGAGTTAAAATGG      840
CCCAAATATTGCCCTGGTAGCTGTTTCACCTTTTATACACTAACCCCGAAGACTTTATAC      900
CGCCTCGTAGTGCACACAAAGACCCTGCACATCACTCCTACGTCTCTGCGATCACTCATC      960
ATAGCACCTTTCTTGAACCTTGTTCTGAGACCCCTCCTGGAGGGAGTGTATAAGAGAGAG     1020
TCGTGCGGCACACTGAGATGAGCCCCAAACTATCCATTGCAATATG
```

>AB01093 52F06 *Yarrowia lipolylica*; 1032 nt

```
GTTAACGCTCTTTCTCCGTTGTCACCGACTAAAACTGGCGCACTTTAGATCACTTGTACG       60   (SEQ ID NO: 85)
CTAACAAAGCCACCGCCACGTTTCAGCCATTTTTGAAAGGGTAAGGATACTTGAATCATG     120
ATTTTTATGTTTTCATTTTGTCATTTCCAAGTCGTTCGTTATGCACCCCAGATTTTTTAT      180
```

-continued

```
TTTTATTTTTATTTCAACATCATTTTCTATTTAAACATCAATTTTTATTTAAACATCAAT      240

TTCTATTTAAACACCAATTTCTATTTAAACACCAATTTCTATTTCAAGTTCTATTCGATT      300

TCCATTTATATATATTTCCATTTCCAAAATCCATTTCCATTTCCATTATTATTCATCT        360

CCAGATTCACATGTGAACCTGTGGCAAAACAACCTTTATAGTCATGGTGGGGATGGTGG       420

CATAGCGGGGCAGTTTCAGCAGAAAAATGATATGGAGCCTCCGGACAGTCATGCGGCTAT     480

CGAGCATACATCCGGTCATATGTACAAGTACGCCCCATGTACCATACTCGTACCGTATTG     540

TACCGTCTATGCGCCGGGTCACCAAGGTCTAGACGCGTTTCAGTGCATTACAAGCACCAT     600

AACGGCACATCTCCAGACCCCAGATTGCAACCAAAGTTTGTCCTGAGACAGTTCTACAAA     660

ACACACTAATGTAGACGGAGCAACAATAGGCGACCGGATATCCAAACGCGCACCGTAAAA     720

ACCGCAGCAGCCGCCGTCAGTTGCGATTCACGTGACCAGGAGCACTCCTCCGGGGCGCA     780

ATCTGCTTTTTCTCGATGCTGTTTAGTCTCTATCCACGTGACTCGTAAAAAGACCCTTCC     840

TCGCCCCCCACTCCACTCCACACCATCGGACCGTTTAGCGTTTTTCCGTGATGCACCCT     900

TCTTTCACAGGCTGCTCGTACCCTTCCCCCAAAGTGGAACGAAGTTTATCTGGATGGATA     960

TAAGAAGAGAGAAGCCCAAGTTGGACCTCAGCAGCGCCTCAAACCACATCCACCGACCAC    1020

CACAATATCATG

>AB010394 52F07 Yarrowia lipolytica; 690 nt
GAATTCCCCATCGACTCACATCAGGGACACTACAAGTGTCAATGTCCAGTGCACCTAAAA      60 (SEQ ID NO: 86)

ACGGATCTGACTAATGGGATCTTCCGCATTACCCGCTGATCGGAGTCGAACCATGTCTCT     120

TTGATGTCACACGTCTGCAGGGACGCTTTGATTAGCTCCAATGCCATGTTGCGTTGACAA    180

AAGGTGGGCATGAGACACTCGACATGATATCCCTGGAACGACACCGGTTCGAGATGGACT    240

GATAACATCAATTGGCACGCCACACGTGGAGAGCCGCCTCAGATAACCAACTAGCGCTGT    300

CTGTCGGACCGAGGCCAGCCCAATTACACGCACAAAACGGCACTAAACGCAAACCCAGAA  360

CATGAGACAAGAGTGAGTGAGACAGGGTGGAGAAATGAGAGATAGAGGAGAAGGAGGAGA   420

CGAGAAATGTGACCATGGCGGTGGAGAGAAGAGGAAAAAAGAAACTACAAGTATCCAGCA   480

CAAGGAGACACTGCTGAGACATTACATTTCTGTCCAATGGGGTGTGATCGACAACTCTGT    540

TTCACTAGCCTAAACGGCGATACCGCCTTGCCTGTCTTGATCACGCTCCTTGTCCTCTGA   600

CTCAAGTCGCAACTCCTTTGTTCTGGCCCACCATGGGGTATATATAGGGTAGCCGGTGTT   660

GTTGCTCATGACGACAACCGATTTGACATG

>AB010395 52F08 Yarrowia. lipolytica; 821 nt
CTGCAGGTTGCACTTGTATCTCTCGTTTATTTTTCCCTATTCTTTTTGTATCGTTATT       60 (SEQ ID NO: 87)

GACCAACTACGAGAGGTTGCATTCTTGTCCCTCAATTACACGCTCAGACCACCAGAGAGA    120

GGAGGGGAAGAGGTACGAGTATGAGCACAAGAGCATTCTTTGAGGGACACCTGAATCGCA   180

ATTAATAATATGGAAAGTTGTCCATCTTTTCCTCATTCAGTTGGAGACCCGACGCAGTTC    240

AGTATTGATCAAAGTACAAGTAGATCTCCGAACAGCCACAACGTAGAGTCTCTAGCGGAT    300

ACTGTACAGGTTCTGTCCACGAATGGAATCACCAGAAGAAGGGCTAAGTGTTGGTATATT    360

TACCTCAAAAGTTGCTACATGAATCTTGAGCTTTGACCTAGATAAAACTCTCCCTGTAC     420

AAGCAGTCGCACAACACCACATTGACGAGATGTTTACAACATGATATAATAACTGCATGA    480

AATCAAACGTAATCGAAGCACTCCAACTTGGATAACCATTGACCAATGGTCAACCTCACG    540

TGACTCAATTGTCCCGGGGTGGCCTCGTACTCGTCCCCACACCGACACCACCACGTGCAG    600

CCGCTACCCCACAGTCACGATCCCCGCTAGCGTCTTCGGGGTTCTGTTAGCGTATCAATC   660

ACATGTCGAGGTGTGTTTTAAAGTCGTCTTTAGGGTGGAGGAATCAAGGGGTTGTAGTAG   720
```

-continued

TGTACCAGATACATCCACACAAAGACATGAGATTACGATATATACCCTAACCAGGTGTTT   780

CAAAAAACTACAACATATCAACACAGAAACGCTCTAAGATG

>Cognis cprA *C. tropicalis*; 1008 nt
CATCAAGATCATCTATGGGATAATTACGACAGCAACATTGCAGAAAGAGCGTTGGTCAC   60 (SEQ ID NO: 88)

AATCGAAAGAGCCTATGGCGTTGCCGTCGTTGAGGCAAATGACAGCACCAACAATAACGA   120

TGGTCCCAGTGAAGAGCCTTCAGAACAGTCCATTGTTGACGCTTAAGGCACGGATAATTA   180

CGTGGGGCAAAGGAACGCGGAATTAGTTATGGGGGGATCAAAAGCGGAAGATTTGTGTTG   240

CTTGTGGGTTTTTCCTTTATTTTTCATATGATTTCTTTGCGCAAGTAACATGTGCCAAT   300

TTAGTTTGTGATTAGCGTGCCCCACAATTGGCATCGTGGACGGGCGTGTTTTGTCATACC   360

CCAAGTCTTAACTAGCTCCACAGTCTCGACGGTGTCTCGACGATGTCTTCTTCCACCCCT   420

CCCATGAATCATTCAAAGTTGTTGGGGGATCTCCACCAAGGGCACCGGAGTTAATGCTTA   480

TGTTTCTCCCACTTTGGTTGTGATTGGGGTAGTCTAGTGAGTTGGAGATTTTCTTTTTTT   540

CGCAGGTGTCTCCGATATCGAAATTTGATGAATATAGAGAGAAGCCAGATCAGCACAGTA   600

GATTGCCTTTGTAGTTAGAGATGTTGAACAGCAACTAGTTGAATTACACGCCACCACTTG   660

ACAGCAAGTGCAGTGAGCTGT<u>AAACGA</u>TGCAGCCAGAGTGTCACCACCAACTGACGTTGG   720

GTGGAGTTGTTGTTGTTGTTGGCAGGGCCATATTGCT<u>AAACGA</u>AGACAAGTAGCACA   780

AAACCCAAGCTTAAGAACAAAAATAAAAAAAATTCATACGACAATTCC<u>AAAGCCA</u>TTGAT   840

TTACATAATCAACAGTAAGACAGAAAAAACTTTCAACATTTCAAAGTTCCCTTTTTCCTA   900

TTACTTCTTTTTTTTCTTCTTTCCTTCTTTCCTTCTGTTTTTCTTACTTTATCAGTCTTT   960

TACTTGTTTTTGCAATTCCTCATCCTCCTCCTACTCCTCCTCACCATG

>Cognis cprB *C. tropicalis*; 1035 nt
TATATGATATATGATATATCTTCCTGTGTAATTATTATTCGTATTCGTTAATACTTACTA   60 (SEQ ID NO: 89)

CATTTTTTTTCTTTATTTATGAAGAAAAGGAGAGTTCGTAAGTTGAGTTGAGTAGAATA   120

GGCTGTTGTGCATACGGGGAGCAGAGGAGAGTATCCGACGAGGAGGAACTGGGTGAAATT   180

TCATCTATGCTGTTGCGTCCTGTACTGTACTGTAAATCTTAGATTTCCTAGAGGTTGTTC   240

TAGCAAATAAAGTGTTTCAAGATACAATTTTACAGGCAAGGGTAAAGGATCAACTGATTA   300

GCGGAAGATTGGTGTTGCCTGTGGGGTTCTTTTATTTTTCATATGATTTCTTTGCGCGAG   360

TAACATGTGCCAATCTAGTTTATGATTAGCGTACCTCCACAATTGGCATCTTGGACGGGC   420

GTGTTTTGTCTTACCCCAAGCCTTATTTAGTTCCACAGTCTCGACGGTGTCTCGCCGATG   480

TCTTCTCCCACCCCTCGCAGGAATCATTCGAAGTTGTTGGGGATCTCCTCCGCAGTTTA   540

TGTTCATGTCTTTCCCACTTTGGTTGTGATTGGGGTAGCGTAGTGAGTTGGTGATTTTCT   600

TTTTTCGCAGGTGTCTCCGATATCGAAGTTTGATGAATATAGGAGCCAGATCAGCATGGT   660

ATATTGCCTTTGTAGATAGAGATGTTGAACAACAACTAGCTGAATTACACACCACCGCT<u>A</u>   720

<u>AACGA</u>TGCGCACAGGGTGTCACCGCCAACTGACGTTGGGTGGAGTGTTGTTGGCAGGGC   780

CATATTGCT<u>AAACGA</u>AGAGAAGTAGCACAAAACCCAAGGTTAAGAACAATTAAAAAAATT   840

CATACGACAATTCCACAGCCATTTACATAATCAACAGCGACAAATGAGACAGAAAAAACT   900

TTCAACATTTCAAAGTTCCCTTTTTCCTATTACTTCTTTTTTTCTTTCCTTCCTTTCATT   960

TCCTTTCCTTCTGCTTTTATTACTTTACCAGTCTTTTGCTTGTTTTTGCAATTCCTCATC   1020

CTCCTCCTCACCATG

Cognis cypalla *C. tropicalis*; 1178 nt
CATATGCGCTAATCTTCTTTTTCTTTTTATCACAGGAGAAACTATCCCACCCCCACTTCG   60 (SEQ ID NO: 90)

```
AAACACAATGACAACTCCTGCGTAACTTGCAAATTCTTGTCTGACTAATTGAAAACTCCG    120

GACGAGTCAGACCTCCAGTAAACGGACAGACAGACAAACACTTGGTGCGATGTTCATAC    180

CTACAGACATGTCAACGGGTGTTAGACGACGGTTTCTTGCAAAGACAGGTGTTGGCATCT    240

CGTACGATGGCAACTGCAGGAGGTGTCGACTTCTCCTTTAGGCAATAGAAAAAGACTAAG    300

AGAACAGCGTTTTTACAGGTTGCATTGGTTAATGTAGTATTTTTTTAGTCCCAGCATTCT    360

GTGGGTTGCTCTGGGTTTCTAGAATAGGAAATCACAGGAGAATGCAAATTCAGATGGAAG    420

AACAAAGAGATAAAAAACAAAAAAAAACTGAGTTTTGCACCAATAGAATGTTTGATGATA    480

TCATCCACTCGCTAAACGAATCATGTGGGTGATCTTCTCTTTAGTTTTGGTCTATCATAA    540

AACACATGAAAGTGAAATCCAAATACACTACACTCCGGGTATTGTCCTTCGTTTTACAGA    600

TGTCTCATTGTCTTACTTTTGAGGTCATAGGAGTTGCCTGTGAGAGATCACAGAGATTAT    660

ACACTCACATTTATCGTAGTTTCCTATCTCATGCTGTGTGTCTCTGGTTGGTTCATGAGT    720

TTGGATTGTTGTACATTAAAGGAATCGCTGGAAAGCAAAGCTAACTAAATTTTCTTTGTC    780

ACAGGTACACTAACCTGTAAAACTTCACTGCCACGCCAGTCTTTCCTGATTGGGCAAGTG    840

CACAAACTACAACCTGCAAAACAGCACTCCGCTTGTCACAGGTTGTCTCCTCTCAACCAA    900

CAAAAAAATAAGATTAAACTTTCTTTGCTCATGCATCAATCGGAGTTATCTCTGAAAGAG    960

TTGCCTTTGTGTAATGTGTGCCAAACTCAAACTGCAAAACTAACCACAGAATGATTTCCC    1020

TCACAATTATATAAACTCACCCACATTTCCACAGACCGTAATTTCATGTCTCACTTTCTC    1080

TTTTGCTCTTCTTTTACTTAGTCAGGTTTGATAACTTCCTTTTTTATTACCCTATCTTAT    1140

TTATTTATTTATTCATTTATACCAACCAACCAACCATG

>Cognis cypa2a C. tropicalis; 1201 nt
GACCTGTGACGCTTCCGGTGTCTTGCCACCAGTCTCCAAGTTGACCGACGCCCAAGTCAT     60 (SEQ ID NO: 91)

GTACCACTTTATTTCCGGTTACACTTCCAAGATGGCTGGTACTGAAGAAGGTGTCACGGA    120

ACCACAAGCTACTTTCTCCGCTTGTTTCGGTCAACCATTCTTGGTGTTGCACCCAATGAA    180

GTACGCTCAACAATTGTCTGACAAGATCTCGCAACACAAGGCTAACGCCTGGTTGTTGAA    240

CACCGGTTGGGTTGGTTCTTCTGCTGCTAGAGGTGGTAAGAGATGCTCATTGAAGTACAC    300

CAGAGCCATTTTGGACGCTATCCACTCTGGTGAATTGTCCAAGGTTGAATACGAAACTTT    360

CCCAGTCTTCAACTTGAATGTCCCAACCTCCTGTCCAGGTGTCCCAAGTGAAATCTTGAA    420

CCCAACCAAGGCCTGGACCGGAAGGTGTTGACTCCTTCAACAAGGAAATCAAGTCTTTGG    480

CTGGTAAGTTTGCTGAAAACTTCAAGACCTATGCTGACCAAGCTACCGCTGAAGTGAGAG    540

CTGCAGGTCCAGAAGCTTAAAGATATTTATTCATTATTTAGTTTGCCTATTTATTTCTCA    600

TTACCCATCATCATTCAACACTATATATAAAGTTACTTCGGATATCATTGTAATCGTGCG    660

TGTCGCAATTGGATGATTTGGAACTGCGCTTGAAACGGATTCATGCACGAAGCGGAGATA    720

AAAGATTACGTAATTTATCTCCTGAGACAATTTTAGCCGTGTTCACACGCCCTTCTTTGT    780

TCTGAGCGAAGGATAAATAATTAGACTTCCACAGCTCATTCTAATTTCCGTCACGCGAAT    840

ATTGAAGGGGGTACATGTGGCCGCTGAATGTGGGGGCAGTAAACGCAGTCTCTCCTCTC    900

CCAGGAATAGTGCAACGGAGGAAGGATAACGGATAGAAAGCGGAATGCGAGGAAAATTTT    960

GAACGCGCAAGAAAAGCAATATCCGGGCTACCAGTTTTTGAGCCAGGGAACACACTCCTA    1020

TTTCTGCTCAATGACTGAACATAGAAAAAACACCAAGACGCAATGAAACGCACATGGACA    1080

TTTAGACCTCCCCACATGTGATAGTTTGTCTTAACAGAAAAGTATAATAAGAACCCATGC    1140

CGTCCCTTTTCTTTCGCCGCTTCAACTTTTTTTTTTTATCTTACACACATCACGACCAT    1200

G
```

-continued

Cognis cypa2b *C. tropicalis*; 1071 nt
GCTCAACAATTGTCTGACAAGATCTCGCAACACAAGGCTAACGCCTGGTTGTTGAACACT     60 (SEQ ID NO: 92)

GGTTGGGTTGGTTCTTCTGCTGCTAGAGGTGGTAAGAGATGTTCATTGAAGTACACCAGA     120

GCCATTTTGGACGCTATCCACTCTGGTGAATTGTCCAAGGTTGAATACGAGACTTTCCCA     180

GTCTTCAACTTGAATGTCCCAACCTCCTGCCCAGGTGTCCCAAGTGAAATCTTGAACCCA     240

ACCAAGGCCTGGACCGAAGGTGTTGACTCCTTCAACAAGGAAATCAAGTCTTTGGCTGGT     300

AAGTTTGCTGAAAACTTCAAGACCTATGCTGACCAAGCTACCGCTGAAGTTAGAGCTGCA     360

GGTCCAGAAGCTTAAAGATATTTATTCACTATTTAGTTTGCCTATTTATTTCTCATCACC     420

CATCATCATTCAACAATATATATAAAGTTATTTCGGAACTCATATATCATTGTAATCGTG     480

CGTGTTGCAATTGGGTAATTTGAAACTGTAGTTGGAACGGATTCATGCACGATGCGGAGA     540

TAACACGAGATTATCTCCTAAGACAATTTTGGCCTCATTCACACGCCCTTCTTCTGAGCT     600

AAGGATAAATAATTAGACTTCACAAGTTCATTAAAATATCCGTCACGCGAAAACTGCAAC     660

AATAAGGAAGGGGGGGTAGACGTAGCCGATGAATGTGGGGTGCCAGTAAACGCAGTCTC     720

TCTCTCCCCCCCCCCCCCCCCCCCTCAGGAATAGTACAACGGGGGAAGGATAACGGATA     780

GCAAGTGGAATGCGAGGAAAATTTTGAATGCGCAAGGAAAGCAATATCCGGGCTATCAGG     840

TTTTGAGCCAGGGGACACACTCCTCTTCTGCACAAAAACTTAACGTAGACAAAAAAAAAA     900

AACTCCACCAAGACACAATGAATCGCACATGGACATTTAGACCTCCCCACATGTGAAAGC     960

TTCTCTGGCGAAAGCAAAAAAAGTATAATAAGGACCCATGCCTTCCCTCTTCCTGGGCCG     1020

TTTCAACTTTTTCTTTTCTTTGTCTATCAACACACACACACCTCACGACC

Cognis cypa3a *C. tropicalis*; 1128 nt
GACATCATAATGACCCGGTTATTTCGCCCTCAGGTTGCTTATTTGAGCCGTAAAGTGCAG     60 (SEQ ID NO: 93)

TAGAAACTTTGCCTTGGGTTCAAACTCTAGTATAATGGTGATAACTGGTTGCACTCTTGC     120

CATAGGCATGAAAATAGGCCGTTATAGTACTATATTTAATAAGCGTAGGAGTATAGGATG     180

CATATGACCGGTTTTTCTATATTTTTAAGATAATCTCTAGTAAATTTTGTATTCTCAGTA     240

GGATTTCATCAAATTTCGCAACCAATTCTGGCGAAAAAATGATTCTTTTACGTCAAAAGC     300

TGAATAGTGCAGTTTAAAGCACCTAAAATCACATATACAGCCTCTAGATACGACAGAGAA     360

GCTCTTTATGATCTGAAGAAGCATTAGAATAGCTACTATGAGCCACTATTGGTGTATATA     420

TTAGGGATTGGTGCAATTAAGTACGTACTAATAAACAGAAGAAAATACTTAACCAATTTC     480

TGGTGTATACTTAGTGGTGAGGGACCTTTTCTGAACATTCGGGTCAAACTTTTTTTTGGA     540

GTGCGACATCGATTTTCGTTTGTGTAATAATAGTGAACCTTTGTGTAATAAATCTTCAT     600

GCAAGCTTGCATAATTCGAGCTTGGGAGTTCACGCCAATTTGACCTCGTTCATGTGATA     660

AAAGAAAAGCCAAAAGGTAATTAGCAGACGCAATGGGAACATGGAGTGGAAAGCAA**TGGA     720

AGCACGCCCAGGACGGAGTAATTTAGTCCACACTACATCTGGGGGTTTTTTTTTTGTGCG     780

CAAGTACACACCTGGACTTTAGTTTTTGCCCCATAAAGTTAACAATCTAACCTTTGGCTC     840

TCCAACTCTCTCCGCCCCCAAATATTCGTTTTTACACCCTCAAGCTAGCGACAGCACAAC     900

ACCCATTAGAGGAATGGGGCAAAGTTAAACACTTTTGGCTTCAATGATTCCTATTCGCTA     960

CTACATTCTTCTCTTGTTTTGTGCTTTGAATTGCACCATGTGAAATAAACGACAATTATA     1020

TATACCTTTTCATCCCTCCTCCTATATCTCTTTTTGCTACATTTTGTTTTTTACGTTTCT     1080

TGCTTTTGCACTCTCCCACTCCCACAAAGAAAAAAAAACTACACTATG

Cognis cypa3b *C. tropicalis*; 915 nt
CCTGCAGAATTCGCGGCCGCGTCGACAGAGTAGCAGTTATGCAAGCATGTGATTGTGGTT     60 (SEQ ID NO: 94)

```
                                                                 -continued
TTTGCAACCTGTTTGCACGACAAATGATCGACAGTCGATTACGTAATCCATATTATTTAG      120

AGGGGTAATAAAAAATAAATGGCAGCCAGAATTTCAAACATTTTGCAAACAATGCAAAAG      180

ATGAGAAACTCCAACAGAAAAAATAAAAAAACTCCGCAGCACTCCGAACCAACAAAACAA      240

TGGGGGGCGCCAGAATTATTGACTATTGTGACTTTTTTTATTTTTTCCGTTAACTTTCA      300

TTGCAGTGAAGTGTGTTACACGGGGTGGTGATGGTGTTGGTTTCTACAATGCAAGGGCAC      360

AGTTGAAGGTTTCCACATAACGTTGCACCATATCAACTCAATTTATCCTCATTCATGTGA      420

TAAAAGAAGAGCCAAAAGGTAATTGGCAGACCCCCCAAGGGGAACACGGAGTAGAAAGCA      480

ATGGAAACACGCCCATGACAGTGCCATTTAGCCCACAACACATCTAGTATTCTTTTTTTT      540

TTTTGTGCGCAGGTGCACACCTGGACTTTAGTTATTGCCCCATAAAGTTAACAATCTCAC      600

CTTTGGCTCTCCCAGTGTCTCCGCCTCCAGATGCTCGTTTTACACCCTCGAGCTAACGAC      660

AACACAACACCCATGAGGGGAATGGGCAAAGTTAAACACTTTTGGTTTCAATGATTCCTA      720

TTTGCTACTCTCTTGTTTTGTGTTTTGATTTGCACCATGTGAAATAAACGACAATTATAT      780

ATACCTTTTCGTCTGTCCTCCAATGTCTCTTTTTGCTGCCATTTTGCTTTTTGCTTTTTG      840

CTTTTGCACTCTCTCCCACTCCCACAATCAGTGCAGCAACACACAAAGAAGAAAAATAAA      900

AAAACCTACACTATG

>Cognis cypa4a C. tropicalis; 769 nt
GATGTGGTGCTTGATTTCTCGAGACACATCCTTGTGAGGTGCCATGAATCTGTACCTGTC       60  (SEQ ID NO: 95)

TGTAAGCACAGGGAACTGCTTCAACACCTTATTGCATATTCTGTCTATTGCAAGCGTGTG      120

CTGCAACGATATCTGCCAAGGTATATAGCAGAACGTGCTGATGGTTCCTCCGGTCATATT      180

CTGTTGGTAGTTCTGCAGGTAAATTTGGATGTCAGGTAGTGGAGGGAGGTTTGTATCGGT      240

TGTGTTTTCTTCTTCCTCTCTCTCTGATTCAACCTCCACGTCTCCTTCGGGTTCTGTGTC      300

TGTGTCTGAGTCGTACTGTTGGATTAAGTCCATCGCATGTGTGAAAAAAAGTAGCGCTTA      360

TTTAGACAACCAGTTCGTTGGGCGGGTATCAGAAATAGTCTGTTGTGCACGACCATGAGT      420

ATGCAACTTGACGAGACGTCGTTAGGAATCCACAGAATGATAGCAGGAAGCTTACTACGT      480

GAGAGATTCTGCTTAGAGGATGTTCTCTTCTTGTTGATTCCATTAGGTGGGTATCATCTC      540

CGGTGGTGACAACTTGACACAAGCAGTTCCGAGAACCACCCACAACAATCACCATTCCAG      600

CTATCACTTCTACATGTCAACCTACGATGTATCTCATCACCATCTAGTTTCTTGGCAATC      660

GTTTATTTGTTATGGGTCAACATCCAATACAACTCCACCAATGAAGAAGAAAAACGGAAA      720

GCAGAATACCAGAATGACAGTGTGAGTTCCTGACCATTGCTAATCTATG

Cognis cypa5a C. tropicalis; 1105 nt
TGGAGTCGCCAGACTTGCTCACTTTTGACTCCCTTCGAAACTCAAAGTACGTTCAGGCGG       60  (SEQ ID NO: 96)

TGCTCAACGAAACGCTCCGTATCTACCCGGGGGTACCACGAAACATGAAGACAGCTACGT      120

GCAACACGACGTTGCCACGCGGAGGAGGCAAAGACGGCAAGGAACCTATCTTGGTGCAGA      180

AGGGACAGTCCGTTGGGTTGATTACTATTGCCACGCAGACGGACCCAGAGTATTTTGGGG      240

CCGACGCTGGTGAGTTTAAGCCGGAGAGATGGTTTGATTCAAGCATGAAGAACTTGGGGT      300

GTAAATACTTGCCGTTCAATGCTGGGCCACGGACTTGCTTGGGGCAGCAGTACACTTTGA      360

TTGAAGCGAGCTACTTGCTAGTCCGGTTGGCCCAGACCTACCGGGCAATAGATTTGCAGC      420

CAGGATCGGCGTACCCACCAAGAAAGAAGTCGTTGATCAACATGAGTGCTGCCGACGGGG      480

TGTTTGTAAAGCTTTATAAGGATGTAACGGTAGATGGATAGTTGTGTAGGAGGAGCGGAG      540

ATAAATTAGATTTGATTTTGTGTAAGGTTTTGGATGTCAACCTACTCCGCACTTCATGCA      600

GTGTGTGTGACACAAGGGTGTACTACGTGTGCGTGTGCGCCAAGAGACAGCCCAAGGGGG      660
```

```
TGGTAGTGTGTGTTGGCGGAAGTGCATGTGACACAACGCGTGGGTTCTGGCCAATGGTGG      720

ACTAAGTGCAGGTAAGCAGCGACCTGAAACATTCCTCAACGCTTAAGACACTGGTGGTAG      780

AGATGCGGACCAGGCTATTCTTGTCGTGCTACCCGGCGCATGGAAAATCAACTGCGGGAA      840

GAATAAATTTATCCGTAGAATCCACAGAGCGGATAAATTTGCCCACCTCCATCATCAACC      900

ACGCCGCCACTAACTACATCACTCCCCTATTTTCTCTCTCTCTTTGTCTTACTCCGCT       960

CCCGTTTCCTTAGCCACAGATACACACCCACTGCAAACAGCAGCAACAATTATAAAGATA     1020

CGCCAGGCCCACCTTCTTTCTTTTTCTTCACTTTTTTGACTGCAACTTTCTACAATCCAC     1080

CACAGCCACCACCACAGCCGCTATG

>Cognis cypa5b C. tropicalis; 1143 nt
TTACAATCATGGAGCTCGCTAGGAACCCAGATGTCTGGGAGAAGCTCCGCGAAGAGGTCA       60 (SEQ ID NO: 97)

ACACGAACTTTGGCATGGAGTCGCCAGACTTGCTCACTTTTGACTCTCTTAGAAGCTCAA     120

AGTACGTTCAGGCGGTGCTCAACGAAACGCTTCGTATCTACCCGGGGGTGCCACGAAACA      180

TGAAGACAGCTACGTGCAACACGACGTTGCCGCGTGGAGGAGGCAAAGACGGTAAGGAAC      240

CTATTTTGGTGCAGAAGGGCCAGTCCGTTGGGTTGATTACTATTGCCACGCAGACGGACC      300

CAGAGTATTTTGGGGCAGATGCTGGTGAGTTCAAACCGGAGAGATGGTTTGATTCAAGCA      360

TGAAGAACTTGGGGTGTAAGTACTTGCCGTTCAATGCTGGCCCCGGACTTGTTTGGGGCA      420

GCAGTACACTTTGATTGAAGCGAGCTATTTGCTAGTCAGGTTGGCGCAGACCTACCGGGT      480

AATCGATTTGCTGCCAGGGTCGGCGTACCCACCAAGAAAGAAGTCGTTGATCAATATGAG      540

TGCTGCCGATGGGGTGGTTGTAAAGTTTCACAAGGATCTAGATGGATATGTAAGGTGTGT      600

AGGAGGAGCGGAGATAAATTAGATTTGATTTTGTGTAAGGTTTAGCACGTCAAGCTACTC      660

CGCACTTTGTGTGTAGGGAGCACATACTCCGTCTGCGCCTGTGCCAAGAGACGGCCCAGG      720

GGTAGTGTGTGGTGGTGGAAGTGCATGTGACACAATACCCTGGTTCTGGCCAATTGGGGA      780

TTTAGTGTAGGTAAGCTGCGACCTGAAACACTCCTCAACGCTTGAGACACTGGTGGGTAG      840

AGATGCGGGCCAGGAGGCTATTCTTGTCGTGCTACCCGTGCACGGAAAATCGATTGAGGG      900

AAGAACAAATTTATCCGTGAAATCCACAGAGCGGATAAATTTGTCACATTGCTGCGTTGC      960

CCACCCACAGCATTCTCTTTTCTCTCTCTTTGTCTTACTCCGCTCCTGTTTCCTTATCCA     1020

GAAATACACACCAACTCATATAAAGATACGCTAGCCCAGCTGTCTTTCTTTTTCTTCACT     1080

TTTTTTGGTGTGTTGCTTTTTTGGCTGCTACTTTCTACAACCACCACCACCACCACCACC     1140

ATG

>Cognis cypa8a C. tropicalis; 466 nt
GAATTCTTTGGATCTAATTCCAGCTGATCTTGCTAATCCTTATCAACGTAGTTGTGATCA       60 (SEQ ID NO: 98)

TTGTTTGTCTGAATTATACACACCAGTGGAAGAATATGGTCTAATTTGCACGTCCCACTG      120

GCATTGTGTGTTTGTGGGGGGGGGGGGTGCACACATTTTTAGTGCCATTCTTTGTTGAT      180

TACCCCTCCCCCCTATCATTCATTCCCACAGGATTAGTTTTTTCCTCACTGGAATTCGCT      240

GTCCACCTGTCAACCCCCCCCCCCCCCCCCCCCACTGCCCTACCCTGCCCTGCCCTGCAC      300

GTCCTGTGTTTTGTGCTGTGTCTTTCCCACGCTATAAAAGCCCTGGCGTCCGGCCAAGGT      360

TTTTCCACCCAGCCAAAAAAACAGTCTAAAAAATTTGGTTGATCCTTTTTGGTTGCAAGG      420

TTTTCCACCACCACTTCCACCACCTCAACTATTCGAACAAAAGATG

>Cognis cypa8b C. tropicalis; 782 nt
AAAACCGATACAAGAAGAAGACAGTCAACAAGAACGTTAATGTCAACCAGGCGCCAAGAA       60 (SEQ ID NO: 99)

GACGGTTTGGCGGACTTGGAAGAATGTGGCATTTGCCCATGATGTTTATGTTCTGGAGAG      120

GTTTTTTCAAGGAATCGTCATCCTCCGCCACCACAAGAACCACCAGTTAACGAGATCCATA      180
```

-continued

```
TTCACAACCCACCGCAAGGTGACAATGCTCAACAACAACAGCAACAACAACAACCCCCAC      240

AAGAACAGTGGAATAATGCCAGTCAACAAAGAGTGGTGACAGACGAGGGAGAAAACGCAA      300

GCAACAGTGGTTCTGATGCAAGATCAGCTACACCGCTTCATCAGGAAAAGCAGGAGCTCC      360

CACCACCATATGCCCATCACGAGCAACACCAGCAGGTTAGTGTATAGTAGTCTGTAGTTA      420

AGTCAATGCAATGTACCAATAAGACTATCCCTTCTTACAACCAAGTTTTCTGCCGCGCCT      480

GTCTGGCAACAGATGCTGGCCGACACACTTTCAACTGAGTTTGGTCTAGAATTCTTGCAC      540

ATGCACGACAAGGAAACTCTTACAAAGACAACACTTGTGCTCTGATGCCACTTGATCTTG      600

CTAAGCCTTATCAACGTAATTGAGATCATTGTTTGTCTGAATTATACACACCAGTGGAAG      660

AATCTGGTCTAATCTGCACGCCTCATGGGCATTGTGTGTTTTGGGGGGGGGGGGGGGGT      720

GCACACATTTTTAGTGCGAATGTTTGTTTGCTGGTTCCCCCTCCCCCCTCCCCCCTATCA      780

TG
```

>M24894 CP5a *C. tropicalis*; 773 nt
```
AAAGAAGACAAAGAAAAAGATTTGCGGTCAAAATAGAAAAAGAAAAAAGAAACAACTGTC       60   (SEQ ID NO: 100)

CGGGCTAGTGAAATACTATACTATTGCTAGAGGGGTAATAGAACAACGGGGGATTATAGA      120

CAATTTGAAAACAATAGAAGACACAAAATACTCCATGATAAAATAGAAATTGATTTGCAA      180

GACTACAACAGGTAGACTTAAAGAAAAAAATTCCGCAATACTCCGAAAATACACAAAAAC      240

AATACTGTCCGTTTCCATCGCATTAAGAAGTCTATTCAACAATAGTTTCAAGGAGTTTGA      300

ATATAGACTCCGTTAGAAGATTGATGTTCTGATTTCATGTGAAAAAAAATATCTAATGGA      360

AGTATACAATTAATGATAATCAATAAGTAACTATTAAGAATGTCAAATATTCCAACTTAT      420

TCGTATCCTGACAAAAGTACACGCCCCGTTTATGCGGTACTTTTGTCAATTTCAATTTTT      480

TTCCCCAATAAAGTTACTTTGTTCACCAACAACAACCATGAGGGGAACCACAGAATTCTG      540

TAATTTTTTAAACACCAGGGTTCAATTTCCCTTCCCTTTTTTTAGGTTATGAAGATTGG      600

TTATGTTAATACCATGTGAAATAAACTACAAATATATATATCTTTTTAATTGCCCATCTC      660

TGCTACTCCCTCTCTCTCTGATGTAGGTTTTTCTTTTTTTTTTATTGTACGTGAACTT      720

GGCTGCACAGTAGAATCAATTACTTTTGCACCTGGTTCTATTACACAAAAATG
```

>Z13010 CP5f *C. tropicalis*; 787 nt
```
GATATCATCAGAAGAGGTCGTCTGTAGTGAATAAATCATATGGCTGTAGTGAATCTGCTA       60   (SEQ ID NO: 101)

CGTTAAAAAAATAAACCCACATGAAAAGTCGAAACCTACATTGTTAGCTATTGTTACAC      120

AAGTTAAGCTGAACTTGTTTGACAAGTTATCACATTCACTTTCTTTGTGGATAGCTATTG      180

TAAAGCACATCTATTACAATAACTAGCTATCTTTTGTAATACCATTCGTATCGTTATGGT      240

TTCATTTGGTGTTGAAGAGAAAATGAATAATTGATCATTAGTACACGAACCCTTCTATCA      300

CCAAAAATTAAAACACCAATTTTCTTTGTGACAATTAACGTATTCCTAATTAGGAAGTA      360

TTACATGGCATAAACCTGTAAAAAATGCAGAAGACATAAAATGCCCATAATAAAAGTTGA      420

TTTCTCCGCATGCGATGGTTAAGTAAAGTCTTATGCATAAATCGGACTTTACTAGTTTG      480

CCCTTTTGTTTTGCTTCTTCTTCTTCTTTTTCTAATTTTGTTGGTACTGCAAAAACGAA      540

CCCCAAAATCAAACTCTTAAAACCTAATTACAAATAACAACTATATAAACACAATGTCAT      600

TTCCCTTTCCCCAAAGTTTTCCCTTTTTTATTTTTAGTTTCTTATATCTTTACTTGTAC      660

ATAAGGTTTTCTACAACTTCTTTTTTTGGATTACTTAATTAGGTTTTACTTTGACACAGT      720

CCGTACTTACTAAATTATTTATTCCATTCATTCCATTCATTTATTCATATCACATCATAT      780

AACTATG
```

>Z13011 CP5g *C. tropicalis*; 407 nt

```
                                    -continued
ACAAGATGTGGTATAATTACAATCCAAGTATTACAACGCCCAAGTGTGAAGGGGAATGAA    60  (SEQ ID NO: 102)

AAGAAAACGAAAAAAAAAAGAAATAAAAACACATTATCCATTCTTTCTTTGTATAGCTAT   120

ATTATATATTAGTCAAACCAGTATATCCCCGCCTTGTACGGGGTCCTTTCGTTGTAATTT   180

CATCTCGTGCCCCTCCTCCTTCTTATCACGCCCATTTTATTTTTTTTTTGTTCGACTTT    240

CCCTGTGTGAAATTCCAACCGTGGTATAAAACTTTGTCAATTTGACCAAGATTGTCAAGT   300

GTAAAGATAAAGGCTAAATAAAAGATATACTTTCTCTTTGAATAGTGACAATAATCTCAA   360

AGTTTGGTTGCAAGAGTTTTATTTCCATAGTCACTAATAGAATAATG

>Z13012 CP5h C. tropicalis; 268 nt
GAATTCTAACGGAGAAATAGTTTCAGTTGACTTATCATTGATTCCTTTCATAAAGAAAAA    60  (SEQ ID NO: 103)

ATGATGTAACAAAGGGAGAACAAAAAAAAAAAGGAGAAGCAATAAACTCCGCTCCTTCT    120

AACAATTAGGCAACCACACACGTTGGACATATATATATATATATATGTTCTGGTATGTTG   180

TCTCCTTTAATTTTTTCCAGCGATTTTCATCGACAACATAATTTATTGATCTTTTTTTTT   240

TCAATTAGACATATTCCAACCCACAATG

>Z13013 CP5n C. tropicalis; 498 nt
GAATTCAATCGGCCGTTGATTAGATAAGCCAATTGTTGCTGTAATGTCATACAGTTTTTT    60  (SEQ ID NO: 104)

TTTTTTTTTTGATTCGGGTTTACAGTAGTTCAACTGGATTGTTTTACGAGAGTGATAGA   120

GTGACAAAATCTCGTAGACAGTACAACTGTATCTTATTGTATTTTTTTTTGTCATCATC   180

TTCTTCGCAGTATACAAATGTGCCGGACTAAAATGACTGCAAAATATAAATTTTAGATTA   240

TATAAACAAAATAAACAAAGGAGCTAAAAATAGGTACTAAATCACGGACGGTACTAGTAC   300

TAGACATTGTGTATGATGAGTGATTGTATTGAGTCAAGAATAAACATTAGATCACTATTG   360

GTAAAATGTCTCTTTGGAAATGATTAATTGTACACATAGTTTCGTAATGCAGCATAGAGT   420

GGATTATATAAAGAGCAGTCATAGGACAAAAATTATGATATCGATATCATTTTGTTTGTA   480

TACATACCATCGACCATG

>Z13014 CP5p C. tropicalis; 71 nt
ACATAAGTATATTCTCTTTACTATCCAAATAACTTTATATTCATTCATCAAAAACCTTTT    60  (SEQ ID NO: 105)

ACACCGTGATG
```

TABLE 1

Unique features in the upstream regions of CYP52, CPR, and POX genes

| Gene | -1A | -3A | -6A | (C/T)GGTT(A/G)TT(C/A/G) (SEQ ID NO:4) |
|---|---|---|---|---|
| Cognis genes | | | | |
| A1A | − | + | − | − |
| A2A | − | + | + | + |
| A2B | − | + | + | + |
| A3A | − | + | − | − |
| A3B | − | + | − | − |
| A5A | − | − | − | − |
| A5B | − | + | + | − |
| A8A | − | + | − | − |
| A8B | − | + | − | − |
| D4A | − | − | − | − |
| CPRA | − | + | − | − |
| CPRB | − | + | − | − |
| POX2 | − | + | + | − |
| POX4 | + | + | − | ++* |
| POX5 | − | + | − | − |
| Published Candida tropicalis genes | | | | |
| Alk6 | − | + | + | − |
| Alk7 | + | + | + | − |
| Alk8 | + | + | − | − |
| Alkb1 | − | + | − | − |
| Alkc1 | − | − | + | − |
| P/Red | − | − | − | − |
| Candida maltosa genes | | | | |
| Alk1a | − | − | − | + |
| Alk1b | − | − | − | − |
| Alk2a | + | + | − | − |
| Alk3a | − | + | − | − |
| Alk4 | + | − | − | − |
| Alk5a | − | + | + | − |
| Alk6a | − | + | + | − |
| Alk7 | − | + | + | − |
| Alk8 | − | + | + | − |

TABLE 1-continued

Unique features in the upstream regions of CYP52, CPR, and POX genes

| Gene | −1A | −3A | −6A | (C/T)GGTT(A/G)TT(C/A/G) (SEQ ID NO:4) |
|---|---|---|---|---|
| *Yarrowia lipolytica* genes | | | | |
| AIk1 | − | + | − | − |
| Alk2 | − | + | + | − |
| AIk3 | + | + | + | − |
| AIk4 | − | − | − | − |
| AIk5 | − | + | − | − |
| Alk6 | − | + | + | − |
| Alk7 | − | − | − | − |
| AIk8 | − | + | − | − |

EXAMPLE 2

Deletion and/or Deactivation of an Upstream Repressing Sequence in CYP52A3A

```
CYP52A3A sequence

URS1-AAACGA-position 1007
URS2-AAAGCCA-position 666
         10        20        30        40        50        60      (SEQ ID NO: 106)
GACATCATAATGACCCGGTTATTTCGCCCTCAGGTTGCTTATTTGAGCCGTAAAGTGCAG 70        80        90       100       110       120
TAGAAACTTTGCCTTGGGTTCAAACTCTAGTATAATGGTGATAACTGGTTGCACTCTTGC 130       140       150       160       170       180
CATAGGCATGAAAATAGGCCGTTATAGTACTATATTTAATAAGCGTAGGAGTATAGGATG 190       200       210       220       230       240
CATATGACCGGTTTTTCTATATTTTAAGATAATCTCTAGTAAATTTTGTATTCTCAGTA 250       260       270       280       290       300
GGATTTCATCAAATTTCGCAACCAATTCTGGCGAAAAAATGATTCTTTTACGTCAAAAGC 310       320       330       340       350       360
TGAATAGTGCAGTTTAAAGCACCTAAAATCACATATACAGCCTCTAGATACGACAGAGAA 370       380       390       400       410       420
GCTCTTTATGATCTGAAGAAGCATTAGAATAGCTACTATGAGCCACTATTGGTGTATATA 430       440       450       460       470       480
TTAGGGATTGGTGCAATTAAGTACGTACTAATAAACAGAAGAAAATACTTAACCAATTTC 490       500       510       520       530       540
TGGTGTATACTTAGTGGTGAGGGACCTTTTCTGAACATTCGGGTCAAACTTTTTTTTGGA 550       560       570       580       590       600
GTGCGACATCGATTTTTCGTTTGTGTAATAATAGTGAACCTTTGTGTAATAAATCTTCAT 610       620       630       640       650       660
GCAAGACTTGCATAATTCGAGCTTGGGAGTTCACGCCAATTTGACCTCGTTCATGTGATA 670       680       690       700       710       720
AAAGAAAAGCCAAAAGGTAATTAGCAGACGCAATGGGAACATGGAGTGGAAAGCAATGGA 730       740       750       760       770       780
AGCACGCCCAGGACGGAGTAATTTAGTCCACACTACATCTGGGGGTTTTTTTTTGTGCG 790       800       810       820       830       840
CAAGTACACACCTGGACTTTAGTTTTTGCCCCATAAAGTTAACAATCTAACCTTTGGCTC 850       860       870       880       890       900
TCCAACTCTCTCCGCCCCCAAATATTCGTTTTTACACCCTCAAGCTAGCGACAGCACAAC 910       920       930       940       950       960
ACCCATTAGAGGAATGGGGCAAAGTTAAACACTTTTGGCTTCAATGATTCCTATTCGCTA 970       980       990      1000      1010      1020
CTACATTCTTCTCTTGTTTTGTGCTTTGAATTGCACCATGTGAAATAAACGACAATTATA 1030      1040      1050      1060      1070      1080
TATACCTTTTCATCCCTCCTCCTATATCTCTTTTTGCTACATTTTGTTTTTTACGTTTCT
```

-continued

```
         1090       1100       1110       1120       1130
TGCTTTTGCACTCTCCCACTCCCACAAAGAAAAAAAAACTACACT ATG TCG TCT TCT
                                              M   S   S   S>

1140       1150       1160       1170       1180
CCA TCG TTT GCC CAA GAG GTT CTC GCT ACC ACT AGT CCT TAC ATC
 P   S   F   A   Q   E   V   L   A   T   T   S   P   Y   I>

1190       1200       1210       1220
GAG TAC TTT CTT GAC AAC TAC ACC AGA TGG TAC TAC TTC ATA CCT
 E   Y   F   L   D   N   Y   T   R   W   Y   Y   F   I   P>

1230       1240       1250       1260       1270
TTG GTG CTT CTT TCG TTG AAC TTT ATA AGT TTG CTC CAC ACA AGG
 L   V   L   L   S   L   N   F   I   S   L   L   H   T   R>

1280       1290       1300       1310
TAC TTG GAA CGC AGG TTC CAC GCC AAG CCA CTC GGT AAC TTT GTC
 Y   L   E   R   R   F   H   A   K   P   L   G   N   F   V>

1320       1330       1340       1350       1360
AGG GAC CCT ACG TTT GGT ATC GCT ACT CCG TTG CTT TTG ATC TAC
 R   D   P   T   F   G   I   A   T   P   L   L   L   I   Y>

1370       1380       1390       1400
TTG AAG TCG AAA GGT ACG GTC ATG AAG TTT GCT TGG GGC CTC TGG
 L   K   S   K   G   T   V   M   K   F   A   W   G   L   W>

1410       1420       1430       1440       1450
AAC AAC AAG TAC ATC GTC AGA GAC CCA AAG TAC AAG ACA ACT GGG
 N   N   K   Y   I   V   R   D   P   K   Y   K   T   T   G>

1460       1470       1480       1490
CTC AGG ATT GTT GGC CTC CCA TTG ATT GAA ACC ATG GAC CCA GAG
 L   R   I   V   G   L   P   L   I   E   T   M   D   P   E>

1500       1510       1520       1530       1540
AAC ATC AAG GCT GTT TTG GCT ACT CAG TTC AAT GAT TTC TCT TTG
 N   I   K   A   V   L   A   T   Q   F   N   D   F   S   L>

1550       1560       1570       1580
GGA ACC AGA CAC GAT TTC TTG TAC TCC TTG TTG GGT GAC GGT ATT
 G   T   R   H   D   F   L   Y   S   L   L   G   D   G   I>

1590       1600       1610       1620
TTC ACC TTG GAC GGT GCT GGC TGG AAA CAT AGT AGA ACT ATG TTG
 F   T   L   D   G   A   G   W   K   H   S   R   T   M   L>

1640       1650       1660       1670
AGA CCA CAG TTT GCT AGA GAA CAG GTT TCT CAC GTC AAG TTG TTG
 R   P   Q   F   A   R   E   Q   V   S   H   V   K   L   L>

1680       1690       1700       1710       1720
GAG CCA CAC GTT CAG GTG TTC TTC AAG CAC GTT AGA AAG CAC CGC
 E   P   H   V   Q   V   F   F   K   H   V   R   K   H   R>

1730       1740       1750       1760
GGT CAA ACG TTC GAC ATC CAA GAA TTG TTC TTC AGG TTG ACC GTC
 G   Q   T   F   D   I   Q   E   L   F   F   R   L   T   V>

1770       1780       1790       1800       1810
GAC TCC GCC ACC GAG TTC TTG TTT GGT GAG TCT GCT GAA TCC TTG
 D   S   A   T   E   F   L   F   G   E   S   A   E   S   L>

1820       1830       1840       1850
AGG GAC GAA TCT ATT GGA TTG ACC CCA ACC ACC AAG GAT TTC GAT
 R   D   E   S   I   G   L   T   P   T   T   K   D   F   D>

1860       1870       1880       1890       1900
GGC AGA AGA GAT TTC GCT GAC GCT TTC AAC TAT TCG CAG ACT TAC
 G   R   R   D   F   A   D   A   F   N   Y   S   Q   T   Y>

1910       1920       1930       1940
CAG GCC TAC AGA TTT TTG TTG CAA CAA ATG TAC TGG ATC TTG AAT
 Q   A   Y   R   F   L   L   Q   Q   M   Y   W   I   L   N>

1950       1960       1970       1980       1990
GGC TCG GAA TTC AGA AAG TCG ATT GCT GTC GTG CAC AAG TTT GCT
 G   S   E   F   R   K   S   I   A   V   V   H   K   F   A>
```

```
            2000        2010        2020        2030
      GAC CAC TAT GTG CAA AAG GCT TTG GAG TTG ACC GAC GAT GAC TTG
       D   H   Y   V   Q   K   A   L   E   L   T   D   D   D   L>

2040        2050        2060        2070        2080
  CAG AAA CAA GAC GGC TAT GTG TTC TTG TAC GAG TTG GCT AAG CAA
   Q   K   Q   D   G   Y   V   F   L   Y   E   L   A   K   Q>

2090        2100        2110        2120
    ACC AGA GAC CCA AAG GTC TTG AGA GAC CAG TTA TTG AAC ATT TTG
     T   R   D   P   K   V   L   R   D   Q   L   L   N   I   L>

2130        2140        2150        2160        2170
  GTT GCC GGT AGA GAC ACG ACC GCC GGT TTG TTG TCA TTT GTT TTC
   V   A   G   R   D   T   T   A   G   L   L   S   F   V   F>

2180        2190        2200        2210
    TAC GAG TTG TCA AGA AAC CCT GAG GTG TTT GCT AAG TTG AGA GAG
     Y   E   L   S   R   N   P   E   V   F   A   K   L   R   E>

2220        2230        2340        2250        2260
  GAG GTG GAA AAC AGA TTT GGA CTC GGT GAA GAA GCT CGT GTT GAA
   E   V   E   N   R   F   G   L   G   E   E   A   R   V   E>

2270        2280        2290        2300
    GAG ATC TCG TTT GAG TCC TTG AAG TCT TGT GAG TAC TTG AAG GCT
     E   I   S   F   E   S   L   K   S   C   E   Y   L   K   A>

2310        2320        2330        2340        2350
  GTC ATC AAT GAA ACC TTG AGA TTG TAC CCA TCG GTT CCA CAC AAC
   V   I   N   E   T   L   R   L   Y   P   S   V   P   H   N>

2360        2370        2380        2390
    TTT AGA GTT GCT ACC AGA AAC ACT ACC CTC CCA AGA GGT GGT GGT
     F   R   V   A   T   R   N   T   T   L   P   R   G   G   G>

2400        2410        2420        2430        2440
  GAA GAT GGA TAC TCG CCA ATT GTC GTC AAG AAG GGT CAA GTT GTC
   E   D   G   Y   S   P   I   V   V   K   K   G   Q   V   V>

2450        2460        2470        2480
    ATG TAC ACT GTT ATT GCT ACC CAC AGA GAC CCA AGT ATC TAC GGT
     M   Y   T   V   I   A   T   H   R   D   P   S   I   Y   G>

2490        2500        2510        2520        2530
  GCC GAC GCT GAC GTC TTC AGA CCA GAA AGA TGG TTT GAA CCA GAA
   A   D   A   D   V   F   R   P   E   R   W   F   E   P   E>

2540        2550        2560        2570
    ACT AGA AAG TTG GGC TGG GCA TAC GTT CCA TTC AAT GGT GGT CCA
     T   R   K   L   G   W   A   Y   V   P   F   N   G   G   P>

2580        2590        2600        2610        2620
  AGA ATC TGT TTG GGT CAA CAG TTT GCC TTG ACC GAA GCT TCA TAC
   R   I   C   L   G   Q   Q   F   A   L   T   E   A   S   Y>

2630        2640        2650        2660
    GTC ACT GTC AGA TTG CTC CAG GAG TTT GCA CAC TTG TCT ATG GAC
     V   T   V   R   L   L   Q   E   F   A   H   L   S   M   D>

2670        2680        2690        2700        2710
  CCA GAC ACC GAA TAT CCA CCA AAA TTG CAG AAC ACC TTG ACC TTG
   P   D   T   E   Y   P   P   K   L   Q   N   T   L   T   L>

2720        2730        2740        2750        2760
    TCG CTC TTT GAT GGT GCT GAT GTT AGA ATG TAC TAA GGTTGCTTTTCC
     S   L   F   D   G   A   D   V   R   M   Y   *>

2770        2780        2790        2800        2810        2820
  TTGCTAATTTTCTTCTGTATAGCTTGTGTATTTAAATTGAATCGGCAATTGATTTTTCTG 2830        2840        2850        2860        2870        2880
  ATACCAATAACCGTAGTGCGATTTGACCAAAACCGTTCAAACTTTTTGTTCTCTCGTTGA 2890        2900        2910        2920        2930        2940
  CGTGCTCGCTCATCAGCACTGTTTGAAGACGAAAGAGAAAATTTTTTGTAAACAACACTG 2950        2960        2970        2980        2990        3000
  TCCAAATTTACCCAACGTGAACCATTATGCAAATGAGCGGCCCTTTCAACTGGTCGCTGG
```

-continued

```
        3010      3020      3030      3040      3050      3060
AAGCATTCGGGGATATCTACAACGCCCTTAAGTTTGAAACAGACATTGATTTAGACACCA 3070      3080      3090      3100      3110      3120
TAGATTTCAGCGGCATCAAGAATGACCTTGCCCACATTTTGACGACCCCAACACCACTGG 3130      3140      3150      3160      3170      3180
AAGAATCACGCCAGAAACTAGGCGATGGATCCAAGCCTGTGACCTTGCCCAATGGAGACG 3190      3200      3210      3220      3230      3240
AAGTGGAGTTGAACCAAGCGTTCCTAGAAGTTACCACATTATTGTCGAATGAGTTTGACT 3250      3260      3270      3280      3290      3300
TGGACCAATTGAACGCGGCAGAGTTGTTATACTACGCTGGCGACATATCCTACAAGAAGG 3310      3320      3330      3340      3350      3360
GCACATCAATCGCAGACAGTGCCAGATTGTCTTATTATTTGAGAGCAAACTACATCTTGA 3370      3380      3390      3400      3410      3420
ACATACTTGGGTATTTGATTTCGAAGCAGCGATTGGATTTGATAGTCACGGACAACGACG 3430      3440      3450      3460      3470      3480
CGTTGTTTGATAGTATTTTGAAAAGTTTTGAAAAGATCTACAAGTTGATPAGCGTGTTGA 3490      3500      3510      3520      3530      3540
ACGATATGATTGACAAGCAAAAGGTGACAAGCGACATCAACAGTCTAGCATTCATCAATT 3550      3560      3570      3580      3590      3600
GCATCAACTACTCGAGAGGTCAACTATTCTCCGCACACGAACTTTTGGGACTGGTTTTGT 3610      3620      3630      3640      3650      3660
TTGGATTGGTCGACATCTATTTCAACCAGTTTGGCACATTAGACAACTACAAGAAGGTAT 3670      3680      3690      3700      3710      3720
TGGCATTGATACTGAAGAACATCAGCGATGAAGACATCTTGATCATACACTTCCTCCCAT 3730      3740      3750      3760      3770      3780
CGACACTACAATTGTTTAAGCTGGTGTTGGACAAGAAAGACGACGCTGCAGTTGAACAGT 3790      3800      3810      3820      3830      3840
TCTACAAGTACATCACTTCAACAGTGTCACGAGACTACAACTCCAACATCGGCTCCACAG 3850      3860      3870      3880      3890      3900
CCAAAGATGATATCGATTTGTCCAAAACCAAACTCAGTGGCTTTGAGGTGTTGACGAGTT
```

In order to remove the URS2 at position 666 of the CYP52A3A promoter, first a oligonucleotide beginning at position 600 and extending toward the 3' end at position 770 is made with the exception that base pairs 666-672 are altered. The changes are shown and highlighted below. The AAACCA (SEQ ID NO:8) motif is replaced with GGGTTG (SEQ ID NO:108) so as to preserve spatial structural integrity of the promoter region.

```
                                                          (SEQ ID NO:115)
        610       620       630       640       650       660
CAAGACTTGCATAATTCGAGCTTGGGAGTTCACGCCAATTTGACCTCGTTCATGTGATA 670       680       690       700       710       720
AAAGAGGGGTTGAAAGGTAATTAGCAGACGCAATGGGAACATGGAGTGGAAAGCAATGGA 730       740       750       760       770
AGCACGCCCAGGACGGAGTAATTTAGTCCACACTACATCTGGGG
```

PCR primers as made and used so as to amplify the above DNA fragment.

```
                                            (SEQ ID NO:109)
Primer #1 is 5' CAAGACTTGCATAATTCG 3'
and
                                            (SEQ ID NO:110)
Primer #2 is 5' CCCCAGATGTAGTGTGGAC 3'.
```

Additional primers are made so as to amplify the promoter region upstream of this fragment as well as downstream toward the start codon while incorporating overlappying DNA homology.

```
Primer set UP
             10         20
A)  5' GACATCATAATGACCCGG 3'        (SEQ ID NO:111)
             620        610
B)  5' GCTCGAATTATGCAAGTCTTG 3'     (SEQ ID NO:112)
Primer set DOWN
             750        760
C)  5' TTAGTCCACACTACATCTGGGG 3'    (SEQ ID NO:113)
             1130       1120
D)  5' CATAGTGTAGTTTTTTTTTC 3'      (SEQ ID NO:114)
```

Once all three DNA fragments are made by PCR, they are combined and used in a PCR with primers A and D so as to create a promoter without the URS motif. This promoter is then fused by PCR to the ORF of either the CYP52A3A using methods similar to those above for fusing DNA fragments or to a different target ORF such as CPR.

EXAMPLE 3

Addition of an Upstream Activating Sequence in CYP52A3A

```
    ORE - C/T GGTT A/G TT C/A/G (SEQ ID NO:4)
```

In order to add the ORE at position 666 of the CYP52A3A promoter, first a oligonucleotide beginning at position 600 and extending toward the 3' end at position 770 is made with the exception that base pairs 666-672 are altered. The changes are shown and highlighted below. The AAACCA motif is replaced with TGGTTGTTG.

```
                                                          (SEQ ID NO:115)
        610       620       630       640       650       660
CAAGACTTGCATAATTCGAGCTTGGGAGTTCACGCCAATTTGACCTCGTTCATGTGATA 670       680       690       700       710       720
AAAGATGGTTGTTGAAAGGTAATTAGCAGACGCAATGGGAACATGGAGTGGAAAGCAATGGA 730       740       750       760       770
AGCACGCCCAGGACGGAGTAATTTAGTCCACACTACATCTGGGG
```

PCR primers as made and used so as to amplify the above DNA fragment.

```
                                            (SEQ ID NO:109)
Primer #1 is 5' CAAGACTTGCATAATTCG 3'
and
                                            (SEQ ID NO:110)
Primer #2 is 5' CCCCAGATGTAGTGTGGAC 3'.
```

Additional primers are made so as to amplify the promoter region upstream of this fragment as well as downstream toward the start codon while incorporating overlappying DNA homology.

```
Primer set UP
             10         20
A)  5' GACATCATAATGACCCGG 3'        (SEQ ID NO:111)
             620        610
B)  5' GCTCGAATTATGCAAGTCTTG 3'     (SEQ ID NO:112)
Primer set DOWN
             750        760
C)  5' TTAGTCCACACTACATCTGGGG 3'    (SEQ ID NO:113)
             1130       1120
D)  5' CATAGTGTAGTTTTTTTTTC 3'      (SEQ ID NO: 114)
```

These techniques may be applied to any promoter of any target gene.

What is claimed is:

1. A modified *Candida tropicalis* cytochrome p450 (CYP) CYP52A2A gene promoter having the nucleic acid sequence of SEQ. ID. No. 91 wherein an Upstream Regulatory Sequence-1-like (URS1-like) sequence which consists of SEQ. ID. No. 22 is deleted and wherein activity of said gene promoter is inactivated.

2. An isolated yeast host cell transformed with the modified gene promoter of claim 1.

* * * * *